United States Patent
Hedin

(10) Patent No.: US 10,203,242 B2
(45) Date of Patent: Feb. 12, 2019

(54) METHOD AND A SYSTEM FOR ANALYSING THE CONDITION OF A ROTATING MACHINE PART

(75) Inventor: Lars-Olov Elis Hedin, Hallstahammar (SE)

(73) Assignee: S.P.M. Instrument AB, Strangnas (SE)

( * ) Notice: Subject to any disclaimer, the term of this patent is extended or adjusted under 35 U.S.C. 154(b) by 982 days.

(21) Appl. No.: 14/131,731

(22) PCT Filed: Jul. 11, 2012

(86) PCT No.: PCT/SE2012/050827
§ 371 (c)(1),
(2), (4) Date: Jan. 9, 2014

(87) PCT Pub. No.: WO2013/009258
PCT Pub. Date: Jan. 17, 2013

(65) Prior Publication Data
US 2014/0142872 A1    May 22, 2014

(30) Foreign Application Priority Data
Jul. 14, 2011  (SE) ...................................... 1150683

(51) Int. Cl.
*G01H 1/00* (2006.01)
*G01M 13/04* (2006.01)
(Continued)

(52) U.S. Cl.
CPC .......... *G01H 1/003* (2013.01); *G01M 13/045* (2013.01); *G01N 29/14* (2013.01);
(Continued)

(58) Field of Classification Search
None
See application file for complete search history.

(56) References Cited

U.S. PATENT DOCUMENTS

| 3,554,012 A | 1/1971 | Sohoel |
| 3,705,516 A | 12/1972 | Reis |

(Continued)

FOREIGN PATENT DOCUMENTS

| CN | 1926413 A | 3/2007 |
| CN | 101266197 | 9/2008 |

(Continued)

OTHER PUBLICATIONS

Autocorrelation—Wikipedia, the free encyclopedia, Dec. 12, 2008, p. 2-6, http://en.wikipedia.org/wiki/Autocorrelation.

(Continued)

*Primary Examiner* — John Kuan
(74) *Attorney, Agent, or Firm* — Young & Thompson

(57) ABSTRACT

Method of operating an apparatus for analyzing the condition of a machine part rotating with a speed of rotation, includes: receiving a first digital signal dependent on mechanical vibrations emanating from the rotating part; analyzing the first digital signal to detect peak amplitude values during a finite time period corresponding to a predetermined amount of revolution of the rotatable part; the predetermined amount of revolution corresponding to at least one revolution of the monitored rotatable part; defining a plurality of amplitude ranges, each amplitude range corresponding to a peak occurrence frequency of more than one peak per revolution; sorting the detected peak amplitude values into corresponding amplitude ranges to reflect occurrence of detected peak amplitude values within the plurality of amplitude ranges; establishing a peak amplitude value for detected peaks having an occurrence frequency of about $N_L$ peaks per revolution, the occurrence frequency $N_L$ being a number higher than one.

18 Claims, 18 Drawing Sheets

(51) Int. Cl.
*G01N 29/14* (2006.01)
*G01N 29/48* (2006.01)
*G05B 23/02* (2006.01)
*F16C 19/52* (2006.01)

(52) U.S. Cl.
CPC ............ *F16C 19/527* (2013.01); *G01N 29/48* (2013.01); *G05B 23/0281* (2013.01)

(56) References Cited

U.S. PATENT DOCUMENTS

| | | | |
|---|---|---|---|
| 4,528,852 | A | 7/1985 | Sohoel |
| 4,912,661 | A | 3/1990 | Potter |
| 4,988,979 | A * | 1/1991 | Sasaki ................. G08B 21/187 340/683 |
| 4,991,442 | A | 2/1991 | Matsumoto |
| 5,109,700 | A | 5/1992 | Hicho |
| 5,201,292 | A | 4/1993 | Grajski et al. |
| 5,258,923 | A | 11/1993 | Imam et al. |
| 5,365,787 | A | 11/1994 | Hernandez et al. |
| 5,390,545 | A | 2/1995 | Doan |
| 5,445,028 | A | 8/1995 | Bianchi et al. |
| 5,633,811 | A | 5/1997 | Canada et al. |
| 5,852,793 | A | 12/1998 | Board et al. |
| 5,870,699 | A | 2/1999 | Canada et al. |
| 5,895,857 | A | 4/1999 | Robinson et al. |
| 6,053,047 | A | 4/2000 | Dister et al. |
| 6,332,116 | B1 | 12/2001 | Qian et al. |
| 6,351,713 | B1 | 2/2002 | Board et al. |
| 6,351,714 | B1 | 2/2002 | Birchmeier |
| 6,591,682 | B1 | 7/2003 | Lysen |
| 6,618,128 | B2 | 9/2003 | Van Voorhis et al. |
| 6,801,864 | B2 | 10/2004 | Miller |
| 6,874,364 | B1 | 4/2005 | Campbell et al. |
| 7,010,445 | B2 | 3/2006 | Battenberg et al. |
| 7,133,801 | B2 | 11/2006 | Song |
| 7,136,794 | B1 | 11/2006 | Bechhoefer |
| 7,505,852 | B2 | 3/2009 | Board |
| 7,640,139 | B2 | 12/2009 | Sahara et al. |
| 7,770,458 | B2 | 8/2010 | Blanchard et al. |
| 7,949,496 | B2 | 5/2011 | Lindberg et al. |
| 8,762,104 | B2 | 6/2014 | Hedin |
| 8,810,396 | B2 | 8/2014 | Hedin |
| 8,812,265 | B2 | 8/2014 | Hedin |
| 2003/0130811 | A1 | 7/2003 | Boerhout |
| 2003/0182071 | A1 | 9/2003 | DiTommaso et al. |
| 2004/0101048 | A1 | 5/2004 | Paris |
| 2004/0199348 | A1 | 10/2004 | Hitchcock et al. |
| 2005/0209811 | A1 | 9/2005 | Lindberg et al. |
| 2005/0246150 | A1 | 11/2005 | Shiromaru et al. |
| 2006/0150738 | A1 | 7/2006 | Leigh |
| 2007/0282545 | A1 | 12/2007 | Board |
| 2008/0033695 | A1 | 2/2008 | Sahara et al. |
| 2008/0223135 | A1 | 9/2008 | Blanchard et al. |
| 2009/0164142 | A1 | 6/2009 | Studer et al. |
| 2009/0193900 | A1 | 8/2009 | Janssens et al. |
| 2010/0288051 | A9 | 11/2010 | Janssens et al. |
| 2011/0285532 | A1 | 11/2011 | Hedin |
| 2011/0295556 | A1 | 12/2011 | Hedin |
| 2011/0295557 | A1 | 12/2011 | Hedin |
| 2012/0296582 | A1 | 11/2012 | Hedin |
| 2012/0330580 | A1* | 12/2012 | Fruh ..................... G01M 13/04 702/57 |
| 2014/0365176 | A1 | 12/2014 | Hedin |
| 2014/0372079 | A1 | 12/2014 | Hedin |

FOREIGN PATENT DOCUMENTS

| | | |
|---|---|---|
| DE | 3424692 A1 | 2/1986 |
| EP | 0107178 | 5/1984 |
| EP | 1226414 | 7/2002 |
| EP | 1477783 A2 | 11/2004 |
| EP | 1513254 A1 | 3/2005 |
| GB | 2190198 A | 11/1987 |
| GB | 2451310 A | 1/2009 |
| JP | 60195426 A | 10/1985 |
| JP | 1127934 A | 5/1989 |
| JP | 01178814 A | 7/1989 |
| JP | 04-279826 | 10/1992 |
| JP | 04279826 A | 10/1992 |
| WO | 9513655 A1 | 5/1995 |
| WO | 9527183 A1 | 10/1995 |
| WO | 9605486 A1 | 2/1996 |
| WO | 9801831 A1 | 1/1998 |
| WO | 0004361 A1 | 1/2000 |
| WO | 0103840 A1 | 1/2001 |
| WO | 02073150 A2 | 9/2002 |
| WO | 03062766 A1 | 7/2003 |
| WO | 2007-137132 | 11/2007 |
| WO | 2010-07645 | 7/2010 |
| WO | 2010-074646 | 7/2010 |
| WO | 2010-074648 | 7/2010 |
| WO | 2011-087440 | 7/2011 |

OTHER PUBLICATIONS

Chang et al., "A Novel Envelope Detector for High-Frame Rate, High-Frequency Ultrasound Imaging", IEEE Transactions on Ultrasonics, Ferroelectrics, and Frequency Control, 2007, vol. 54, No. 9, pp. 1792-1801.
Dominick, Joe, "PeakVue as Part of a Reliability Based Maintenance Program", Emerson Process Management—CSI, DoctorKnow® Application Paper, 2010 pp. 1-15.
Elliott et al., "13.2 Correlation and Autocorrelation Using the FFT", Fast Transforms: Algorithms, Analyses, Applications (New York: Academic Press), 1982, pp. 545-547.
Milman, Andrew, "Mathematical Principles of Remote Sensing: Making Inferences from Noisy Data", Sleeping Bear Press, Michigan, 1999, pp. 215-233.
Robinson, James C., "Autocorrelation as a Diagnostic Tool", 2007, pp. 1-22.
Robinson et al., "How Advanced Analysis Identifies Lubrication Problems", Machinery Health, Pumps & Systems, 2007, pp. 66-67.
Autocorrelation from Wikipedia, 2009, http://en.wikipedia.org/wiki/autocorrelation, pp. 1-6.
CN Office Action, dated Apr. 29, 2015; Application No. 2012800347548.
Extended European search report, dated Sep. 2, 2015; Application No. 13744257.0.
Extended European search report, dated Sep. 16, 2015; Application No. 12810816.4.
James Lundy, "Detecting Lubrication Problems Using Shock Pulse," Lubrication & Fluid Power, Feb. 2006.
International Search Report, dated Sep. 11, 2012, from corresponding PCT application.
Supplemental Partial European Search Report in corresponding European Application No. 13837138, dated May 4, 2016.
CN OA dated Nov. 23, 2015; Application No. 201380007381X.

* cited by examiner

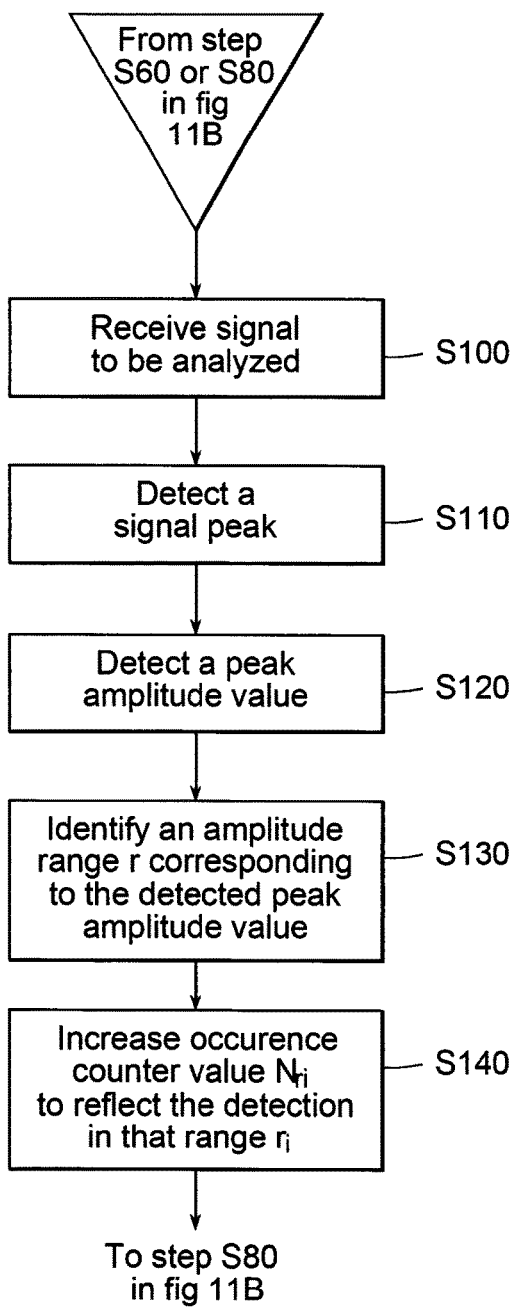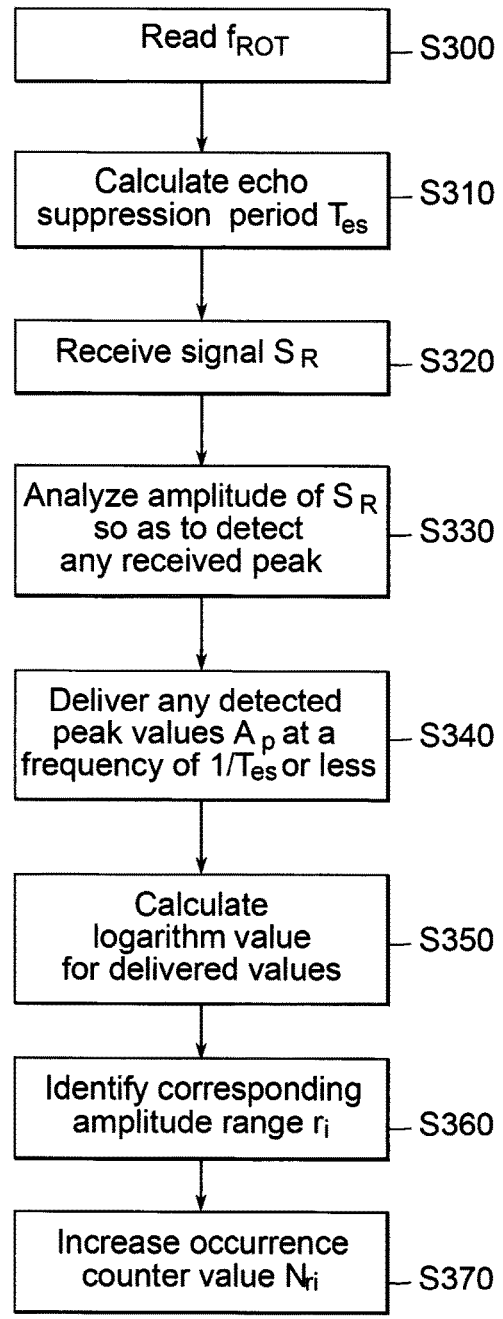
Fig. 12A
Fig. 12B

METHOD AND A SYSTEM FOR ANALYSING THE CONDITION OF A ROTATING MACHINE PART

TECHNICAL FIELD OF THE INVENTION

The present invention relates to a method for analysing the condition of a machine, and to an apparatus for analysing the condition of a machine. The invention also relates to a system including such an apparatus and to a method of operating such an apparatus. The invention also relates to a computer program for causing a computer to perform an analysis function.

DESCRIPTION OF RELATED ART

Machines with moving parts are subject to wear with the passage of time, which often causes the condition of the machine to deteriorate. Examples of such machines with movable parts are motors, pumps, generators, compressors, lathes and CNC-machines. The movable parts may comprise a shaft and bearings.

In order to prevent machine failure, such machines should be subject to maintenance, depending on the condition of the machine. Therefore the operating condition of such a machine is preferably evaluated from time to time. The operating condition can be determined by measuring vibrations emanating from a bearing or by measuring temperature on the casing of the machine, which temperatures are dependent on the operating condition of the bearing. Such condition checks of machines with rotating or other moving parts are of great significance for safety and also for the length of the life of such machines. It is known to manually perform such measurements on machines. This ordinarily is done by an operator with the help of a measuring instrument performing measurements at measuring points on one or several machines.

A number of commercial instruments are available, which rely on the fact that defects in rolling-element bearings generate short pulses, usually called shock pulses. A shock pulse measuring apparatus may generate information indicative of the condition of a bearing or a machine.

WO 03062766 discloses a machine having a measuring point and a shaft with a certain shaft diameter, wherein the shaft can rotate when the machine is in use. WO 03062766 also discloses an apparatus for analysing the condition of a machine having a rotating shaft. The disclosed apparatus has a sensor for producing a measured value indicating vibration at a measuring point. The apparatus disclosed in WO 03062766 has a data processor and a memory. The memory may store program code which, when run on the data processor, will cause the analysis apparatus to perform a Machine Condition Monitoring function. Such a Machine Condition Monitoring function may include shock pulse measuring.

When a ball or roller bearing is correctly mounted, adequately lubricated, and otherwise properly handled, the conditions which cause failure are substantially eliminated, with the exception of material fatigue. In a proper bearing installation, the effectiveness of the bearing lubricant is dependent upon its ability to adequately separate the rolling surfaces. The thickness of the thin, protective elastohydrodynamic lubricant film is often only slightly greater than the sum of the roughnesses of the lubricated bearing surfaces separated by it. Theoretical and analytical investigations have resulted in development of an elastohydrodynamic lubricant film parameter to rate effectiveness of lubrication in ball and roll bearing applications. The later parameter comprises a function of the lubricant film thickness and the roughness of the lubricated surfaces. Theoretical predictions which provide the basis for the elastohydrodynamic lubricant film parameter for both nominal line and point contacts in rolling element bearings have been experimentally confirmed utilizing such techniques as capacitance measurement coupled with knowledge of the dielectric constant of the lubricant to estimate film thickness. Other experimental investigations utilizing X-ray transmission techniques, transparent components, and interferometry have been used to study lubricant film thickness and shape. A qualitative indication of the effect of the lubricant film thickness on bearing endurance has also been obtained by measuring the time percentage in an operating bearing during which metal-to-metal contact is prevented by the presence of the lubricant film.

The value of the elastohydrodynamic lubricant film parameter $\Lambda$ generally falls within the range of 0.8 to 4 for most bearing applications. When the value of $\Lambda$ is less than 0.8 a risk of surface distress exists due to sporatic interruption of the lubricant film indicating that corrective measures may be required to improve lubrication. A value of $\Lambda$ greater than 4 indicates continuous separation of rolling surfaces by a full elastohydrodynamic lubricant film. When this condition exists, the "rating life" for the bearing may be expected to be at least twice the listed catalog rating for the particular bearing. However, under optimal operational conditions, where it is desired to minimize bearing play while maintaining adequate film separation for satisfactory bearing life, the value of $\Lambda$ will be somewhat less than 4. Such a condition may be desirable, for example, in a precision apparatus, such as a lead screw mechanism, machine spindle or the like.

The theoretical value of $\Lambda$ for both nominal line contact, in a roller bearing, or point contact in a ball bearing application may be calculated and such calculation is of great utility in the analysis and design of roller and ball bearing applications. The accuracy of design criteria may be confirmed by one of the experimental techniques hereinbefore generally described, however, while such experimental techniques are of value in checking the theoretically predicted lubricant film thickness, they do not afford practical means for evaluating the lubricational condition of a bearing under field operating conditions.

Many bearing installations operate under less than ideal conditions, normally assumed or provided in most theoretical and experimental investigations. An important practical consideration is the supply and distribution of lubricant in the vicinity of the rolling element contact region. Lubricant starvation which often exists, but is not always recognized, can have an overriding effect on lubricant film thickness and other elastohydrodynamic aspects of bearing operation.

SUMMARY

An aspect of the invention relates to the problem of providing an improved method and an improved apparatus for analysis of the condition of a machine having a rotating part.

This problem is addressed by a method of operating an apparatus for analysing the condition of a machine part rotating with a speed of rotation ($f_{ROT}$, $V_r$), comprising the steps of:

receiving a first digital signal ($S_{MD}$, $S_R$, $S_F$) dependent on mechanical vibrations emanating from rotation of said part;

analysing said first digital signal so as to detect peak amplitude values ($A_{PL}$) during a finite time period ($T_{Pm}$), said finite time period corresponding to a predetermined amount ($R_S$) of revolution of said rotatable part; said predetermined amount ($R_S$) of revolution corresponding to at least one revolution of said monitored rotatable part;

defining a plurality of amplitude ranges, each amplitude range corresponding to a peak occurrence frequency of more than one peak per revolution;

sorting said detected peak amplitude values (Ap) into corresponding amplitude ranges so as to reflect occurrence of detected peak amplitude values (Ap) within said plurality of amplitude ranges;

establishing a peak amplitude value ($A_{PL}$) for detected peaks having an occurrence frequency of about $N_L$ peaks per revolution, said occurrence frequency value $N_L$ being a number higher than one.

Various embodiments of the method and the apparatus are disclosed below. An embodiment 1 of the invention comprises: A method of operating an apparatus for analysing the condition of a machine part rotating with a speed of rotation ($f_{ROT}$, $V_r$), comprising the steps of:

receiving a first digital signal ($S_{MD}$, $S_R$, $S_F$) dependent on mechanical vibrations emanating from rotation of said part;

analysing said first digital signal so as to detect peak amplitude values ($A_{PL}$) during a finite time period ($T_{Pm}$), said finite time period corresponding to a predetermined amount ($R_S$, $R_D$) of revolution of said rotatable part; said predetermined amount ($R_S$, $R_D$) of revolution corresponding to at least one revolution of said monitored rotatable part;

defining a plurality of amplitude ranges, each amplitude range corresponding to a peak occurrence frequency of more than one peak per revolution;

sorting said detected peak amplitude values (Ap) into corresponding amplitude bins so as to
reflect (470) occurrence (N) of detected peak amplitude values (Ap) within a plurality of amplitude range bins, or so as to
reflect (530) occurrence (N') of detected peaks having an amplitude higher than the amplitude ($A_r'$) of associated amplitude bin (r);

establishing a peak amplitude value ($A_{PL}$) for detected peaks having an occurrence (N') frequency of about $N_L$ peaks per revolution, said occurrence frequency value $N_L$ being a number higher than one.

Embodiment 2. A method of operating an apparatus for analysing the condition of a machine part rotating with a speed of rotation ($f_{ROT}$, $V_r$), comprising:

performing a procedure for establishing a plurality of reference values ($A_{PLrefVr}$) for a particular type of bearing for plural rotational speeds ($f_{ROT}$, $V_r$); the reference value establishing procedure including the steps of:

monitoring the unlubricated control bearing when running at two different speeds of revolution, recording, as a first reference value ($A_{PLrefV1}$), the peak amplitude value ($A_{PL}$) for detected peaks having an occurrence frequency of about $N_L$ peaks per revolution when running the rotating part at the first speed (V1), said occurrence frequency value $N_L$ being a number higher than one, and recording, as a second reference value ($A_{PLrefV2}$), the peak amplitude value ($A_{PL}$) for detected peaks having an occurrence frequency of about $N_L$ peaks per revolution when running the bearing at the second speed (V2), estimating a third reference value ($A_{PLrefV3}$) for use as a third reference ($A_{PLrefV3}$) when a monitored bearing runs at a third speed (V3), said third reference value ($A_{PLrefV3}$) being generated in dependence on said first reference value ($A_{PLrefV1}$) and said second reference value ($A_{PLrefV2}$).

Embodiment 3. The method according to Embodiment 1 or 2, wherein the amplitude of detected peaks having an occurrence frequency of about $N_L$ peaks per revolution are used for indication a lubrication condition.

Embodiment 4. The method according to any preceding embodiment, wherein said establishing step includes:

identifying, when said predetermined amount ($R_S$, $R_D$) of revolution has been achieved, an amplitude bin within which X amplitude values were counted, wherein $X = R_D * N_L$, and wherein $R_D$ is a number corresponding to said predetermined amount ($R_S$, $R_D$) of revolution; and using the amplitude value of said identified amplitude range as said peak amplitude value ($A_{PL}$).

Embodiment 5. The method according to embodiment 5, wherein

Said amplitude range is a range (500, r) in a histogram of detected peak amplitude values.

Embodiment 6. The method according to any of embodiments 1-3, wherein said establishing step includes:

identifying, when said predetermined amount ($R_S$, $R_D$) of revolution has been achieved, an amplitude bin within which Z amplitude values were counted, wherein
Z reflects (530) occurrence (N') of detected peaks having an amplitude higher than the amplitude ($A_r'$) of the associated amplitude bin (r); and $Z = R_D * N_L$, and wherein $R_D$ is a number corresponding to said predetermined amount of revolution; and said establishing step further includes using the amplitude value of said identified amplitude range as said peak amplitude value ($A_{PL}$).

Embodiment 7. The method according to any preceding embodiment, wherein said finite time period ($T_{Pm}$) is determined (875) in dependence on a preset amount ($R_S$) of revolution value and a signal indicative of an actual amount ($R_D$) of revolution; wherein said predetermined amount ($R_S$, $R_D$) of revolution corresponding to at least one revolution of said monitored rotatable part; or said predetermined amount ($R_S$, $R_D$) of revolution corresponding to at least two revolutions of said monitored rotatable part; or said predetermined amount ($R_S$, $R_D$) of revolution corresponding to at least three revolutions of said monitored rotatable part; or said predetermined amount ($R_S$, $R_D$) of revolution corresponding to at least four revolutions of said monitored rotatable part; or said predetermined amount ($R_S$, $R_D$) of revolution corresponding to at least eight revolutions of said monitored rotatable part; or said predetermined amount ($R_S$, $R_D$) of revolution corresponding to at least ten revolutions of said monitored rotatable part.

Embodiment 8. The method according to any of embodiments 1-3, wherein said establishing step includes:

selecting the Y:th highest amplitude peak value to be said peak amplitude value ($A_{PL}$) indicative of a lubrication condition; wherein $$Y = R_S * N_L$$

and wherein $R_S$ is said predetermined amount ($R_S$) of revolution; and $N_L$ is an integer having a value higher than one (1).

Embodiment 9. A method of operating an apparatus for analysing the lubrication condition of a machine part rotating with a speed of rotation ($f_{ROT}$), comprising the steps of:

receiving a first digital signal ($S_{MD}$, $S_R$, $S_F$) dependent on mechanical vibrations emanating from rotation of said part;

analysing said first digital signal so as to detect peak amplitude values (Ap) during a finite time period ($T_{PmL}$), said finite time period corresponding to a certain amount ($R_D$) of revolution of said rotatable part; said certain amount ($R_D$) of revolution corresponding to more than one revolution of said monitored rotatable part;

sorting said detected peak amplitude values (Ap) into corresponding amplitude bins so as to reflect (470) occurrence (N) of detected peak amplitude values (Ap) within a plurality of amplitude range bins, or so as to reflect (530) occurrence (N') of detected peaks having an amplitude higher than the amplitude ($A_r'$) of associated amplitude bin (r);

identifying an amplitude range (r) containing sorted peak amplitude values $A_{PL}$ which, during the finite time period ($T_{PmL}$) had a mean occurrence frequency ($N_L$) of more than once per revolution.

Embodiment 10. A method of operating an apparatus for analysing the condition of a machine part rotating with a speed of rotation ($f_{ROT}$, $V_r$), comprising the steps of:

receiving a first digital signal ($S_{MD}$, $S_R$, $S_F$) dependent on mechanical vibrations emanating from rotation of said part;

analysing said first digital signal so as to detect peak amplitude values ($A_{PL}$) during a finite time period ($T_{Pm}$), said finite time period corresponding to a predetermined amount (A) of revolution of said rotatable part; said predetermined amount (A) of revolution corresponding to at least one revolution of said monitored rotatable part;

sorting said detected peak amplitude values (Ap) into corresponding amplitude bins so as to reflect (470) occurrence (N) of detected peak amplitude values (Ap) within a plurality of amplitude range bins, or so as to reflect (530) occurrence (N') of detected peaks having an amplitude higher than the amplitude ($A_r'$) of associated amplitude bin (r);

using the amplitude value ($A_{PR}$) associated with at least one first amplitude range among said amplitude ranges as a value indicative of a first type of condition of said rotating part; and using the amplitude value ($A_{PL}$) associated with at least one second amplitude range among said amplitude ranges as a value indicative of a second type of condition of said rotating part.

Embodiment 11. A method of operating an apparatus for analysing the condition of a machine part rotating with a speed of rotation ($f_{ROT}$, $V_r$), comprising the steps of:

receiving a first digital signal ($S_{MD}$, $S_R$, $S_F$) dependent on mechanical vibrations emanating from rotation of said part;

analysing said first digital signal so as to detect peak amplitude values ($A_{PL}$) during a finite time period ($T_{Pm}$), said finite time period corresponding to a predetermined amount (A) of revolution of said rotatable part; said predetermined amount (A) of revolution corresponding to at least one revolution of said monitored rotatable part;

sorting said detected peak amplitude values (Ap) into corresponding amplitude bins so as to reflect (470) occurrence (N) of detected peak amplitude values (Ap) within a plurality of amplitude range bins, or so as to reflect (530) occurrence (N') of detected peaks having an amplitude higher than the amplitude ($A_r'$) of associated amplitude bin (r);

using the amplitude value ($A_{PL}$, $A_{PR}$) associated with at least two amplitude bins among said amplitude bins as a value indicative of a type of condition of said rotating part;

discriminating between
amplitude values ($A_{PL}$, $A_{PR}$) used for indicating a lubrication condition of bearing surfaces and
amplitude values ($A_{PL}$, $A_{PR}$) used for indicating a mechanical state of bearing surfaces based on the number of occurrences ($N_L$, $N_R$) per revolution of said peak values.

Embodiment 12. The method according to embodiment 11, wherein amplitude values ($A_{PL}$) used for indicating a lubrication condition of bearing surfaces have a first occurrence frequency value ($N_L$) in number of peak values per revolution;

said first occurrence frequency value ($N_L$) being a number higher than one peak value per revolution.

Embodiment 13. The method according to embodiment 11 or 12, wherein amplitude values ($A_{PR}$) used for indicating a mechanical state of bearing surfaces of bearing surfaces have a second occurrence frequency value in number of peak values per revolution;

said second occurrence frequency value being a number lower than one peak value per revolution.

Embodiment 14. The method according to any preceding embodiment, wherein
said occurrence frequency value $N_L$ is a number higher than ten.

Embodiment 15. The method according to any preceding embodiment, wherein
said occurrence frequency value $N_L$ is a number in the range from 15 to 150.

Embodiment 16. The method according to any preceding embodiment, wherein
said occurrence frequency value $N_L$ is a number in the range from 20 to 90.

Embodiment 17. The method according to any preceding embodiment, wherein
said occurrence frequency value $N_L$ is a number in the range from 25 to 70.

Embodiment 18. The method according to any preceding embodiment, wherein
said occurrence frequency value $N_L$ reflects a number of peak values per revolution of a monitored part.

Embodiment 19. A procedure for establishing reference values ($A_{PRrefVr}$) for a bearing associated with a rotatable part, including the steps of:
receiving a first digital signal ($S_{MD}$, $S_R$, $S_F$) dependent on mechanical vibrations emanating from rotation of said rotatable part;
analysing said first digital signal so as to detect peak amplitude values (Ap) during a finite time period ($T_{Pm}$), said finite time period corresponding to a certain amount (R) of revolution of said bearing; said certain amount (R) of revolution corresponding to more than one revolution of said monitored rotatable part;
monitoring a control bearing when running at two different speeds of revolution,
recording, as a first reference value ($A_{PRV1}$), the highest signal peak value ($A_{pR}$) occurring once every R:th revolution when running the control bearing at the first speed, and
recording, as a second reference value ($A_{PRV2}$), the highest signal peak value ($A_{PR}$) occurring once every R:th revolution when running the control bearing at the second speed,
estimating a third reference value ($A_{PRV3}$) for use as a reference when a monitored bearing runs at a third speed, said third reference value ($A_{PRV3}$) being generated in dependence on said first reference value ($A_{PRV1}$) and said second reference value ($A_{PRV2}$).

Embodiment 20. An apparatus for performing the method according to any preceding embodiment.

Embodiment 21. A method of operating an apparatus for analysing the condition of a machine having a part rotating with a speed of rotation ($f_{ROT}$), comprising the steps of:
receiving a first digital signal ($S_{MD}$, $S_R$, $S_F$) dependent on mechanical vibrations emanating from rotation of said part;
analysing said first digital signal so as to detect peak amplitude values (Ap) during a finite time period ($T_{Pm}$), said finite time period corresponding to a certain amount (R) of revolution of said rotatable part; said certain amount (R) of revolution corresponding to more than one revolution of said monitored rotatable part;
defining a plurality ($N_R$) of amplitude ranges;
sorting said detected peak amplitude values (Ap) into corresponding amplitude ranges so as to reflect occurrence (N) of detected peak amplitude values (Ap) within said plurality of amplitude ranges;
estimating a representative peak amplitude value ($A_{PR}$) in dependence on said sorted peak amplitude values (Ap) and said certain amount (R).

Embodiment 22. The method according to embodiment 21, further comprising
Delivering said representative peak amplitude value ($A_{PR}$) to a user interface for presentation to a user.

Embodiment 23. The method according to embodiment 21 or 22, further comprising
performing a condition monitoring function (F1, F2, Fn) so as to analyse the condition of the machine dependent on said representative peak amplitude value ($A_{PR}$).

Embodiment 24. The method according to any preceding embodiment, wherein said estimation includes selecting the R:th highest amplitude to be said representative peak amplitude value ($A_{PR}$).

Embodiment 25. The method according to any preceding embodiment, wherein said estimation includes the creation of an accumulative histogram.

Embodiment 26. The method according to any preceding embodiment, wherein the amplitude levels emanating from rotation of the monitored rotational part closely follow the normal distribution, also referred to as the Gaussian distribution; and wherein
amplitude levels originating from plural revolutions of the rotational part are recorded in order to detect a relevant true peak value which is used for determination of the condition of the monitored rotational part.

Embodiment 27. The method according to any preceding embodiment, wherein
the estimation step includes estimating a not-so-frequent highest peak amplitude value ($A_{PR}$, 590) based on the nature of the Gaussian function or bell curve being such that an occurrence frequency of low amplitude values (550, 560) is informative about the amplitude of the not-so-frequent highest peak amplitude values ($A_{PR}$, 590).

Embodiment 28. The method according to any preceding embodiment, wherein
said certain amount of revolution includes at least n*R revolutions, wherein n is a number having a numerical value of at least one and R has a numerical value of at least 8.

Embodiment 29. The method according to embodiment 28, wherein
the numerical value of n is at least two; and
the estimation step includes selecting the n:th highest detected peak amplitude.

Embodiment 30. The method according to any of embodiments 28 or 29, wherein
the numerical value of R is at least 10.

Embodiment 31. A method of operating an apparatus for analysing the condition of a machine having a part rotating with a speed of rotation ($f_{ROT}$), comprising the steps of:
receiving a first digital signal ($S_{MD}$, $S_R$, $S_F$) dependent on mechanical vibrations emanating from rotation of said part;
analysing said first digital signal so as to detect peak amplitude values (Ap) during a finite time period ($T_{Pm}$), said finite time period corresponding to a certain amount (R) of revolution of said rotatable part; said certain amount (R) of revolution corresponding to more than one revolution of said monitored rotatable part;
defining a plurality ($N_R$) of amplitude ranges;
sorting said detected peak amplitude values (Ap) into corresponding amplitude ranges so as to reflect occurrence (N) of detected peak amplitude values (Ap) within said plurality of amplitude ranges;
estimating a representative peak amplitude value ($A_{PR}$, 630, 640, 650, 660) in dependence on said sorted peak amplitude values (Ap) and said certain amount (R)
comparing said representative peak amplitude value ($A_{PR}$) with reference information; and
generating a value indicative of a detected relative damage by relating said representative peak amplitude value ($A_{PR}$, 630, 640, 650) to corresponding reference information ($A_{PRrefVr}$, 620).

BRIEF DESCRIPTION OF THE DRAWINGS

For simple understanding of the present invention, it will be described by means of examples and with reference to the accompanying drawings, of which.

FIG. 12A is a flow chart illustrating an embodiment of a method of performing a peak level measurement session.

FIG. 12B is a flow chart illustrating an embodiment of a method of performing a peak level measurement session and addressing the impact of bursts of noise amplitude peaks.

DETAILED DESCRIPTION OF EMBODIMENTS

Figure 1:
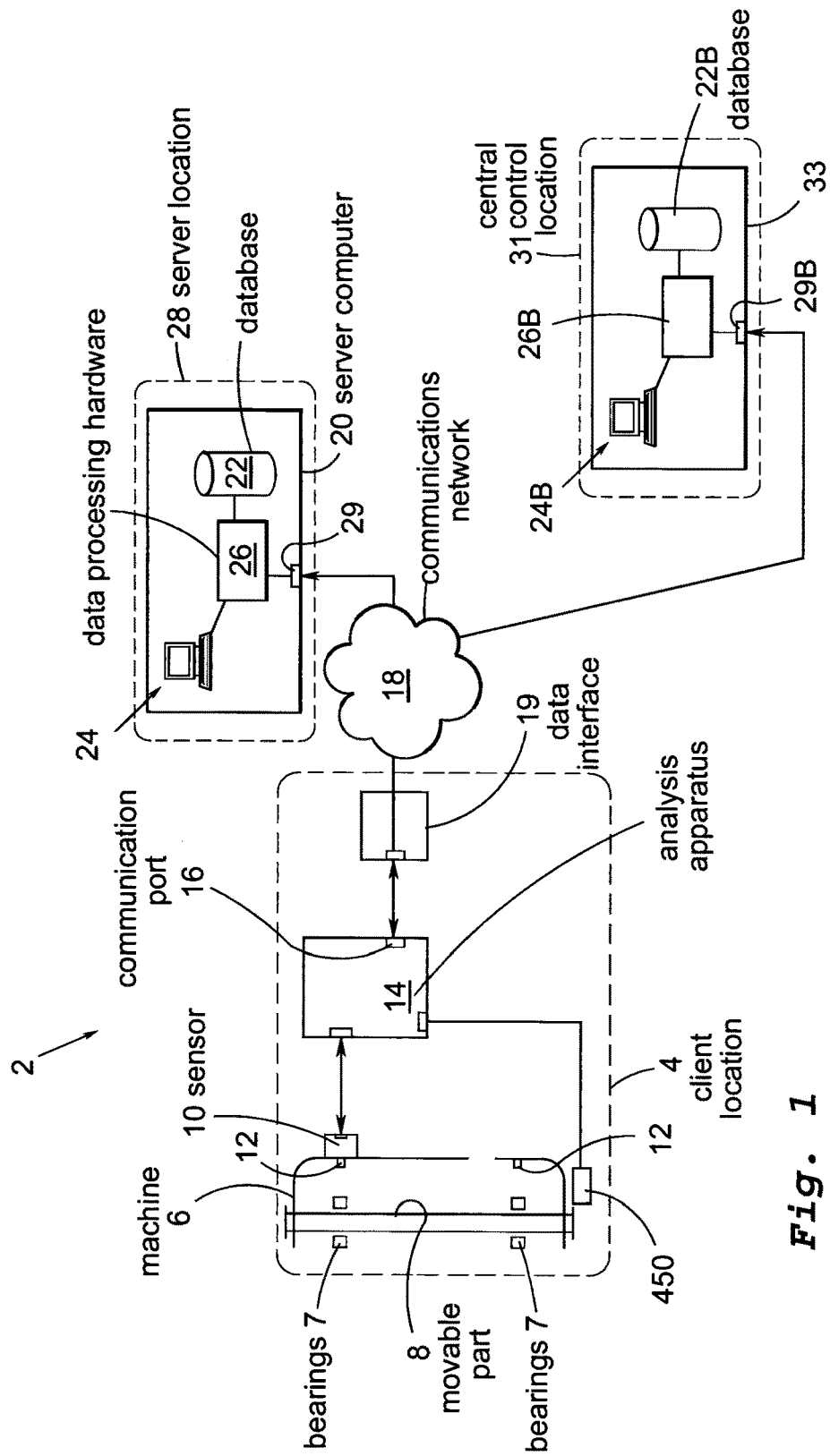
FIG. 1 shows a schematic block diagram of an embodiment of a condition analyzing system 2 according to an embodiment of the invention including an analysis apparatus.

In the following description similar features in different embodiments may be indicated by the same reference numerals.

FIG. 1 shows a schematic block diagram of an embodiment of a condition analyzing system 2 according to an embodiment of the invention. Reference numeral 4 relates to a client location with a machine 6 having a movable part 8. The movable part may comprise bearings 7 and a shaft 8 which, when the machine is in operation, rotates. The operating condition of the shaft 8 or of a bearing 7 can be determined in response to vibrations emanating from the shaft and/or bearing when the shaft rotates. The client location 4, which may also be referred to as client part or user part, may for example be the premises of a wind farm, i.e. a group of wind turbines at a location, or the premises of a paper mill plant, or some other manufacturing plant having machines with movable parts.

An embodiment of the condition analyzing system 2 is operative when a sensor 10 is attached on or at a measuring point 12 on the body of the machine 6. Although FIG. 1 only illustrates two measuring points 12, it to be understood that a location 4 may comprise any number of measuring points 12. The condition analysis system 2 shown in FIG. 1, comprises an analysis apparatus 14 for analysing the condition of a machine on the basis of measurement values delivered by the sensor 10.

The analysis apparatus 14 has a communication port 16 for bi-directional data exchange. The communication port 16 is connectable to a communications network 18, e.g. via a data interface 19. The communications network 18 may be the world wide internet, also known as the Internet. The communications network 18 may also comprise a public switched telephone network.

A server computer 20 is connected to the communications network 18. The server 20 may comprise a database 22, user input/output interfaces 24 and data processing hardware 26, and a communications port 29. The server computer 20 is located on a location 28, which is geographically separate from the client location 4. The server location 28 may be in a first city, such as the Swedish capital Stockholm, and the client location may be in another city, such as Stuttgart, Germany or Detroit in Michigan, USA. Alternatively, the server location 28 may be in a first part of a town and the client location may be in another part of the same town. The server location 28 may also be referred to as supplier part 28, or supplier part location 28.

According to an embodiment of the invention a central control location 31 comprises a control computer 33 having data processing hardware and software for surveying a plurality of machines at the client location 4. The machines 6 may be wind turbines or gear boxes used in wind turbines. Alternatively the machines may include machinery in e.g. a paper mill. The control computer 33 may comprise a database 22B, user input/output interfaces 24B and data processing hardware 26B, and a communications port 29B. The central control location 31 may be separated from the client location 4 by a geographic distance. By means of communications port 29B the control computer 33 can be coupled to communicate with analysis apparatus 14 via port 16. The analysis apparatus 14 may deliver measurement data being partly processed so as to allow further signal processing and/or analysis to be performed at the central location 31 by control computer 33.

A supplier company occupies the supplier part location 28. The supplier company may sell and deliver analysis apparatuses 14 and/or software for use in an analysis apparatus 14. The supplier company may also sell and deliver analysis software for use in the control computer at the central control location 31. Such analysis software 94,105 is discussed in connection with FIG. 4 below. Such analysis software 94,105 may be delivered by transmission over said communications network 18.

According to one embodiment of the system 2 the apparatus 14 is a portable apparatus which may be connected to the communications network 18 from time to time.

According to another embodiment of the system 2 the apparatus 14 is connected to the communications network 18 substantially continuously. Hence, the apparatus 14 according to this embodiment may substantially always be "on line" available for communication with the supplier computer 20 and/or with the control computer 33 at control location 31.

Figure 2A:
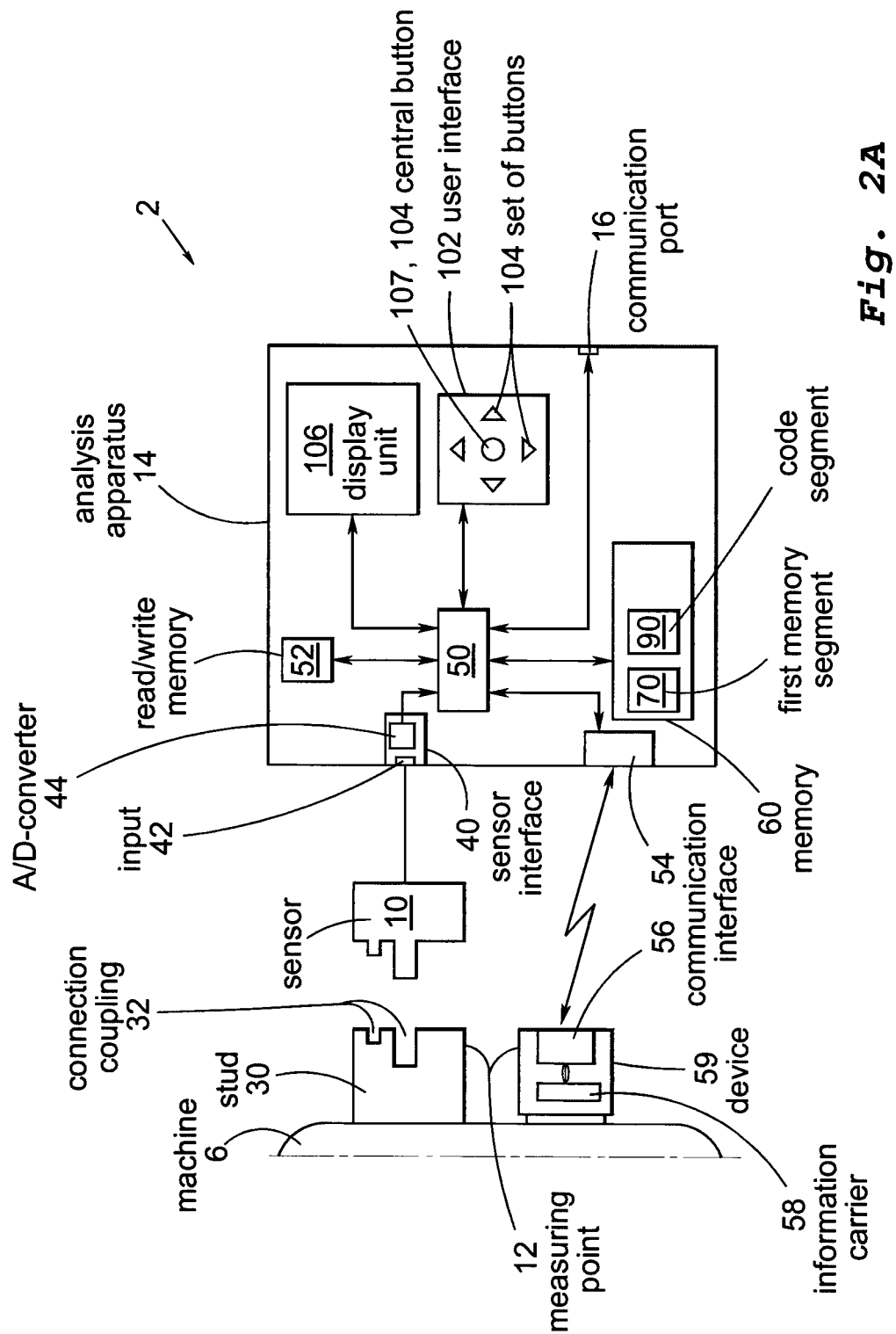
FIG. 2A is a schematic block diagram of an embodiment of a part of the condition analyzing system 2 shown in FIG. 1 including an embodiment of an analysis apparatus.

FIG. 2A is a schematic block diagram of an embodiment of a part of the condition analyzing system 2 shown in FIG. 1. The condition analyzing system, as illustrated in FIG. 2A, comprises a sensor unit 10 for producing a measured value. The measured value may be dependent on movement or, more precisely, dependent on vibrations or shock pulses caused by bearings when the shaft rotates.

An embodiment of the condition analyzing system 2 is operative when a device 30 is firmly mounted on or at a measuring point on a machine 6. The device 30 mounted at the measuring point may be referred to as a stud 30. A stud 30 can comprise a connection coupling 32 to which the sensor unit 10 is removably attachable. The connection coupling 32 can, for example comprise double start threads for enabling the sensor unit to be mechanically engaged with the stud by means of a ¼ turn rotation.

A measuring point 12 can comprise a threaded recess in the casing of the machine. A stud 30 may have a protruding part with threads corresponding to those of the recess for enabling the stud to be firmly attached to the measuring point by introduction into the recess like a bolt.

Alternatively, a measuring point can comprise a threaded recess in the casing of the machine, and the sensor unit 10 may comprise corresponding threads so that it can be directly introduced into the recess. Alternatively, the measuring point is marked on the casing of the machine only with a painted mark.

The machine 6 exemplified in FIG. 2A may have a rotating shaft with a certain shaft diameter d1. The shaft in the machine 6 may rotate with a speed of rotation V1 when the machine 6 is in use.

The sensor unit 10 may be coupled to the apparatus 14 for analysing the condition of a machine. With reference to FIG. 2A, the analysis apparatus 14 comprises a sensor interface 40 for receiving a measured signal or measurement data, produced by the sensor 10. The sensor interface 40 is coupled to a data processing means 50 capable of controlling the operation of the analysis apparatus 14 in accordance with program code. The data processing means 50 is also coupled to a memory 60 for storing said program code.

According to an embodiment of the invention the sensor interface 40 comprises an input 42 for receiving an analogue signal, the input 42 being connected to an analogue-to-digital (A/D) converter 44, the digital output 48 of which is coupled to the data processing means 50. The A/D converter 44 samples the received analogue signal with a certain sampling frequency $f_S$ so as to deliver a digital measurement data signal $S_{MD}$ having said certain sampling frequency $f_S$ and wherein the amplitude of each sample depends on the amplitude of the received analogue signal at the moment of sampling.

Figure 2B:
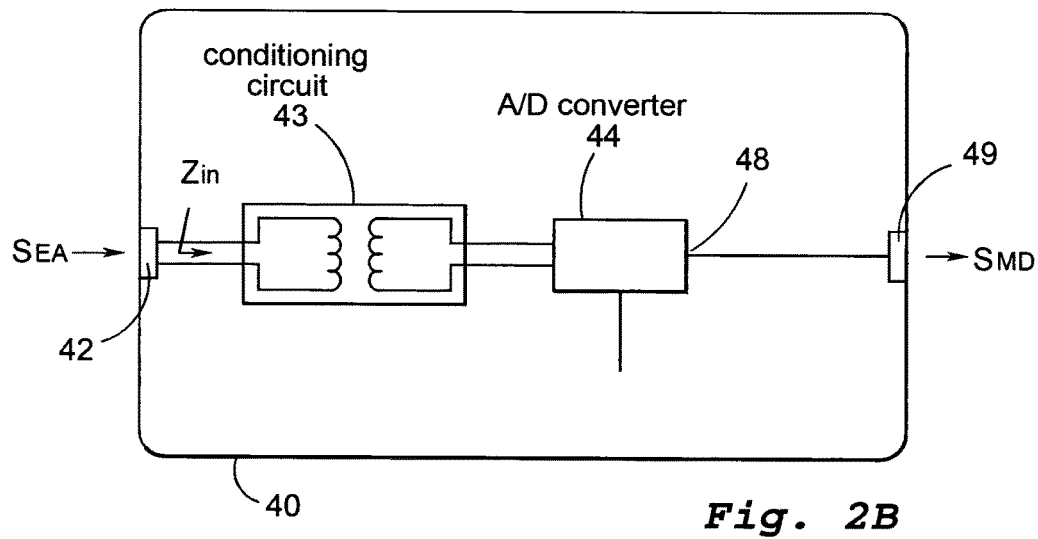
FIG. 2B is a schematic block diagram of an embodiment of a sensor interface.

According to another embodiment of the invention, illustrated in FIG. 2B, the sensor interface 40 comprises an input 42 for receiving an analogue signal $S_{EA}$ from a Shock Pulse Measurement Sensor, a conditioning circuit 43 coupled to receive the analogue signal, and an A/D converter 44 coupled to receive the conditioned analogue signal from the conditioning circuit 43. The A/D converter 44 samples the received conditioned analogue signal with a certain sampling frequency $f_S$ so as to deliver a digital measurement data signal $S_{MD}$ having said certain sampling frequency $f_S$ and wherein the amplitude of each sample depends on the amplitude of the received analogue signal at the moment of sampling.

The sampling theorem guarantees that bandlimited signals (i.e., signals which have a maximum frequency) can be reconstructed perfectly from their sampled version, if the sampling rate $f_S$ is more than twice the maximum frequency $f_{SEAmax}$ of the analogue signal $S_{EA}$ to be monitored. The frequency equal to one-half of the sampling rate is therefore a theoretical limit on the highest frequency that can be unambiguously represented by the sampled signal $S_{MD}$. This frequency (half the sampling rate) is called the Nyquist frequency of the sampling system. Frequencies above the Nyquist frequency $f_N$ can be observed in the sampled signal, but their frequency is ambiguous. That is, a frequency component with frequency f cannot be distinguished from other components with frequencies $B*f_N+f$, and $B*f_N-f$ for nonzero integers B. This ambiguity, known as aliasing may be handled by filtering the signal with an anti-aliasing filter (usually a low-pass filter with cutoff near the Nyquist frequency) before conversion to the sampled discrete representation.

In order to provide a safety margin for in terms of allowing a non-ideal filter to have a certain slope in the frequency response, the sampling frequency may be selected to a higher value than 2. Hence, according to embodiments of the invention the sampling frequency may be set to $$f_S = k * f_{SEAmax}$$

wherein k is a factor having a value higher than 2.0

Accordingly the factor k may be selected to a value higher than 2.0. Preferably factor k may be selected to a value between 2.0 and 2.9 in order to provide a good safety margin while avoiding to generate unnecessarily many sample values. According to an embodiment the factor k is advantageously selected such that 100*k/2 renders an integer. According to an embodiment the factor k may be set to 2.56. Selecting k to 2.56 renders 100*k=256=2 raised to 8.

According to an embodiment the sampling frequency $f_S$ of the digital measurement data signal $S_{MD}$ may be fixed to a certain value $f_S$, such as e.g. $f_S=102$ kHz Hence, when the sampling frequency $f_S$ is fixed to a certain value $f_S$, the maximum frequency $f_{SEAmax}$ of the analogue signal $S_{EA}$ will be:

$$f_{SEAmax}=f_S/k$$

wherein $f_{SEAmax}$ is the highest frequency to be analyzed in the sampled signal Hence, when the sampling frequency $f_S$ is fixed to a certain value $f_S=102\ 400$ Hz, and the factor k is set to 2.56, the maximum frequency $f_{SEAmax}$ of the analogue signal $S_{EA}$ will be:

$$f_{SEAmax}=f_S/k=102\ 400/2.56=40\text{ kHz}$$

Accordingly, a digital measurement data signal $S_{MD}$, having a certain sampling frequency $f_S$, is generated in response to said received analogue measurement signal $S_{EA}$. The digital output 48 of the A/D converter 44 is coupled to the data processing means 50 via an output 49 of the sensor interface 40 so as to deliver the digital measurement data signal $S_{MD}$ to the data processing means 50.

The sensor unit 10 may comprise a vibration transducer, the sensor unit being structured to physically engage the connection coupling of the measuring point so that vibrations of the machine at the measuring point are transferred to the vibration transducer. According to an embodiment of the invention the sensor unit comprises a transducer having a piezoelectric element. When the measuring point 12 vibrates, the sensor unit 10, or at least a part of it, also vibrates and the transducer then produces an electrical signal of which the frequency and amplitude depend on the mechanical vibration frequency and the vibration amplitude of the measuring point 12, respectively. According to an embodiment of the invention the sensor unit 10 is a vibration sensor, providing an analogue amplitude signal of e.g. 10 mV/g in the Frequency Range 1.00 to 10000 Hz. Such a vibration sensor is designed to deliver substantially the same amplitude of 10 mV irrespective of whether it is exerted to the acceleration of 1 g (9.82 m/s$^2$) at 1 Hz, 3 Hz or 10 Hz. Hence, a typical vibration sensor has a linear response in a specified frequency range up to around 10 kHz. Mechanical vibrations in that frequency range emanating from rotating machine parts are usually caused by imbalance or misalignment. However, when mounted on a machine the linear response vibration sensor typically also has several different mechanical resonance frequencies dependent on the physical path between sensor and vibration source.

A damage in a roller bearing may cause relatively sharp elastic waves, known as shock pulses, travelling along a physical path in the housing of a machine before reaching the sensor. Such shock pulses often have a broad frequency spectrum. The amplitude of a roller bearing shock pulse is typically lower than the amplitude of a vibration caused by imbalance or misalignment.

Figure 2C:
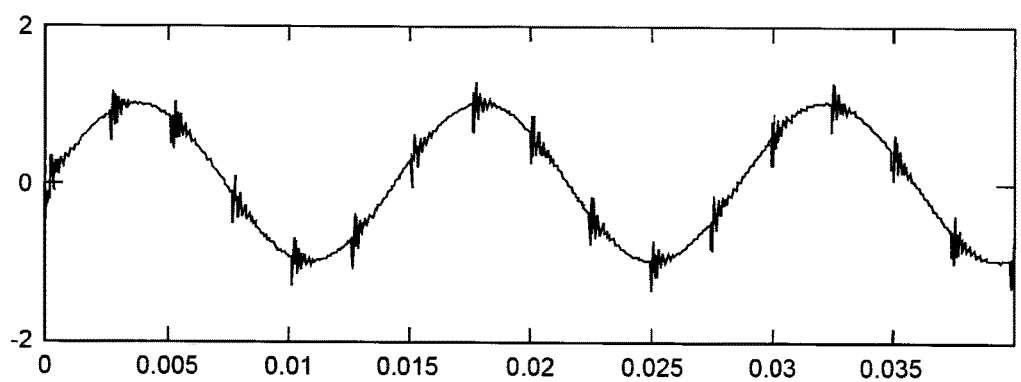
FIG. 2C is an illustration of a measuring signal from a vibration sensor.

The broad frequency spectrum of shock pulse signatures enables them to activate a "ringing response" or a resonance at a resonance frequency associated with the sensor. Hence, a typical measuring signal from a vibration sensor may have a wave form as shown in FIG. 2C, i.e. a dominant low frequency signal with a superimposed higher frequency lower amplitude resonant "ringing response".

In order to enable analysis of the shock pulse signature, often emanating from a bearing damage, the low frequency component must be filtered out. This can be achieved by means of a high pass filter or by means of a band pass filter. However, these filters must be adjusted such that the low frequency signal portion is blocked while the high frequency signal portion is passed on. An individual vibration sensor will typically have one resonance frequency associated with the physical path from one shock pulse signal source, and a different resonance frequency associated with the physical path from another shock pulse signal source, as mentioned in U.S. Pat. No. 6,053,047. Hence, filter adjustment aiming to pass the high frequency signal portion requires individual adaptation when a vibration sensor is used.

When such filter is correctly adjusted the resulting signal will consist of the shock pulse signature(s). However, the analysis of the shock pulse signature(s) emanating from a vibration sensor is somewhat impaired by the fact that the amplitude response as well as resonance frequency inherently varies dependent on the individual physical path from the shock pulse signal sources.

Advantageously, these drawbacks associated with vibration sensors may be alleviated by the use of a Shock Pulse Measurement sensor. The Shock Pulse Measurement sensor is designed and adapted to provide a pre-determined mechanical resonance frequency, as described in further detail below.

This feature of the Shock Pulse Measurement sensor advantageously renders repeatable measurement results in that the output signal from a Shock Pulse Measurement sensor has a stable resonance frequency substantially independent of the physical path between the shock pulse signal source and the shock pulse sensor. Moreover, mutually different individual shock pulse sensors provide a very small, if any, deviation in resonance frequency.

An advantageous effect of this is that signal processing is simplified, in that filters need not be individually adjusted, in contrast to the case described above when vibration sensors are used. Moreover, the amplitude response from shock pulse sensors is well defined such that an individual measurement provides reliable information when measurement is performed in accordance with appropriate measurement methods defined by S.P.M. Instrument AB.

Figure 2D:
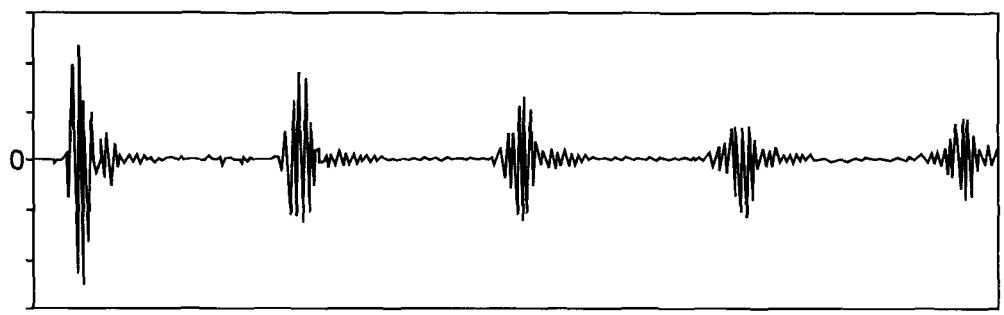
FIG. 2D illustrates a measuring signal amplitude generated by a shock pulse sensor.
Figure 2E:
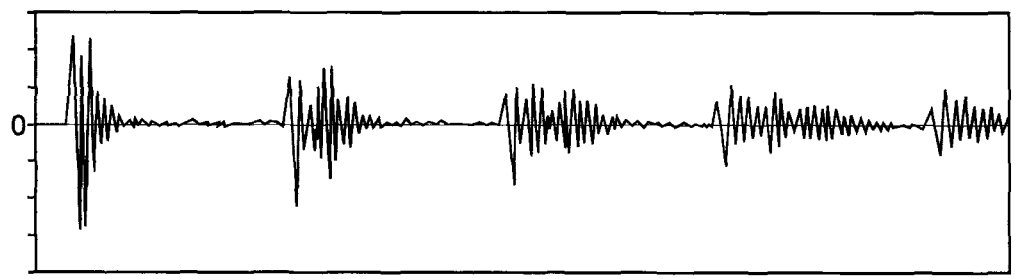
FIG. 2E illustrates a measuring signal amplitude generated by a vibration sensor.

FIG. 2D illustrates a measuring signal amplitude generated by a shock pulse sensor, and FIG. 2E illustrates a measuring signal amplitude generated by a vibration sensor. Both sensors have been exerted to the same series of mechanical shocks without the typical low frequency signal content. As clearly seen in FIGS. 2D and 2E, the duration of a resonance response to a shock pulse signature from the Shock Pulse Measurement sensor is shorter than the corresponding resonance response to a shock pulse signature from the vibration sensor.

This feature of the Shock Pulse Measurement sensor of providing distinct shock pulse signature responses has the advantageous effect of providing a measurement signal from which it is possible to distinguish between different mechanical shock pulses that occur within a short time span.

Figure 3:
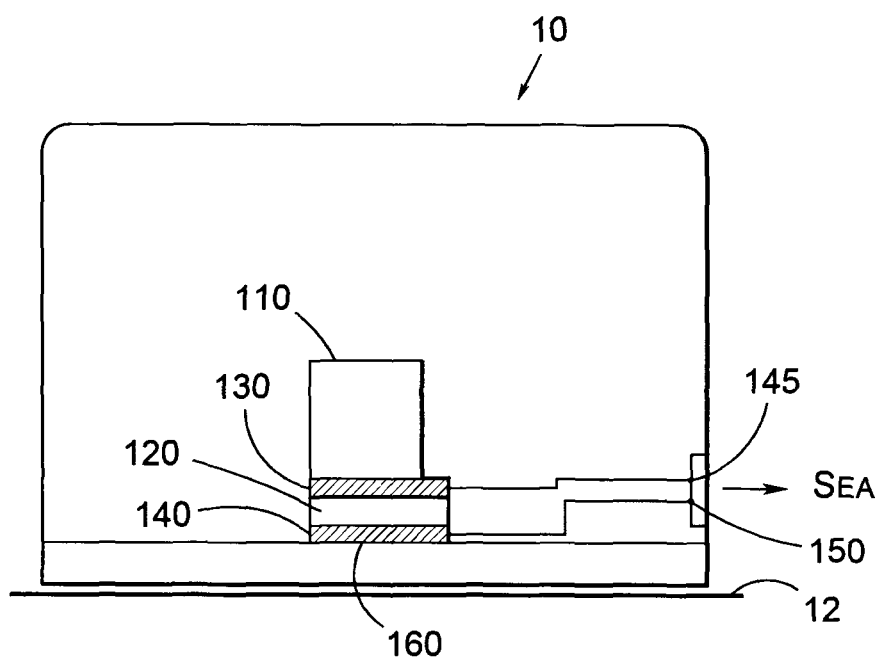
FIG. 3 is a simplified illustration of a Shock Pulse Measurement sensor according to an embodiment of the invention.

According to an embodiment of the invention the sensor is a Shock Pulse Measurement sensor. FIG. 3 is a simplified illustration of a Shock Pulse Measurement sensor 10 according to an embodiment of the invention. According to this embodiment the sensor comprises a part 110 having a certain mass or weight and a piezo-electrical element 120. The piezo-electrical element 120 is somewhat flexible so that it can contract and expand when exerted to external force. The piezo-electrical element 120 is provided with electrically conducting layers 130 and 140, respectively, on opposing surfaces. As the piezo-electrical element 120 contracts and expands it generates an electric signal which is picked up by the conducting layers 130 and 140. Accordingly, a mechanical vibration is transformed into an analogue electrical measurement signal $S_{EA}$, which is delivered on output terminals 145, 150.

The piezo-electrical element 120 may be positioned between the weight 110 and a surface 160 which, during operation, is physically attached to the measuring point 12, as illustrated in FIG. 3.

The Shock Pulse Measurement sensor 10 has a resonance frequency that depends on the mechanical characteristics for the sensor, such as the mass m of weight part 110 and the resilience of piezo-electrical element 120. Hence, the piezo-electrical element has an elasticity and a spring constant k. The mechanical resonance frequency $f_{RM}$ for the sensor is therefore also dependent on the mass m and the spring constant k.

According to an embodiment of the invention the mechanical resonance frequency $f_{RM}$ for the sensor can be determined by the equation following equation:

$$f_{RM} = 1/(2\pi)\sqrt{(k/m)} \quad (eq\ 1)$$

According to another embodiment the actual mechanical resonance frequency for a Shock Pulse Measurement sensor 10 may also depend on other factors, such as the nature of the attachment of the sensor 10 to the body of the machine 6.

The resonant Shock Pulse Measurement sensor 10 is thereby particularly sensitive to vibrations having a frequency on or near the mechanical resonance frequency $f_{RM}$. The Shock Pulse Measurement sensor 10 may be designed so that the mechanical resonance frequency $f_{RM}$ is somewhere in the range from 28 kHz to 37 kHz. According to another embodiment the mechanical resonance frequency $f_{RM}$ is somewhere in the range from 30 kHz to 35 kHz.

Accordingly the analogue electrical measurement signal has an electrical amplitude which may vary over the frequency spectrum. For the purpose of describing the theoretical background, it may be assumed that if the Shock Pulse Measurement sensor 10 were exerted to mechanical vibrations with identical amplitude in all frequencies from e.g. 1 Hz to e.g. 200 000 kHz, then the amplitude of the analogue signal $S_{EA}$ from the Shock Pulse Measurement Sensor will have a maximum at the mechanical resonance frequency $f_{RM}$, since the sensor will resonate when being "pushed" with that frequency.

With reference to FIG. 2B, the conditioning circuit 43 receives the analogue signal $S_{EA}$. The conditioning circuit 43 may be designed to be an impedance adaption circuit designed to adapt the input impedance of the A/D-converter as seen from the sensor terminals 145,150 so that an optimum signal transfer will occur. Hence, the conditioning circuit 43 may operate to adapt the input impedance $Z_{in}$ as seen from the sensor terminals 145,150 so that a maximum electric power is delivered to the A/D-converter 44. According to an embodiment of the conditioning circuit 43 the analogue signal $S_{EA}$ is fed to the primary winding of a transformer, and a conditioned analogue signal is delivered by a secondary winding of the transformer. The primary winding has n1 turns and the secondary winding has n2 turns, the ratio $n1/n2=n_{12}$. Hence, the A/D converter 44 is coupled to receive the conditioned analogue signal from the conditioning circuit 43. The A/D converter 44 has an input impedance $Z_{44}$, and the input impedance of the A/D-converter as seen from the sensor terminals 145,150 will be $(n1/n2)^2 * Z_{44}$, when the conditioning circuit 43 is coupled in between the sensor terminals 145,150 and the input terminals of the A/D converter 44.

The A/D converter 44 samples the received conditioned analogue signal with a certain sampling frequency $f_S$ so as to deliver a digital measurement data signal $S_{MD}$ having said certain sampling frequency $f_S$ and wherein the amplitude of each sample depends on the amplitude of the received analogue signal at the moment of sampling.

Figure 5:
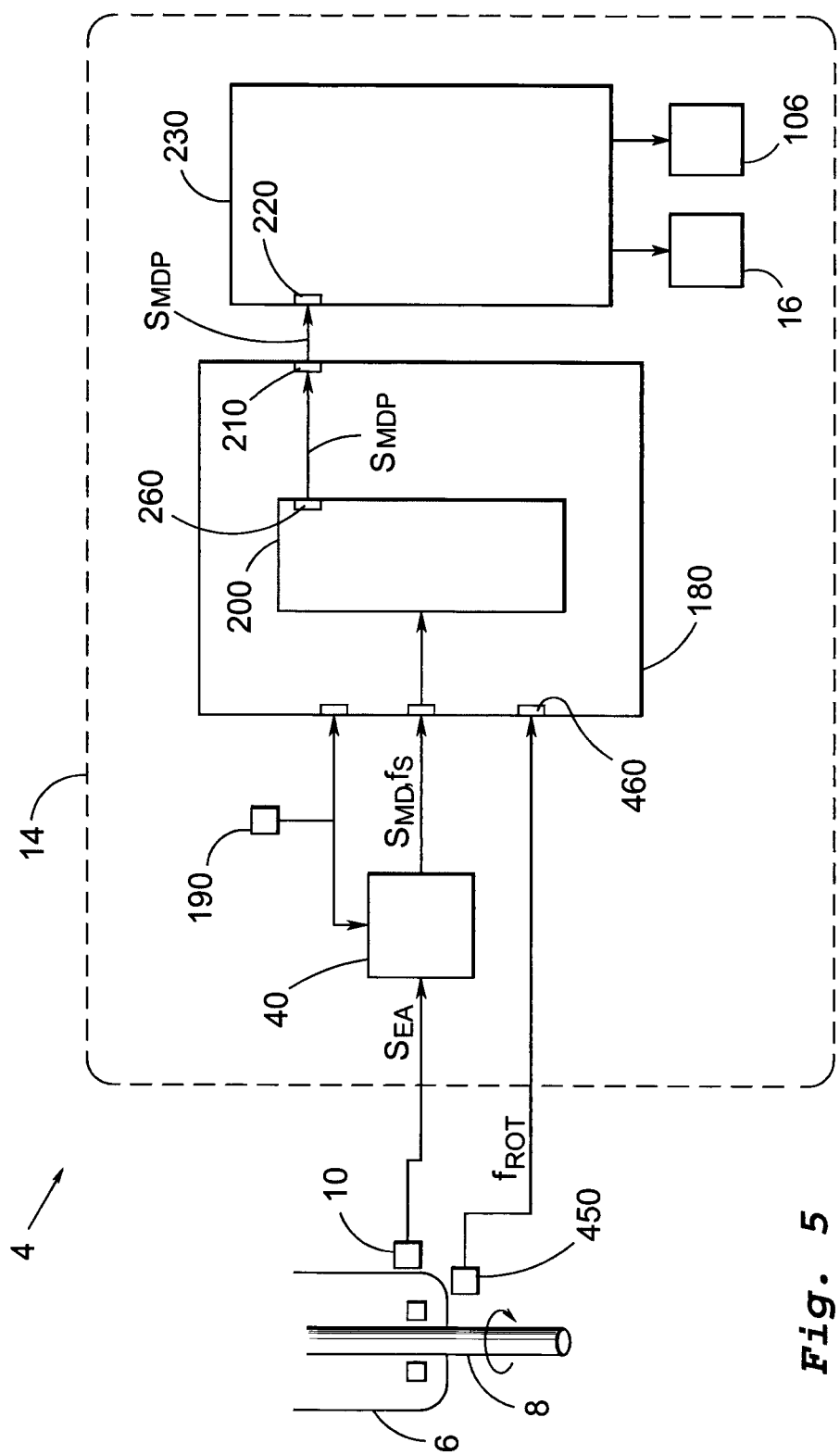
FIG. 5 is a schematic block diagram of an embodiment of the analysis apparatus at a client location with a machine 6 having a movable shaft.

According to embodiments of the invention the digital measurement data signal $S_{MD}$ is delivered to a means 180 for digital signal processing (See FIG. 5).

According to an embodiment of the invention the means 180 for digital signal processing comprises the data processor 50 and program code for causing the data processor 50 to perform digital signal processing. According to an embodiment of the invention the processor 50 is embodied by a Digital Signal Processor. The Digital Signal Processor may also be referred to as a DSP.

Figure 4:
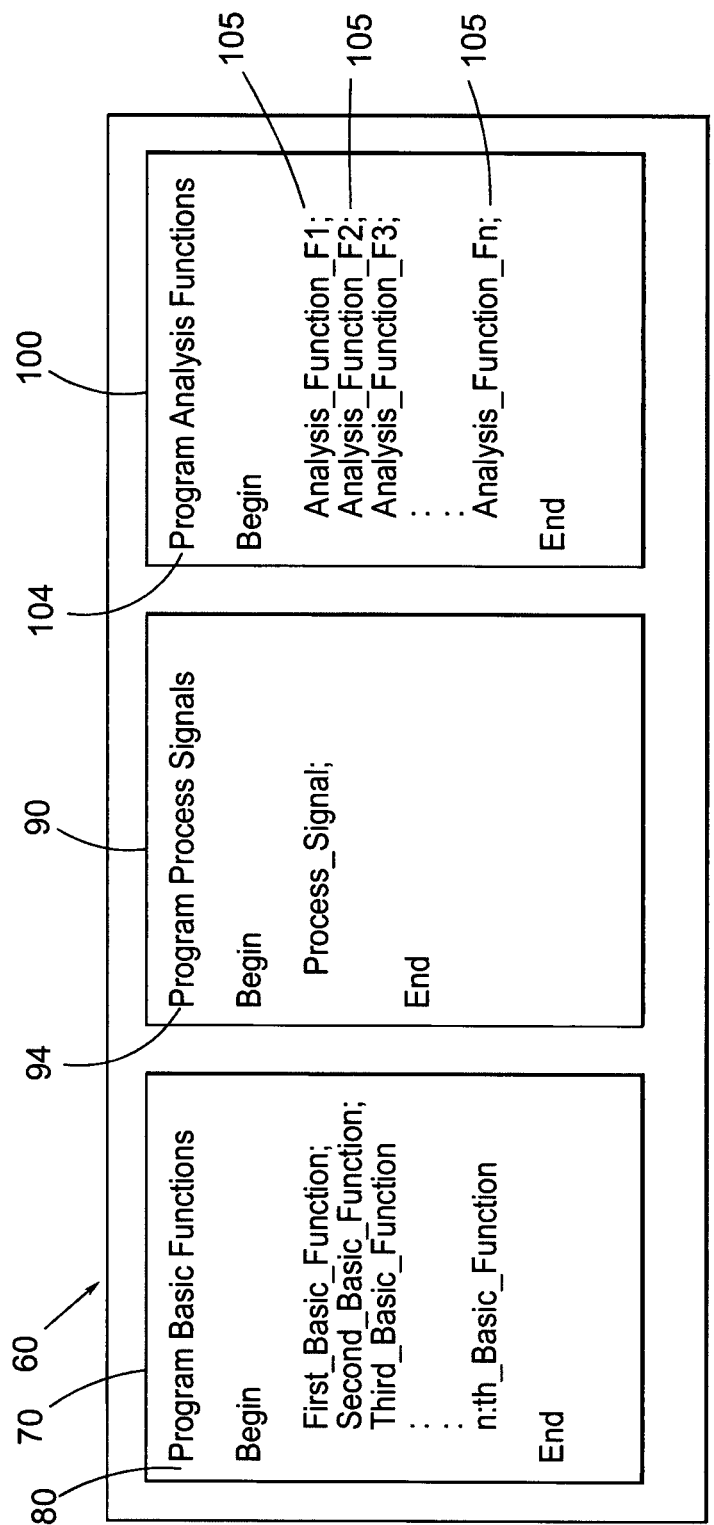
FIG. 4 is a simplified illustration of an embodiment of the memory 60 and its contents.

With reference to FIG. 2A, the data processing means 50 is coupled to a memory 60 for storing said program code. The program memory 60 is preferably a non-volatile memory. The memory 60 may be a read/write memory, i.e. enabling both reading data from the memory and writing new data onto the memory 60. According to an embodiment the program memory 60 is embodied by a FLASH memory. The program memory 60 may comprise a first memory segment 70 for storing a first set of program code 80 which is executable so as to control the analysis apparatus 14 to perform basic operations (FIG. 2A and FIG. 4). The program memory may also comprise a second memory segment 90 for storing a second set of program code 94. The second set of program code 94 in the second memory segment 90 may include program code for causing the analysis apparatus to process the detected signal, or signals, so as to generate a pre-processed signal or a set of pre-processed signals. The memory 60 may also include a third memory segment 100 for storing a third set of program code 104. The set of program code 104 in the third memory segment 100 may include program code for causing the analysis apparatus to perform a selected analysis function 105. When an analysis function is executed it may cause the analysis apparatus to present a corresponding analysis result on user interface 106 or to deliver the analysis result on port 16 (See FIG. 1 and FIG. 2A and FIG. 7).

The data processing means 50 is also coupled to a read/write memory 52 for data storage. Moreover, the data processing means 50 may be coupled to an analysis apparatus communications interface 54. The analysis apparatus communications interface 54 provides for bi-directional communication with a measuring point communication interface 56 which is attachable on, at or in the vicinity of the measuring point on the machine.

The measuring point 12 may comprise a connection coupling 32, a readable and writeable information carrier 58, and a measuring point communication interface 56.

The writeable information carrier 58, and the measuring point communication interface 56 may be provided in a separate device 59 placed in the vicinity of the stud 30, as illustrated in FIG. 2. Alternatively the writeable information carrier 58, and the measuring point communication interface 56 may be provided within the stud 30. This is described in more detail in WO 98/01831, the content of which is hereby incorporated by reference.

The system 2 is arranged to allow bidirectional communication between the measuring point communication interface 56 and the analysis apparatus communication interface 54. The measuring point communication interface 56 and the analysis apparatus communication interface 54 are preferably constructed to allow wireless communication. According to an embodiment the measuring point communication interface and the analysis apparatus communication interface are constructed to communicate with one another by radio frequency (RF) signals. This embodiment includes an antenna in the measuring point communication interface 56 and another antenna the analysis apparatus communication interface 54.

FIG. 4 is a simplified illustration of an embodiment of the memory 60 and its contents. The simplified illustration is intended to convey understanding of the general idea of storing different program functions in memory 60, and it is not necessarily a correct technical teaching of the way in which a program would be stored in a real memory circuit. The first memory segment 70 stores program code for controlling the analysis apparatus 14 to perform basic operations. Although the simplified illustration of FIG. 4 shows pseudo code, it is to be understood that the program code 80 may be constituted by machine code, or any level program code that can be executed or interpreted by the data processing means 50 (FIG. 2A).

The second memory segment 90, illustrated in FIG. 4, stores a second set of program code 94. The program code 94 in segment 90, when run on the data processing means 50, will cause the analysis apparatus 14 to perform a function, such as a digital signal processing function. The function may comprise an advanced mathematical processing of the digital measurement data signal $S_{MD}$. According to embodiments of the invention the program code 94 is adapted to cause the processor means 50 to perform signal processing functions described in connection with FIGS. 5, 6, 9, 10, 11A, 11B, 12A, 12B, 13A-C, 14A, 14B, 15A and/or FIG. 16 in this document.

As mentioned above in connection with FIG. 1, a computer program for controlling the function of the analysis apparatus may be downloaded from the server computer 20. This means that the program-to-be-downloaded is transmitted to over the communications network 18. This can be done by modulating a carrier wave to carry the program over the communications network 18. Accordingly the downloaded program may be loaded into a digital memory, such as memory 60 (See FIGS. 2A and 4). Hence, a signal processing program 94 and or an analysis function program 104, 105 may be received via a communications port, such as port 16 (FIGS. 1 & 2A), so as to load it into memory 60. Similarly, a signal processing program 94 and or an analysis function program 104, 105 may be received via communications port 29B (FIG. 1), so as to load it into a program memory location in computer 26B or in database 22B.

An aspect of the invention relates to a computer program product, such as a program code means 94 and/or program code means 104, 105 loadable into a digital memory of an apparatus. The computer program product comprising software code portions for performing signal processing methods and/or analysis functions when said product is run on a data processing unit 50 of an apparatus for analysing the condition of a machine. The term "run on a data processing unit" means that the computer program plus the data processing unit carries out a method of the kind described in this document.

The wording "a computer program product, loadable into a digital memory of a condition analysing apparatus" means that a computer program can be introduced into a digital memory of a condition analysing apparatus so as achieve a condition analysing apparatus programmed to be capable of, or adapted to, carrying out a method of the kind described above. The term "loaded into a digital memory of a condition analysing apparatus" means that the condition analysing apparatus programmed in this way is capable of, or adapted to, carrying out a method of the kind described above.

The above mentioned computer program product may also be loadable onto a computer readable medium, such as a compact disc or DVD. Such a computer readable medium may be used for delivery of the program to a client.

According to an embodiment of the analysis apparatus 14 (FIG. 2A), it comprises a user input interface 102, whereby an operator may interact with the analysis apparatus 14. According to an embodiment the user input interface 102 comprises a set of buttons 104. An embodiment of the analysis apparatus 14 comprises a user output interface 106. The user output interface may comprise a display unit 106. The data processing means 50, when it runs a basic program function provided in the basic program code 80, provides for user interaction by means of the user input interface 102 and the display unit 106. The set of buttons 104 may be limited to a few buttons, such as for example five buttons, as illustrated in FIG. 2A. A central button 107 may be used for an ENTER or SELECT function, whereas other, more peripheral buttons may be used for moving a cursor on the display 106. In this manner it is to be understood that symbols and text may be entered into the apparatus 14 via the user interface. The display unit 106 may, for example, display a number of symbols, such as the letters of alphabet, while the cursor is movable on the display in response to user input so as to allow the user to input information.

FIG. 5 is a schematic block diagram of an embodiment of the analysis apparatus 14 at a client location 4 with a machine 6 having a movable shaft 8. The sensor 10, which may be a Shock Pulse Measurement Sensor, is shown attached to the body of the machine 6 so as to pick up mechanical vibrations and so as to deliver an analogue measurement signal $S_{EA}$ indicative of the detected mechanical vibrations to the sensor interface 40. The sensor interface 40 may be designed as described in connection with FIG. 2A or 2B. The sensor interface 40 delivers a digital measurement data signal $S_{MD}$ to a means 180 for digital signal processing.

The digital measurement data signal $S_{MD}$ has a sampling frequency $f_S$, and the amplitude value of each sample depends on the amplitude of the received analogue measurement signal $S_{EA}$ at the moment of sampling. According to an embodiment the sampling frequency $f_S$ of the digital measurement data signal $S_{MD}$ may be fixed to a certain value $f_S$, such as e.g. $f_S$=102 400 Hz. The sampling frequency $f_S$ may be controlled by a clock signal delivered by a clock 190, as illustrated in FIG. 5. The clock signal may also be delivered to the means 180 for digital signal processing. The means 180 for digital signal processing can produce information about the temporal duration of the received digital measurement data signal $S_{MD}$ in response to the received digital measurement data signal $S_{MD}$, the clock signal and the relation between the sampling frequency $f_S$ and the clock signal, since the duration between two consecutive sample values equals $T_S=1/f_S$.

According to embodiments of the invention the means 180 for digital signal processing includes a pre-processor 200 for performing a pre-processing of the digital measurement data signal $S_{MD}$ so as to deliver a pre-processed digital signal $S_{MDP}$ on an output 210. The output 210 is coupled to an input 220 of an evaluator 230. The evaluator 230 is adapted to evaluate the pre-processed digital signal $S_{MDP}$ so as to deliver a result of the evaluation to a user interface 106. Alternatively the result of the evaluation may be delivered to a communication port 16 so as to enable the transmission of the result e.g. to a control computer 33 at a control site 31 (See FIG. 1).

According to an embodiment of the invention, the functions described in connection with the functional blocks in means 180 for digital signal processing, pre-processor 200 and evaluator 230 may be embodied by computer program code 94 and/or 104 as described in connection with memory blocks 90 and 100 in connection with FIG. 4 above.

A user may require only a few basic monitoring functions for detection of whether the condition of a machine is normal or abnormal. On detecting an abnormal condition, the user may call for specialized professional maintenance personnel to establish the exact nature of the problem, and for performing the necessary maintenance work. The professional maintenance personnel frequently needs and uses a broad range of evaluation functions making it possible to establish the nature of, and/or cause for, an abnormal machine condition. Hence, different users of an analysis apparatus 14 may pose very different demands on the function of the apparatus. The term Condition Monitoring function is used in this document for a function for detection of whether the condition of a machine is normal or somewhat deteriorated or abnormal. The term Condition Monitoring function also comprises an evaluation function making it possible to establish the nature of, and/or cause for, an abnormal machine condition.

Examples of Machine Condition Monitoring Functions

The condition monitoring functions F1, F2 ... Fn includes functions such as: vibration analysis, shock pulse measuring, Peak level analysis, spectrum analysis of shock pulse measurement data, Fast Fourier Transformation of vibration measurement data, graphical presentation of condition data on a user interface, storage of condition data in a writeable information carrier on said machine, storage of condition data in a writeable information carrier in said apparatus, tachometering, imbalance detection, and misalignment detection.

According to an embodiment the apparatus 14 includes the following functions:
F1=vibration analysis;
F2=shock pulse measuring,
F3=Peak level analysis
F4=spectrum analysis of shock pulse measurement data,
F5=Fast Fourier Transformation of vibration measurement data,
F6=graphical presentation of condition data on a user interface,
F7=storage of condition data in a writeable information carrier on said machine,
F8=storage of condition data in a writeable information carrier 52 in said apparatus,
F9=tachometering,
F10=imbalance detection, and
F11=misalignment detection.
F12=Retrieval of condition data from a writeable information carrier 58 on said machine.
F13=Performing Peak level analysis F3 and performing function F12 "Retrieval of condition data from a writeable information carrier 58 on said machine" so as to enable a comparison or trending based on current Peak level data and historical Peak level data.
F14=Retrieval of identification data from a writeable information carrier 58 on said machine.

Embodiments of the function F7 "storage of condition data in a writeable information carrier on said machine", and F13 vibration analysis and retrieval of condition data is described in more detail in WO 98/01831, the content of which is hereby incorporated by reference.

The peak level analysis F3 may be performed on the basis of the enveloped time domain signal $S_{ENV}$ delivered by the enveloper 250. The signal $S_{ENV}$ is also referred to as $S_{MDP}$ The peak level analysis F3 is adapted to monitor the signal for the duration of a peak monitoring period $T_{PM}$ for the purpose of establishing the maximum amplitude level.

The peak amplitude may be indicative of Oil film thickness in a monitored bearing. Hence, the detected peak amplitude may be indicative of separation between the metal surfaces in the rolling interface. The oil film thickness may depend on lubricant supply and/or on alignment of the shaft. Moreover, the oil film thickness may depend on the load on the shaft, i.e. on the force with which metal surfaces are pressed together, the metal surfaces being e.g. that of a bearing and that of a shaft.

The actual detected value of the maximum amplitude level may also depend on the mechanical state of the bearing surfaces, i.e the condition of the bearing assembly. Accordingly, the detected value of the maximum amplitude level may depend on roughness of the metal surfaces in the rolling interface, and/or damage to a metal surface in the rolling interface. The detected value of the maximum amplitude level may also depend on the occurrence of a loose particle in the bearing assembly.

Figure 6A:
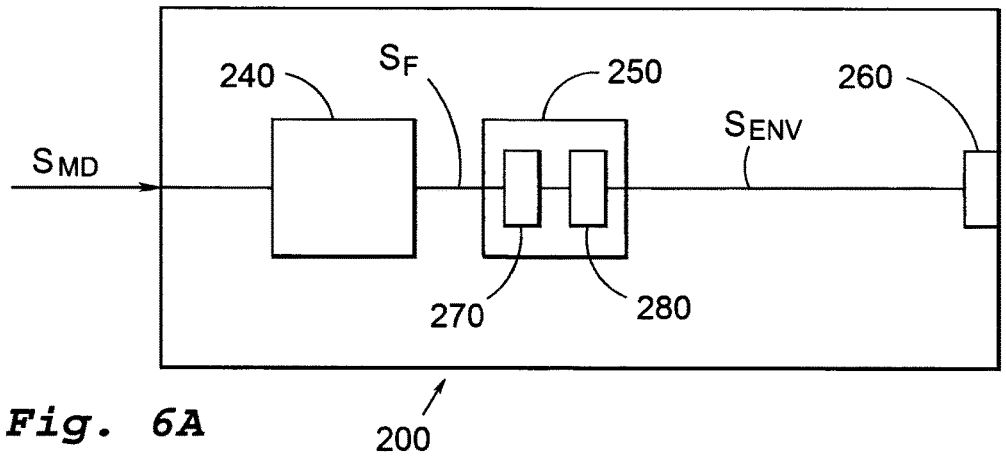
FIG. 6A illustrates a schematic block diagram of an embodiment of the pre-processor according to an embodiment of the present invention.

FIG. 6A illustrates a schematic block diagram of an embodiment of the pre-processor 200 according to an embodiment of the present invention. In this embodiment the digital measurement data signal $S_{MD}$ is coupled to a digital band pass filter 240 having a lower cutoff frequency $f_{LC}$, an upper cutoff frequency $f_{UC}$ and passband bandwidth between the upper and lower cutoff frequencies.

The output from the digital band pass filter 240 is connected to a digital enveloper 250. According to an embodiment of the invention the signal output from the enveloper 250 is delivered to an output 260. The output 260 of the pre-processor 200 is coupled to output 210 of digital signal processing means 180 for delivery to the input 220 of evaluator 230.

The upper and lower cutoff frequencies of the digital band pass filter 240 may selected so that the frequency components of the signal $S_{MD}$ at the resonance frequency $f_{RM}$ for the sensor are in the passband bandwidth. As mentioned above, an amplification of the mechanical vibration is achieved by the sensor being mechanically resonant at the resonance frequency $f_{RM}$. Accordingly the analogue measurement signal $S_{EA}$ reflects an amplified value of the vibrations at and around the resonance frequency $f_{RM}$. Hence, the band pass filter according to the FIG. 6 embodiment advantageously suppresses the signal at frequencies below and above resonance frequency $f_{RM}$, so as to further enhance the components of the measurement signal at the resonance frequency $f_{RM}$. Moreover, the digital band pass filter 240 advantageously further reduces noise inherently included in the measurement signal, since any noise components below the lower cutoff frequency $f_{LC}$, and above upper cutoff frequency $f_{UC}$ are also eliminated or reduced. Hence, when using a resonant Shock Pulse Measurement sensor 10 having a mechanical resonance frequency $f_{RM}$ in a range from a lowest resonance frequency value $f_{RML}$ to a highest resonance frequency value $f_{RMU}$ the digital band pass filter 240 may be designed to having a lower cutoff frequency $f_{LC}=f_{RML}$, and an upper cutoff frequency $f_{UC}=f_{RMU}$. According to an embodiment the lower cutoff frequency $f_{LC}=f_{RML}=28$ kHz, and the upper cutoff frequency $f_{UC}=f_{RMU}=37$ kHz.

According to another embodiment the mechanical resonance frequency $f_{RM}$ is somewhere in the range from 30 kHz to 35 kHz, and the digital band pass filter 240 may then be designed to having a lower cutoff frequency $f_{LC}$=30 kHz and an upper cutoff frequency $f_{UC}$=35 kHz.

According to another embodiment the digital band pass filter 240 may be designed to have a lower cutoff frequency $f_{LC}$ being lower than the lowest resonance frequency value $f_{RML}$, and an upper cutoff frequency $f_{UC}$ being higher than the highest resonance frequency value $f_{RMU}$. For example the mechanical resonance frequency $f_{RM}$ may be a frequency in the range from 30 kHz to 35 kHz, and the digital band pass filter 240 may then be designed to having a lower cutoff frequency $f_{LC}$=17 kHz, and an upper cutoff frequency $f_{UC}$=36 kHz.

Accordingly, the digital band pass filter 240 may deliver a passband digital measurement data signal $S_F$ having an advantageously low out-of-band noise content and reflecting mechanical vibrations in the passband. The passband digital measurement data signal $S_F$ may be delivered to an enveloper 250.

The digital enveloper 250 accordingly receives the passband digital measurement data signal $S_F$ which may reflect a signal having positive as well as negative amplitudes. With reference to FIG. 6A, the received signal is rectified by a digital rectifier 270, and the rectified signal may be filtered by an optional low pass filter 280 so as to produce a digital envelop signal $S_{ENV}$.

Accordingly, the signal $S_{ENV}$ is a digital representation of an envelope signal being produced in response to the filtered measurement data signal $S_F$. According to some embodiments of the invention the optional low pass filter 280 may be eliminated.

According to the FIG. 6A embodiment of the invention the signal $S_{ENV}$ is delivered to the output 260 of pre-processor 200. Hence, according to an embodiment of the invention the pre-processed digital signal $S_{MDP}$ delivered on the output 210 (FIG. 5) is the digital envelop signal $S_{ENV}$.

Whereas prior art analogue devices for generating an envelop signal in response to a measurement signal employs an analogue rectifier which inherently leads to a biasing error being introduced in the resulting signal, the digital enveloper 250 will advantageously produce a true rectification without any biasing errors. Accordingly, the digital envelop signal $S_{ENV}$ will have a good Signal-to-Noise Ratio, since the sensor being mechanically resonant at the resonance frequency in the passband of the digital band pass filter 240 leads to a high signal amplitude and the signal processing being performed in the digital domain eliminates addition of noise and eliminates addition of biasing errors.

With reference to FIG. 5 the pre-processed digital signal $S_{MDP}$ is delivered to input 220 of the evaluator 230.

According to another embodiment, the filter 240 is a high pass filter having a cut-off frequency $f_{LC}$. This embodiment simplifies the design by replacing the band-pass filter with a high-pass filter 240, thereby leaving the low pass filtering to another low pass filter downstream, such as the low pass filter 280. The cut-off frequency $f_{LC}$ of the high pass filter 240 is selected to approximately the value of the lowest expected mechanical resonance frequency value $f_{RMU}$ of the resonant Shock Pulse Measurement sensor 10. When the mechanical resonance frequency $f_{RM}$ is somewhere in the range from 30 kHz to 35 kHz, the high pass filter 240 may be designed to having a lower cutoff frequency $f_{LC}$=30 kHz. The high-pass filtered signal is then passed to the rectifier 270 and on to the low pass filter 280.

According to an embodiment it should be possible to use sensors 10 having a resonance frequency somewhere in the range from 20 kHz to 35 kHz. In order to achieve this, the high pass filter 240 may be designed to having a lower cutoff frequency $f_{LC}$=20 kHz.

Figure 6B:
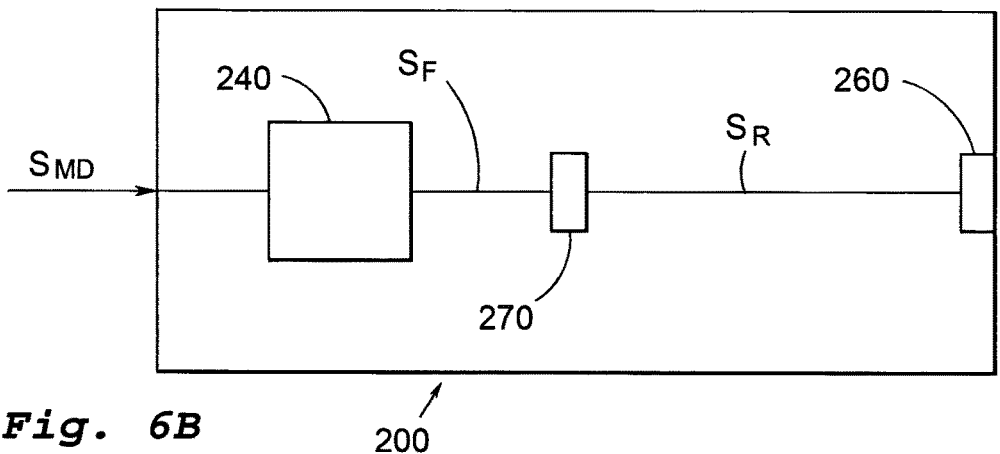
FIG. 6B illustrates an embodiment of the pre-processor including a digital rectifier.
Figure 7:
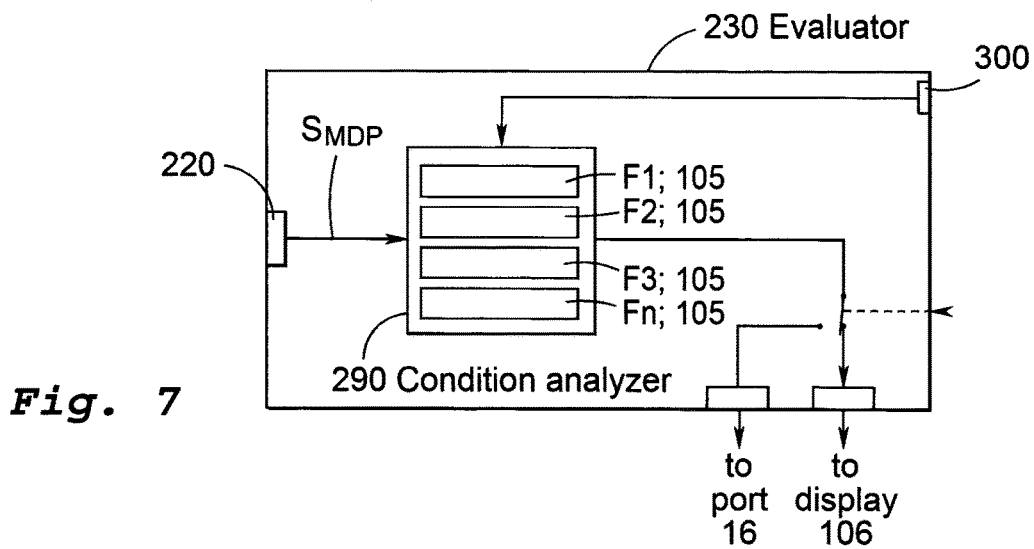
FIG. 7 illustrates an embodiment of the evaluator.

FIG. 6B illustrates an embodiment according to which the digital band pass filter 240 delivers the filtered signal $S_F$ to the digital rectifier 270, and the rectifier 270 delivers the rectified signal $S_R$ directly to a condition analyzer 290 (See FIG. 7 in conjunction with FIG. 6B).

FIG. 7 illustrates an embodiment of the evaluator 230 (See also FIG. 5). The FIG. 7 embodiment of the evaluator 230 includes the condition analyser 290 adapted to receive a pre-processed digital signal $S_{MDP}$ indicative of the condition of the machine 6. The condition analyser 290 can be controlled to perform a selected condition analysis function 105 by means of a selection signal delivered on a control input 300. Examples of condition analysis functions 105 are schematically illustrated as boxes in FIG. 7. The selection signal delivered on control input 300 may be generated by means of user interaction with the user interface 102 (See FIG. 2A).

As mentioned above, the analysis apparatus 14 may include a Peak level analysis function F3, 105 (See FIG. 4 & FIG. 7).

According to an embodiment of the invention the Peak level analysis function may be performed by the condition analyser 290 in response to activation via control input 300. In response to the peak level analysis activation signal, the analyzer 290 will activate a peak level analyzer F3, 310 (See FIG. 7), and the digital measurement signal SMDP will be passed to an input of the peak level analyzer F3, 310. The peak level analyzer F3, 310 is adapted to monitor the signal for the duration of a peak monitoring time $T_{PM}$ for the purpose of establishing a maximum amplitude level $A_{PR}$ indicative of the mechanical state of the monitored part, i.e. bearings 7 and/or shaft 8. The maximum amplitude level $A_{PR}$ may also be referred to as representative peak amplitude $A_{PR}$.

As mentioned above, the peak amplitude detected in the measurement signal may, when the peak amplitude value originates from a mechanical vibration in the monitored machine, be indicative of the condition of the machine. When a bearing assembly is monitored, the peak amplitude value may be indicative of the condition of the bearing assembly. In fact, the peak amplitude value may be indicative of Oil film thickness in a monitored bearing. Hence, the detected peak amplitude may be indicative of separation between the metal surfaces in the rolling interface. The oil film thickness may depend on lubricant supply and/or on alignment of the shaft. Moreover, the oil film thickness may depend on the load on the shaft, i.e. on the force with which metal surfaces are pressed together, the metal surfaces being e.g. that of a bearing and that of a shaft. The actual detected value of the maximum amplitude level may also depend on the mechanical state of the bearing surfaces.

However, the ability to correctly indicate the condition of the rotational part based on a detected peak amplitude value requires that the detected peak amplitude value really does originate from the rotational part. Machines in an industry, such as a e.g. a paper mill may be exerted to mechanical impacts from tools or other machinery, which may cause mechanical vibrations or shock waves in the monitored machine. Hence, a peak amplitude level in the digital measurement signal may be caused by the environment of the machine, in which case the actual highest amplitude value detected in the digital measurement signal may have nothing to do with the condition of the monitored machine part 8. For the purpose of this document, such peak amplitude levels in the digital measurement signal that do not depend on the mechanical state of the monitored part 8 are regarded as noise. Moreover, electrical fields in the environment of the sensor or in the vicinity of conductors of the condition analysis system may interfere to give rise to peak voltage amplitudes in the measuring signal. Such peak voltage amplitudes may also be regarded as noise.

The inventor realized that there is a particularly high noise level in the mechanical vibrations of certain machinery, and that such noise levels hamper the detection of machine damages. Hence, for some types of machinery, conventional methods for preventive condition monitoring have failed to provide sufficiently early and/or reliable warning of oncoming deteriorating conditions. The inventor concluded that there may exist a mechanical vibration $V_{MD}$ indicative of a deteriorated condition in such machinery, but that conventional methods for correctly detecting such a vibration may hitherto have been inadequate.

The inventor also realized that machines having slowly rotating parts were among the types of machinery for which conventional methods for preventive condition monitoring have failed to provide sufficiently reliable warning of oncoming deteriorating conditions.

Having realized that a particularly high noise level in the mechanical vibrations of certain machinery hampers the detection of machine damages, the inventor came up with a method for enabling a more reliable detection of a signal peak amplitude level which is indicative of an incipient damage of a rotational part 8 of the monitored machine 6.

However, tests have indicated that, even in a laboratory environment where there is very little or no noise, the detected peak level for a rotational part often varies, i.e. each revolution of a rotational shaft does not produce identical peak levels. After careful study of such amplitude levels the inventor concluded that the amplitude levels emanating from rotation of a monitored rotational part closely follow the normal distribution, also referred to as the Gaussian distribution; and that it is necessary to record the amplitude levels originating from plural revolutions of a rotational part in order to detect a relevant true peak value which may be used for accurate determination of the condition of the monitored rotational part.

In this context, it should be noted that the normal distribution is a probability distribution that describes data that cluster around the mean. The graph of the associated probability density function is bell-shaped, with a peak at the mean, and is known as the Gaussian function or bell curve.

Figure 8:
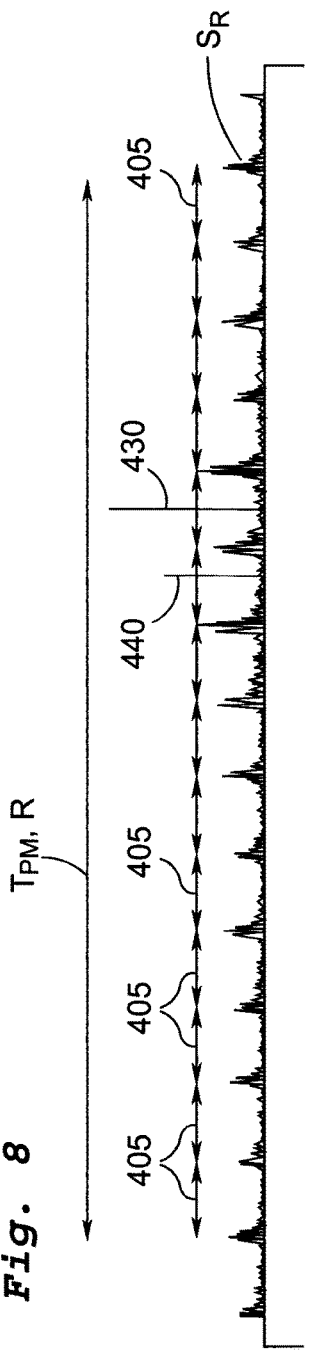
FIG. 8 is a schematic illustration of a rectified signal that could be delivered by the rectifier shown in FIG. 6B.

FIG. 8 is a schematic illustration of a rectified signal $S_R$ that could be delivered by rectifier 270 (FIG. 68) to peak analyzer F3, 310 (FIG. 7). FIG. 5 in conjunction with FIG. 68 and FIG. 7 provide an overview of an embodiment of the analysis apparatus. The peak level analysis F3 (See FIG. 7 & FIG. 4) is adapted to monitor the signal for the duration of a peak monitoring period $T_{PM}$ for the purpose of establishing a relevant maximum amplitude level. In the example illustrated in FIG. 8 the monitoring period $T_{PM}$ corresponds to 14 revolutions of the monitored rotational part. Single revolutions of the monitored rotational part are indicated by reference 405 in FIG. 8.

Accordingly, by defining the monitoring period $T_{PM}$ in terms of a number of revolutions of the rotational part to be monitored, rather than in terms of a certain time period, the quality of the analysis in improved. More precisely, the inventor realized that when the number of detected peak values $A_P$ is seen in relation to the amount R of revolution of the monitored rotatable part during the measurement, statistical methods may be employed so as to achieve an increased quality of the resulting peak amplitude value.

The inventor realized that if the distribution of detected peak amplitude values $A_P$ resembles the Gaussian distribution it could be concluded that one revolution of a shaft may result in a different set of peak amplitude values than another revolution of the same shaft.

An embodiment of the method comprises the steps of:
receiving a first digital signal dependent on mechanical vibrations emanating from rotation of said part;
analysing said first digital signal so as to detect peak amplitude values Ap during a finite time period $T_{PM}$, said finite time period corresponding to a certain amount R of revolution of said rotatable part. The certain amount R of revolution should correspond to more than one revolution of said monitored rotatable part. The method further comprises
defining a plurality $N_R$ of amplitude ranges $R_A$;
sorting said detected peak amplitude values Ap into corresponding amplitude ranges $R_A$ so as to reflect occurrence N of detected peak amplitude values Ap within said plurality of amplitude ranges.

Figure 9:
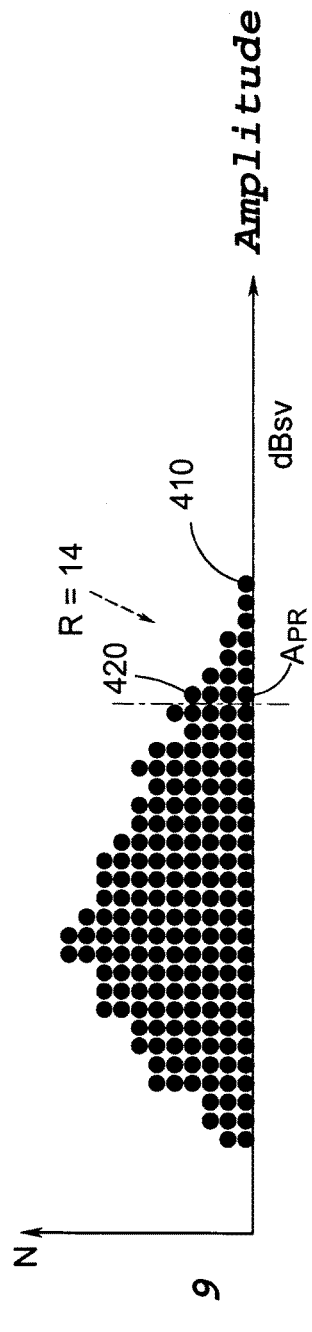
FIG. 9 illustrates a histogram resulting from a measurement in without any noise.

FIG. 9 illustrates a histogram resulting from a measurement wherein the measuring time period $T_{PM}$ corresponded to fourteen (R=14) revolutions of the monitored rotatable part under laboratory conditions without any noise, i.e. each one of the illustrated black dots corresponds to one detected peak amplitude value A. Hence, the "certain amount of revolution" is R=14.0 revolutions, and the finite time period $T_{PM}$ was the time it took for the monitored part 8 to revolve 14 revolutions. The monitored part 8 may be a shaft. Hence, according to embodiments of the invention the measuring time period $T_{PM}$ may depend on the speed of rotation of the rotatable part so that when the monitored rotational part rotates at slower speed the measuring time period $T_{PM}$ will be longer, and when the monitored rotational part rotates at higher speed the measuring time period $T_{PM}$ will be shorter.

Based on the knowledge that the measurement was made during R=14 full revolutions of the monitored part, and assuming that a highest peak amplitude value is detected once per revolution, it can be seen from FIG. 9 that the top fourteen (14) detected amplitude values do vary a bit, the highest amplitude being indicated by reference 410 and the 14$^{th}$ highest amplitude range being indicated by reference 420. Hence, from FIG. 9 it may be deduced that the peak amplitude value $A_P$ detected during one revolution often differs from the peak amplitude value detected during another revolution. In other words, if measurement were done during a single revolution, then plural single-revolution-measurements on the same shaft would result in rather large variations in the detected peak value.

The inventor realized that it is desirable to achieve a measurement procedure which is reliable in the sense that it should provide repeatable results. Hence, when the measurement procedure is repeatedly performed on the same rotational part so that plural monitoring periods $T_{PM1}$, $T_{PM2}$, $T_{PM3}$, $T_{PM4}$, $T_{PM5}$ result in measurement results in the form of plural representative peak amplitude values $A_{PR1}$, $A_{PR2}$, $A_{PR3}$, $A_{PR4}$ being produced in immediate temporal succession, then it is desirable that these plural representative peak amplitude values $A_{PR1}$, $A_{PR2}$, $A_{PR3}$, $A_{PR4}$ have substantially the same numerical value.

Finite Time Period for Peak Value Detection

By performing numerous test measurements in a laboratory environment where there is very little or no noise, the inventor concluded that it is desirable to monitor a rotating part for the during a finite time period $T_{PM}$ corresponding to several revolutions R in order to detect a true peak amplitude value $A_{PT}$ which is indicative of the mechanical state of the monitored part, i.e. bearings 7 and/or shaft 8. In this context the true peak amplitude value $A_{PT}$ is true in the sense that it truly originates from a mechanical vibration $V_{MD}$ caused by a relative movement between metal surfaces in a monitored part, such as e.g. a bearing ball and an inner ring surface, and not from any noise or disturbance.

In effect the selection of the value for the parameter R is a question which needs careful weighing up, since monitoring during a single revolution, i.e. R=1, is likely to result in a too low peak amplitude value $A_{PT}$ which therefore may be inadequate for indicating the mechanical state of the monitored rotating part. On the other hand, if the rotating part is monitored for an extremely long time, nearing eternity in statistical terms, the detected peak amplitude value $A_{PT}$ will slowly increase to infinity, which in reality means that after an extremely long period of operation a rotating part associated with a bearing assembly will break. Accordingly, the inventor concluded that it is necessary to find a balanced value for the parameter R, so as to on the one hand having a high enough R-value to detect a true peak amplitude value $A_{PT}$ which is indicative of the mechanical state of the monitored part, while on the other hand a low enough R-value so as to keep the duration of the measuring time period $T_{PM}$ at a reasonable finite duration.

Based on numerous test measurements in substantially noise free conditions, the inventor concluded that it is desirable to monitor a rotating part during a finite time period $T_{PM}$ corresponding to a certain amount R of revolution of said rotatable part; said certain amount R of revolution corresponding to at least eight (R=8) revolutions of said monitored rotatable part in order to actually detect a true peak amplitude value $A_{PT}$ which is indicative of the mechanical state of the monitored part. Based on these test measurements, the inventor concluded that monitoring the rotating part during a finite time period $T_{PM}$ corresponding to at least ten (R=10) revolutions of said monitored rotatable part renders a more accurate true peak amplitude value $A_{PT}$, i.e. a true peak amplitude value $A_{PT}$ which is more accurately indicative of the mechanical state of the monitored part. This conclusion is based on tests indicating that a further increase of the monitoring time period $T_{PM}$ to a finite duration of more than ten (R=10) revolutions, in an environment free from noise, may lead to a detection of a higher true peak amplitude value $A_{PT}$, but the increase in detected true peak amplitude value $A_{PT}$ is small in relation to the increased monitoring time period $T_{PM}$.

When measuring and collecting peak amplitude values $A_P$ during a time period $T_{PM}$ corresponding to R=14 full revolutions of the monitored part, and thereafter organising the peak amplitude values $A_P$ in a histogram, as illustrated in FIG. 9, the peak amplitude values $A_P$ sorted into the amplitude level 420 for the 14.th highest detected amplitude is very stable. It can be seen from the histogram in FIG. 9 that four peak amplitudes were detected at that amplitude range 420. Accordingly, a stable measurement value, i.e. repeatedly providing substantially the same peak amplitude when performing plural measurements on the same rotating part, may be achieved by focusing on the R:th highest amplitude, wherein R is a number indicative of the number of revolutions performed by the monitored part during the peak level monitoring time $T_{PM}$.

An embodiment of the invention therefore includes a method of operating an apparatus for analysing the condition of a machine having a part rotating with a speed of rotation $f_{ROT}$, comprising the steps of:

receiving a first digital signal $S_{MD}$, $S_R$, $S_F$ dependent on mechanical vibrations emanating from rotation of said part;

analysing said first digital signal so as to detect peak amplitude values Ap during a finite time period $T_{Pm}$, said finite time period corresponding to a certain amount R of revolution of said rotatable part; said certain amount R of revolution corresponding to more than one revolution of said monitored rotatable part;

sorting said detected peak amplitude values Ap into corresponding amplitude ranges so as to reflect occurrence N of detected peak amplitude values Ap within a plurality $N_R$ of amplitude ranges;

estimating a representative peak amplitude value $A_{PR}$ in dependence on said sorted peak amplitude values Ap and said certain amount R.

According to an advantageous embodiment the estimation includes selecting the R:th highest amplitude to be said representative peak amplitude value $A_{PR}$.

Reducing or Eliminating Noise

Figure 10:
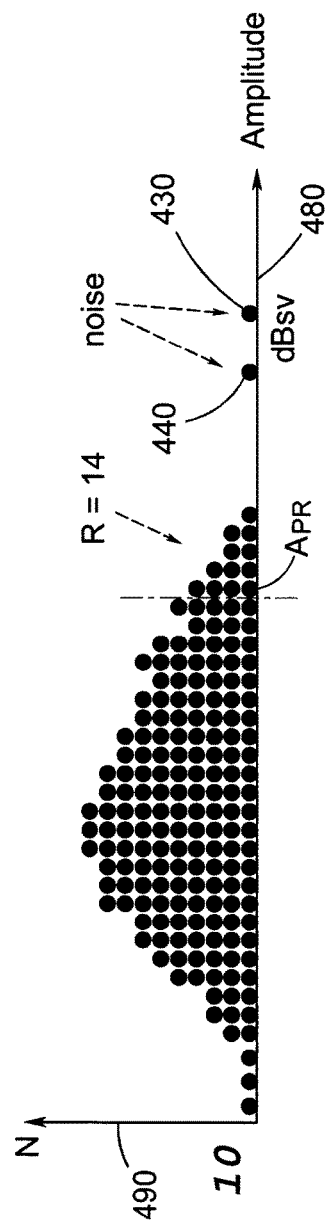
FIG. 10 illustrates a histogram resulting from another measurement where high amplitude noise was introduced during the measurement.

FIG. 10 illustrates a histogram resulting from a measurement wherein the peak level monitoring time $T_{PM}$ corresponded to fourteen (14) revolutions of the monitored rotatable part. The FIG. 10 histogram is the result of an experiment wherein two very high amplitude mechanical disturbances 430, 440 were generated during the peak level monitoring time $T_{PM}$. The two signal peaks corresponding to the two very high amplitude mechanical disturbances 430, 440 are also illustrated in FIG. 8. It is to be understood that the two high amplitude mechanical disturbances 430, 440 were not caused by any damage in the monitored rotational part. Hence, the two high amplitude mechanical disturbances 430, 440 are to be regarded as noise.

Experience and a multitude of measurements have indicated that when monitoring a machine having a part rotating with a speed of rotation the highest peak amplitude value emanating from an incipient damage is a very relevant amplitude value for the purposes of predictive maintenance.

However, since the highest peak amplitude value does not appear every time the monitored shaft revolves one full revolution, it will be necessary to monitor a rotatable part for the duration of a time allowing plural revolutions. Unfortunately, however, in a real life situation a longer measuring time often increases the noise level in the measuring signal. In an industrial environment, such as a paper mill, other machinery in the vicinity of the monitored machine may cause mechanical vibrations or shock pulses from time to time, and the longer the measuring time the greater the risk that such external mechanical vibrations cause the highest detected peak amplitude levels. For these reasons the measurement procedure, intended to provide a reliable and repetitively achievable representative peak amplitude value, needs to satisfy the opposing requirements of:

on the one hand involving measurement over sufficiently long time to collect peak amplitude values over plural revolutions of the monitored rotational part so as to collect a peak amplitude value which is representative of the highest peak amplitude value caused by the condition of the monitored rotational part, while on the other hand avoiding the measurement procedure requiring such a long time that noise caused by e.g. other machinery in an industrial environment corrupts the measurement results.

According to an embodiment of the invention the R:th highest amplitude is selected to be a representative peak amplitude value $A_{PR}$. This embodiment advantageously leads to reduced or eliminated impact of high amplitude noise on the resulting representative peak amplitude value $A_{PR}$. This advantageous effect is understood by studying and comparing FIGS. 9 and 10. Both of the histograms of FIGS. 9 and 10 illustrate a histograms resulting from a measurement duration period $T_{Pm}$, said measurement duration period $T_{Pm}$ corresponding to a certain amount R=14 revolutions of said rotatable part. FIG. 9 illustrates a histogram resulting from a measurement without any noise, whereas FIG. 10 illustrates a histogram resulting from another measurement where high amplitude noise was introduced during the measurement. Selection of the R:th highest amplitude as representative peak amplitude value $A_{PR}$ leads to repeatable results, even when exerted to noise. Hence, when the measurement procedure is repeatedly performed on the same rotational part so that plural monitoring periods $T_{PM1}$, $T_{PM2}$, $T_{PM3}$, $T_{PM4}$, $T_{PM5}$ result in measurement results in the form of plural representative peak amplitude values $A_{PR1}$, $A_{PR2}$, $A_{PR3}$, $A_{PR4}$ being produced in immediate temporal succession, these plural representative peak amplitude values $A_{PR1}$, $A_{PR2}$, $A_{PR3}$, $A_{PR4}$ have substantially the same numerical value, when the R:th highest amplitude is selected to be a representative peak amplitude value $A_{PR}$ and the measurement duration periods $T_{PM1}$, $T_{PM2}$, $T_{PM3}$, $T_{PM4}$, $T_{PM5}$ correspond to R revolutions of said rotatable part. Starting from the right hand side and identifying 14:th highest amplitude value, leads to substantially the same amplitude level, both in the case of FIG. 9 and FIG. 10. Hence, the amplitude level of the R:th highest amplitude value may advantageously be selected representative peak amplitude value $A_{PR}$, according to an embodiment.

However, the nature of the Gaussian function or bell curve is such that the frequency of low amplitude values actually can tell us something about the amplitude of the not-so-frequent highest peak amplitude values.

According to an aspect of the invention, the method includes estimating a representative peak amplitude value ($A_{PR}$) in dependence on said sorted peak amplitude values (Ap) and said certain amount (R).

According to an embodiment the estimation step includes the creation of an accumulated histogram.

Setting Up an Analysis Apparatus for Performing Peak Level Analysis

Figure 11A:
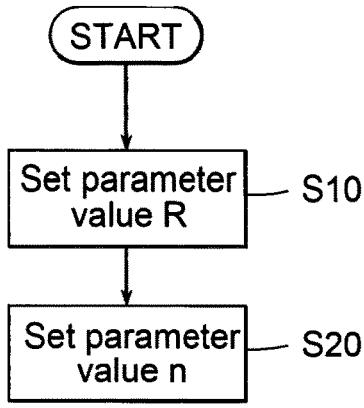
FIG. 11A is a flow chart illustrating an embodiment of a method of operating the apparatus so as to set it up for performing peak level condition analysis.

FIG. 11A is a flow chart illustrating an embodiment of a method of operating the apparatus 14 so as to set it up for performing peak level condition analysis. The method according to FIG. 11A may be performed when an embodiment of the analysis function F3 (See FIG. 4 & FIG. 7) is run on the processor 50 (See FIG. 2A).

In a step S10 a parameter value R is set, and in another optional step S20 a parameter n may be set. According to an embodiment the parameter values R and n, respectively, may be set in connection with the manufacturing or in connection with delivery of the measurement apparatus 14. Accordingly the parameter values R and n may be preset by the manufacturer of apparatus 14, and these values may be stored in the non-volatile memory 52 or in the non-volatile memory 60 (See FIG. 2A).

Alternatively, the parameter values R and n may be set by the user of the apparatus 14 prior to performing a measurement session. The parameter values R and n may be set by the user by means of the user interface 102, 107 described in connection with FIG. 2A.

A Method of Measurement and Data Collection

Figure 11B:
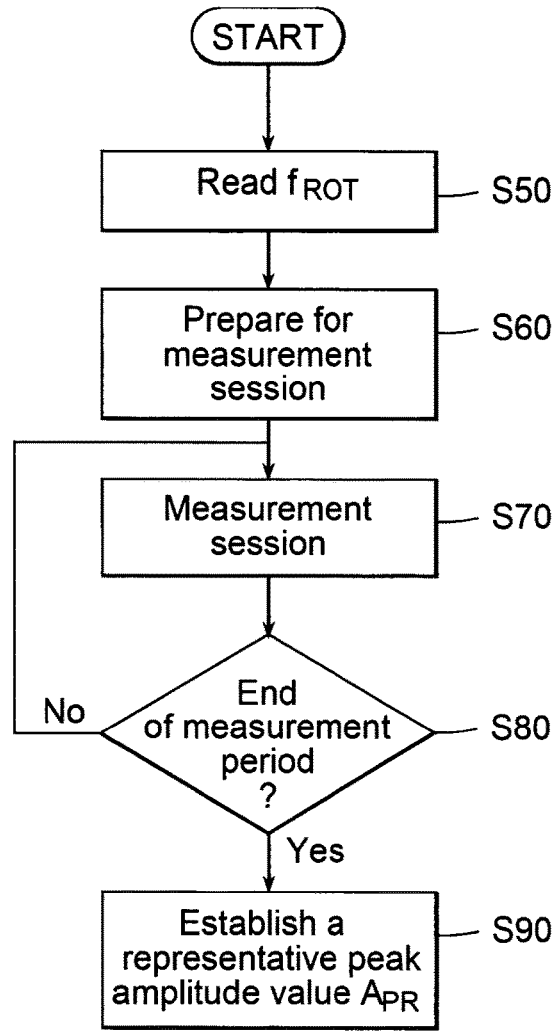
FIG. 11B is a flow chart illustrating an embodiment of a method of operating the apparatus so as to perform peak level condition analysis.

FIG. 11B is a flow chart illustrating an embodiment of a method of operating the apparatus 14 so as to perform peak level condition analysis. The method according to FIG. 11B may be performed when an embodiment of the analysis function F3 (See FIG. 4 & FIG. 7) is run on the processor 50 (See FIG. 2A).

In a step S50 a current speed value $f_{ROT}$ is read, and stored in a data memory 52. When the part 8 to be monitored is rotating with a constant speed of rotation, the speed value $f_{ROT}$ may be entered by a user via the user interface 102 (FIG. 2A). When the rotational speed $f_{ROT}$ of the monitored part is variable, a speed detector 450 (See FIG. 1 & FIG. 5) may be provided to deliver a signal indicative of the speed of rotation $f_{ROT}$ of the shaft 8. The speed of rotation $f_{ROT}$ of the shaft 8 may be provided in terms of revolutions per second, rps, i.e. Hertz (Hz) to an input 460 of means 180 for digital signal processing (See FIG. 5) so that it can be used by the processor 50 (See FIG. 2A) when running the program to execute the peak amplitude analysis function.

In step S60 additional preparations for the measurement session step S70 are performed. The preparations of step S60 may include preparing a suitable table 470 for data to be collected. FIG. 13B is a schematic illustration of plural memory positions arranged as a table 470, and suitable for storage of data to be collected. The table 470 may be stored in the memory 52 (FIG. 2A) or in a memory internal to the processor 50.

Figure 13A:
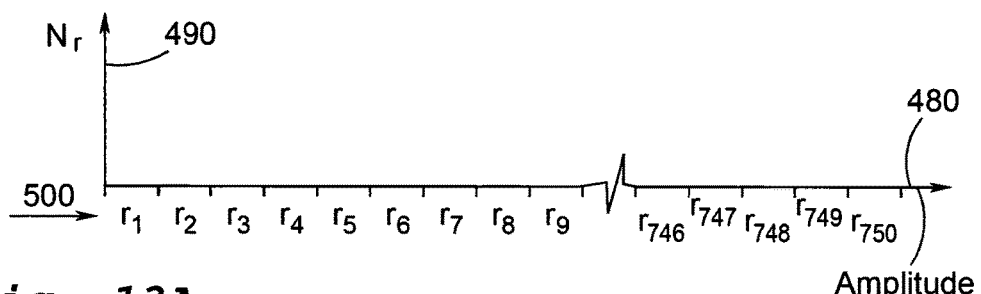
FIG. 13A illustrates a histogram having plural amplitude bins.
Figure 13B:
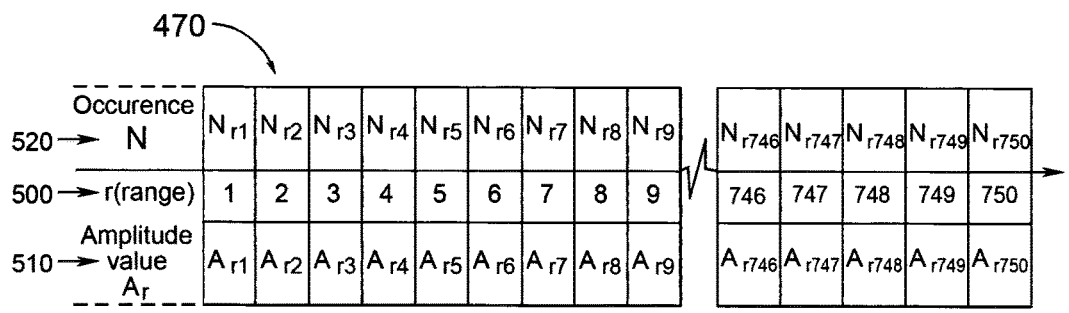
FIG. 13B is a schematic illustration of plural memory positions arranged as a table.

FIG. 13A illustrates a histogram having plural amplitude bins 500, individually referred to by references r1 to r750, each amplitude bin r1 . . . r750 representing an amplitude level $A_r$. Although FIG. 13 shows 750 (seven hundred and fifty) amplitude bins, that is just an example value. The number of amplitude bins may be set to a suitable number in step S60 (FIG. 11B) by the user, via user interface 102 (FIG. 2A). FIG. 13A is comparable with FIG. 10, both figures illustrating a number of amplitude bins along one axis 480, and occurrence of detected peak amplitude values along another axis 490. However, in the illustration of FIG. 13A no values have been plotted in the histogram. The amplitude axis 480 may have a certain resolution, which may also be settable by the user, via the user interface 102. Alternatively the resolution of the amplitude axis 480 may be preset.

According to an embodiment the resolution of the amplitude axis 480 may be set to 0.2 dB, and the amplitudes to be recorded may span from a lowest amplitude of $A_{r1}$=−50 dB to a highest amplitude value $A_{r750}$=+100 dB.

With reference to FIG. 13B, the illustrated table is a representation of the histogram shown in FIG. 13A, having amplitude bins 500, individually referred to by references r1 to r750, each amplitude bin r1 . . . r750 representing an amplitude level $A_r$. The table 470 also includes memory positions 510 for amplitude values Ar, and memory positions 520 for variables $N_r$ reflecting the occurrence.

Bin r1 is associated with an amplitude value $A_{r1}$ and with a memory position for a variable $N_{r1}$ for storing a value indicating how many times the amplitude Ar1 has been detected.

In step S60 (FIG. 11B), before the start of a measuring session S70, all the occurrence variables $N_{r1}$ to $N_{r750}$ may be set to zero (0). Thereafter the measuring session S70 may begin.

The measuring session s70 may include receiving a first digital signal $S_R$, $S_{MDP}$ dependent on mechanical vibrations emanating from rotation of said part (See FIG. 6B & FIG. 7); and analysing said first digital signal $S_R$, $S_{MDP}$ so as to detect peak amplitude values Ap during a finite time period $T_{Pm}$, said finite time period corresponding to a certain amount R of revolution of said rotatable part 8; said certain amount R of revolution corresponding to more than one revolution of said monitored rotatable part; and sorting said detected peak amplitude values Ap into corresponding amplitude ranges 500 so as to reflect occurrence N of detected peak amplitude values Ap within said plurality of amplitude ranges 500 (See FIG. 13B).

The duration of the measurement session is controlled in dependence of the amount of revolution of the rotating part, so that the rotating part rotates at least R revolutions, as mentioned above. Step S80 in FIG. 11B represents the step of controlling the duration of the finite time period $T_{Pm}$ accordingly. A revolution counter may be provided to monitor the signal $f_{ROT}$ so as to ascertain that the measurement session continues for the duration of the finite time period $T_{Pm}$, corresponding to the certain amount R of revolution of said rotatable part 8. Alternatively, the detector 450 may generate a signal indicative of the amount of revolution, and the duration of measurement may be controlled solely in dependence on the amount of revolution of the rotatable part 8, irrespective of time. Alternatively, the duration $T_{Pm}$ of the measurement session is controlled in dependence of time information provided by the clock 190 (FIG. 5) in conjunction with speed of rotation information $f_{ROT}$ delivered by detector 450 so that the duration $T_{Pm}$ is adapted to ensure that the monitoring is performed for the desired amount of rotation n*R. In this connection it is noted that R is a positive number larger than one, and n is a positive number equal to one (1) or larger than one (1). The parameter R may be an integer, but it may alternatively be a decimal number. The parameter n may be an integer, but it may alternatively be a decimal number. In the example shown in FIG. 8 above, parameter R=14 and parameter n=1.

In a step S90 (FIG. 11B) a representative peak amplitude value $A_{PR}$ is established on the basis of the peak amplitude values Ap collected in the measurement session S70.

FIG. 12A is a flow chart illustrating an embodiment of a method of performing step S70 so as to perform the peak level measurement session.

In a step S100 a digital signal $S_R$, $S_{MDP}$ dependent on mechanical vibrations is received by peak level analyzer F3, 310 (See FIG. 7). When a signal peak is detected (Step S110), the peak amplitude value of the detected peak is measured (Step S120), and a corresponding amplitude range $r_i$, also referred to as amplitude range bin, is identified in step S130 (See FIG. 12A in conjunction with FIG. 13B). In a step S140 the corresponding occurrence counter value Nri is increased by one unit so as to reflect detection of a peak in that amplitude range bin $r_i$.

Thereafter step S80 in FIG. 11B is performed so as to determine whether the measuring session is complete or should continue. If is to continue, then steps S100 to S140 are repeated, i.e. step S70 in FIG. 11 is performed again.

When step S80 determines that the measurement session is complete, a representative peak amplitude value $A_{PR}$ is established (S90) on the basis of the peak amplitude values Ap collected in the measurement session S70, as mentioned above.

According to an embodiment, the representative peak amplitude value $A_{PR}$ is compared with a reference value such that the comparison is indicative of the condition of the monitored part. The reference value may be a preset value corresponding to the monitored part. According to an embodiment, the reference value may be a representative peak amplitude value $A_{PR}$ which was established by measurement on the same the monitored part at an earlier time, e.g. when the part was new or freshly renovated. According to an embodiment the above described functions F7=storage of condition data in a writeable information carrier on said machine, and/or F8=storage of condition data in a writeable information carrier 52 in said apparatus, and/or F12=Retrieval of condition data from a writeable information carrier 58 on said machine and/or F13=Performing Peak level analysis F3 and performing function F12 "Retrieval of condition data from a writeable information carrier 58 on said machine" so as to enable a comparison or trending based on current Peak level data and historical Peak level data, are employed.

Establishing Further Improved Representative Peak Value and Noise Rejection

Whereas the measurement results as illustrated in FIG. 9 reflect a highest peak amplitude 410 detected during R=14 revolutions under substantially noise free conditions, the highest peak 430 in the measurement session illustrated in FIG. 10, detected during R=14 revolutions, was generated in response to a disturbance, i.e. it reflects noise, and as such the peak 430 does not carry any information about the condition of the rotating part 8. Accordingly, it is desirable to obtain a representative peak amplitude value $A_{PR}$ which is based on signal values reflecting measurement values delivered by the sensor 10 in dependence on vibrations emanating from the shaft and/or bearing when the shaft rotates. In particular when it comes to measurement on slowly rotating parts, which inherently requires a longer measuring period $T_{PM}$ when measurement is to be performed over a certain predetermined amount of revolution R, the amount of noise may also be increased due to the longer duration of the measuring session required because of the slower rotational speed. Hence, there exists a need for a sturdy measurement method capable of rejecting noise.

In a wind turbine application the shaft whose bearing is analyzed may rotate at a speed of less than 120 revolutions per minute, i.e. the shaft rotational frequency fROT is less than 2 revolutions per second (rps). Sometimes such a shaft to be analyzed rotates at a speed of less than 50 revolutions per minute (rpm), i.e. a shaft rotational frequency fROT of less than 0.83 rps. In fact the speed of rotation may typically be less than 15 rpm. Whereas a shaft having a rotational speed of 1715 rpm, as discussed in the above mentioned book, produces 500 revolutions in just 17.5 seconds; a shaft rotating at 50 revolutions per minute takes ten minutes to produce 500 revolutions. Certain large wind power stations have shafts that may typically rotate at 12 RPM=0.2 rps. At 12 rpm it takes more than four minutes to complete fifty revolutions, and accordingly the risk for impact noise occurring during the measurement is a lot higher when the peak level analysis is to be performed on a rotating part having such a low rotational speed. Similarly certain machine parts in paper mills also rotate at a speed of less than 50 rpm.

As mentioned above, the inventor concluded that it is desirable to monitor a rotating part during a finite time period $T_{PM}$ corresponding to a certain amount R of revolution of said rotatable part; said certain amount R of revolution corresponding to plural revolutions of said monitored rotatable part in order to actually detect a peak amplitude value $A_{PT}$ which is indicative of the mechanical state of the monitored part. However, the inventor concluded that it is preferable to monitor a rotating part during a finite time period $T_{PM}$ corresponding to a certain amount R of revolution of said rotatable part; said certain amount R of revolution corresponding to at least eight (R=8) revolutions of said monitored rotatable part in order to actually detect a true peak amplitude value $A_{PT}$ which is indicative of the mechanical state of the monitored part. This conclusion was based on numerous test measurements in substantially noise free conditions. Hence, monitoring a rotating part during a finite time period $T_{PM}$ corresponding to at least n*R revolutions, wherein n is a number having a numerical value of at least two and R has a numerical value of at least 8, and selecting the n:th highest detected peak amplitude as a representative peak amplitude value $A_{PR}$, will deliver a measured peak amplitude value $A_{PR}$ which statistically occurs once in R revolutions, while rejecting the n−1 highest peak values as potential noise peaks. Accordingly, this embodiment of the invention renders a peak amplitude value $A_{PR}$ which is very accurately indicative of the mechanical state of the monitored part.

As mentioned above, the inventor also concluded, based on the test measurements, that monitoring the rotating part during a finite time period $T_{PM}$ corresponding to at least ten revolutions (R=10) of said monitored rotatable part may render an even more accurate true peak amplitude value $A_{PT}$, i.e. a true peak amplitude value $A_{PT}$ which is more accurately indicative of the mechanical state of the monitored part. Moreover, the inventor concluded that the tests indicate that a further increase of the monitoring time period $T_{PM}$ to a finite duration of more than ten revolutions (R>10), in an environment free from noise, may lead to a detection of a higher true peak amplitude value $A_{PT}$, but the increase in detected true peak amplitude value $A_{PT}$ is small in relation to the increased monitoring time period $T_{PM}$.

Accordingly, the inventor concluded that a problem to be solved is: How to identify a peak amplitude value which statistically occurs once in R revolutions, while satisfying the conflicting requirements of obtaining as accurate as possible a measured peak amplitude value and while minimizing the measuring duration and achieving rejection of peaks that are due to noise.

Figure 14A:
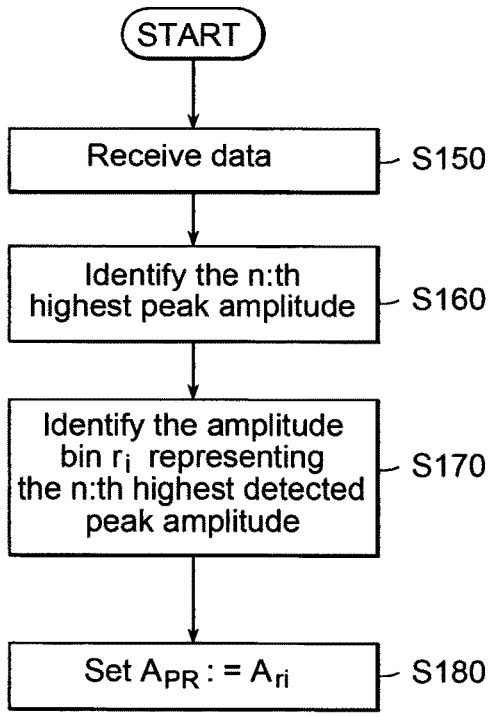
FIG. 14A is a flow chart illustrating an embodiment of a method for establishing a representative peak amplitude value on the basis of the peak amplitude values Ap collected in the measurement session.

FIG. 14A is a flow chart illustrating an embodiment of a method for establishing a representative peak amplitude value $A_{PR}$ on the basis of the peak amplitude values Ap collected in the measurement session S70 (See FIG. 11A). The method of the FIG. 14A embodiment illustrates a manner by which high amplitude noise may be rejected. Accordingly the method according to FIG. 14A may advantageously be employed for peak level analysis of rotatable parts having a speed of less than 50 rpm.

Figure 13C:
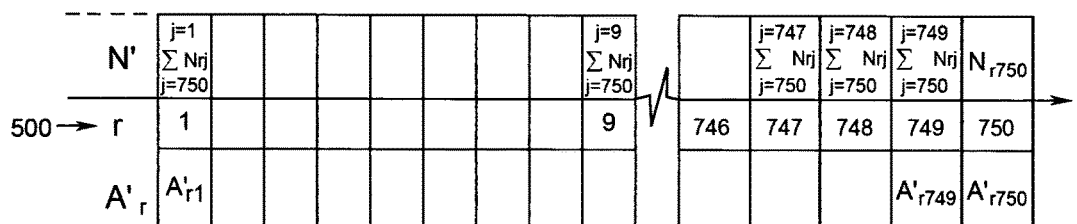
FIG. 13C is an illustration of a cumulative histogram table corresponding to the histogram table of FIG. 13B.

In a step S150 data relevant for the analysis is read. This includes the value of the parameter R, used in the measuring session S70, and the value of the parameter n. It may also include the peak value measurement data in histogram format, as illustrated in FIG. 13A, 13B or 13C. The peak value measurement data to be analyzed may be the data collected as described above, e.g. in connection with steps S70 & S80 above and/or as described in connection with FIG. 12A or 12B.

In step S160, identify the top n:th highest detected peak amplitude value. Referring to FIG. 13B, and assuming data is sorted so that the highest amplitude bin is at the right hand side of the FIG. 13B table (i.e. amplitude $A_{r750}$, associated with bin $r_{750}$, represents the highest detectable amplitude value), this means beginning with occurrence $N_{r750}$, moving left and adding occurrence values $N_{ri}$ until the sum equals n. Having found the n:th highest detected amplitude, the subsequent step S170 includes identifying the amplitude bin $r_i$ representing the n:th highest detected peak amplitude value and the corresponding amplitude value $A_{ri}$.

In the subsequent step S180, select the identified amplitude value $A_{ri}$ to be an estimate of the representative peak amplitude $A_{PR}$:

$$A_{PR}:=A_{ri}$$

Accordingly, an embodiment of the invention includes a method of operating an apparatus for analysing the condition of a machine having a part rotating with a speed of rotation $f_{ROT}$, comprising the steps of:

receiving a first digital signal $S_{MD}$, $S_R$, $S_F$ dependent on mechanical vibrations emanating from rotation of said part;

analysing said first digital signal so as to detect peak amplitude values Ap during a finite time period $T_{Pm}$, said finite time period corresponding to a certain amount of revolution of said rotatable part; said certain amount of revolution corresponding to more than one revolution of said monitored rotatable part;

sorting each said detected peak amplitude value Ap into a corresponding amplitude bin 500, $r_1$-$r_{750}$ (See FIGS. 13B and 13C) so as to reflect occurrence N of detected peak amplitude values Ap within a plurality $N_R$ of amplitude ranges;

estimating a representative peak amplitude value $A_{PR}$ in dependence on said sorted peak amplitude values Ap and said certain amount of revolution; wherein said certain amount of revolution includes at least n*R revolutions, wherein n is a number having a numerical value of at least two and R corresponds to several revolutions, and wherein the estimation step includes selecting the n:th highest detected peak amplitude as a representative peak amplitude value $A_{PR}$.

This solution advantageously rejects the n−1 highest amplitude peak values as noise, and delivers the n:th largest amplitude peak value as a representative peak amplitude value APR. According to this embodiment the duration of a measurement session, expressed in number of revolutions, will be n*R, and the number of rejected noise peak values is n−1.

According to an embodiment, n is a number having a numerical value of at least two and R has a numerical value of at least 8, rendering measurement and collection of peak amplitude values during at least n*R=2*8=16 revolutions of the monitored part (Steps S70 and S80 in FIG. 11B).

According to a preferred embodiment, referring to steps S10 and S20 in FIG. 11A, the parameter R is set to at least 10, and parameter n is set to 5, rendering measurement and collection of peak amplitude values during n*R=5*10=50 revolutions of the monitored part (Steps S70 and S80 in FIG. 11B).

If a true peak value is generated at least once in R revolutions, and there is also some high amplitude noise in the form of false peak values, then according to this embodiment the four highest peak values may be rejected and the method will still identify a true peak value in the form of the n:th largest detected peak value, i.e. the fifth largest detected peak value. Accordingly, assuming that the amount of high amplitude disturbance results in at the most four of the top five peak values, this embodiment delivers the amplitude of the 5:th largest peak value as a representative peak amplitude value $A_{PR}$.

According to preferred embodiments of the invention the parameter R may take values of 8 or higher, and the parameter n may have values of 2 or higher. According to these embodiments the duration of a measurement session, expressed in number of revolutions, will be n*R, and the number of rejected noise peak values is n-1.

The below Table 1 illustrates a few examples of combinations of parameter settings for R and n, together with resulting duration of measuring session and the corresponding capability of noise rejection.

TABLE 1

| R | n | Duration of measurement session (revolutions) | Number of rejected noise peaks |
|---|---|---|---|
| 8 | 5 | 40 | 4 |
| 9 | 5 | 45 | 4 |
| 10 | 5 | 50 | 4 |
| 10 | 6 | 60 | 5 |
| 10 | 7 | 70 | 6 |
| 10 | 8 | 80 | 7 |
| 10 | 9 | 90 | 8 |
| 10 | 10 | 100 | 9 |
| 10 | 11 | 110 | 10 |
| 10 | 12 | 120 | 11 |
| 10 | 13 | 130 | 12 |
| 10 | 14 | 140 | 13 |
| 9 | 6 | 54 | 5 |
| 9 | 7 | 63 | 6 |
| 9 | 8 | 72 | 7 |
| 9 | 9 | 81 | 8 |
| 9 | 10 | 90 | 9 |
| 9 | 11 | 99 | 10 |
| 9 | 12 | 108 | 11 |

However, the inventor also concluded that since the distribution of true peak amplitude values emanating from rotation of a monitored rotational part closely follow the normal distribution, it may be possible to estimate a peak amplitude value which statistically occurs seldom, on the basis of detected peak amplitude values which occur more frequently. On the basis of this realization, the inventor proceeded to develop a further advantageous manner of estimating a representative peak amplitude value $A_{PR}$ in dependence on the sorted peak amplitude values Ap and the amount R of rotation of the monitored part, as discussed below in connection with FIG. 14B.

Yet a Further Improved Representative Peak Value and Noise Rejection

Figure 14B:
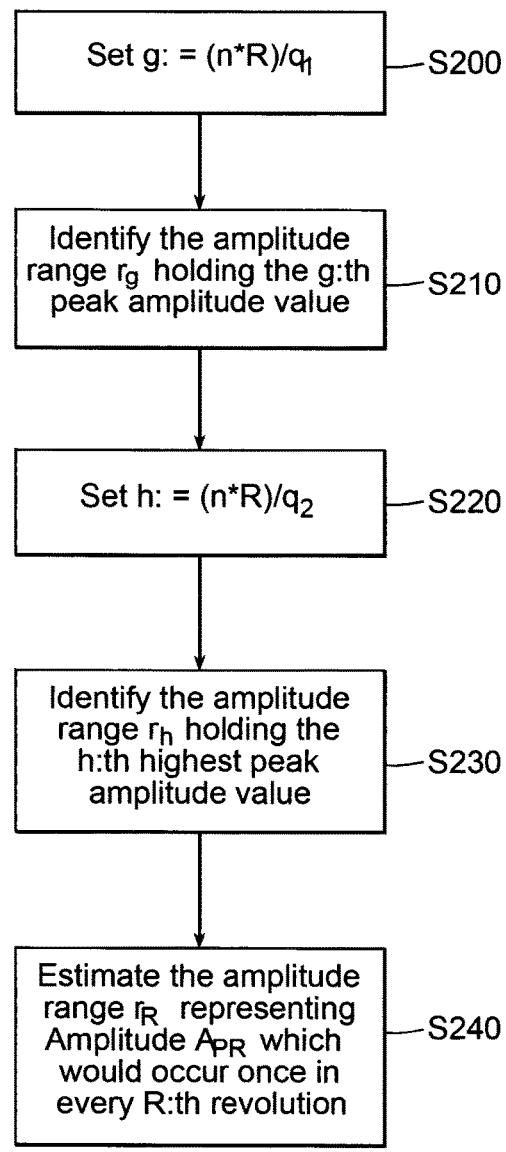
FIG. 14B is a flow chart illustrating yet an embodiment of a method for estimating a representative peak amplitude value $A_{PR}$ on the basis of the peak amplitude values Ap collected in the measurement session.

FIG. 14B is a flow chart illustrating yet an embodiment of a method for estimating a representative peak amplitude value $A_{PR}$ on the basis of the peak amplitude values Ap collected in the measurement session S70. The method of FIG. 14B may be an embodiment of step S90 of FIG. 11B.

In a step S 200 a parameter g is set to a value (n*R)/q$_1$:

$$g:=(n*R)/q_1$$

The parameter $q_1$ may have a numerical value 1 or more than 1. According to embodiments of the invention parameter $q_1$ is preset to a value of between one (1) and three (3).

In a step S210, an amplitude range $r_g$ (See FIG. 13) holding the g:th largest detected peak amplitude value is identified.

In a step S220 a parameter h is set to a value (n*R)/q$_2$:

$$h=(n*R)/q_2$$

According to embodiments of the invention, the parameter $q_2$ is preset to a value of between two (2) and five (5). According to an embodiment the parameter $q_2$ may have a numerical value four (4). The value of parameter $q_2$ is always larger than the value of parameter $q_1$:

$$q_2 > q_1$$

In a step S230, an amplitude range $r_h$ (See FIG. 13) holding the h:th largest detected peak amplitude value is identified.

In a step S240, an estimate of a representative peak amplitude value $A_{PR}$ is achieved on the basis of the values ($r_g$, g) and ($r_h$, h). This will be explained in further detail below in connection with FIG. 15A.

Setting parameters n=5, R=10, and $q_1$=1 in step S200 renders g=50. Hence the measuring session includes 50 revolutions (since n*R=50), and setting g=50 implies that we identify the position in the histogram where the 50:th largest detected pulse is stored. Hence, with reference e.g. to the histogram of FIG. 13, we are identifying the position where pulse amplitudes that occur with a frequency of once per revolution will be reflected. Differently worded, it to be understood that, since the distribution of true peak amplitude values emanating from rotation of a monitored rotational part closely follows the normal distribution, then sorting the detected peak amplitude values into amplitude bins r, 500 (See FIGS. 13A, 13B and/or 13C), and then identifying the amplitude bin r, 500 holding the g:th largest detected peak amplitude value, renders identification of an amplitude value $r_g$ which has occurred 50 times (since g=50) during 50 revolutions (since n*R=50), i.e. statistically a peak amplitude of at least the peak amplitude value $r_g$ has occurred g/(n*R) times/revolution, which is once per revolution when g=50 and n*R=50. In other words, the average occurrence frequency $f_{ag}$, expressed as occurrences per revolution, of an amplitude having a value of $r_g$ or higher is:

$$f_{ag} = g/(n*R) \text{ occurrences/revolution}$$

Similarly, setting the parameter $q_2$=4 in step S200 renders h=n*R/$q_2$=12.5. Hence the measuring session includes 50 revolutions (since n*R=50), and setting h=12 implies that we identify the position in the histogram where the 12:th largest detected pulse is stored. Hence we are identifying the position in the histogram of FIG. 13 where pulses that occur with a frequency of once every four revolutions will be reflected. In other words, the average occurrence frequency $f_{ah}$, expressed as occurrences per revolution, of an amplitude having a value of $r_h$ or higher is:

$$f_{ah} = h/(n*R) \text{ occurrences/revolution}$$

When parameters n=5, R=10, and h=n*R/$q_2$=12.5, renders $f_{ah}$=h/(n*R)=¼ occurrences/revolution, i.e one occurrence every four revolutions As mentioned above, the nature of the Gaussian function or bell curve is such that the amplitude and frequency of low amplitude values actually can tell us something about the amplitude of the not-so-frequent highest peak amplitude values. This is true even if only a part of the amplitude-frequency plot (See FIG. 9, 10, 13A, 13C) resembles the Gaussian function or bell curve, such as e.g if the high amplitude part of the plot of detected peak values follows the Gaussian function or bell curve.

Since at least the high amplitude part of the distribution of true peak amplitude values emanating from rotation of a monitored rotational part closely follow the normal distribution, these two positions in the histogram may be used for estimating a peak amplitude value which statistically occurs more seldom. As mentioned above (See heading "Finite Time Period for Peak Value Detection" above), the representative peak amplitude value $A_{PR}$ may be an amplitude which statistically occurs once every R revolutions. Accordingly, having set parameter R to value 10, the method includes estimating the amplitude of a peak value occurring once in ten revolutions, based on the observation of occurrence frequency and amplitude of peaks occurring once per revolution and once in four revolutions. Advantageously, this method enables the rejection of 11 high amplitude false peak values while still enabling the estimation of an accurate representative peak amplitude value $A_{PR}$, when parameters g and h, respectively, are set as mentioned above, i.e. g=50 and h=12.5. Moreover, it is to be noted that this method enables the rejection of 11 high amplitude false peak values while reducing the required measurement session duration $T_{PM}$ to merely the duration of 50 revolutions. This is since n*R=5*10=50. This effect is advantageously achieved since parameters q1 and q2 are selected such that the two parameters g & h are selected to values representing relatively high frequency of occurrence of peak amplitude values, and the amplitudes of the high occurrence frequency values are used for estimating a peak amplitude value $A_{PR}$ which statistically occurs more seldom, such as once in R revolutions. Hence, a representative peak amplitude level $A_{PR}$ having an average occurrence of once every R:th revolution can be estimated on the basis of the peak amplitude levels having an average occurrence of once every g:th revolution and the peak amplitude levels having an average occurrence of once every h:th revolution. The number of rejected noise peaks $P_{NR}$ is one less than the truncated value of h:

$$P_{NR} = TRUNC(h) - 1$$

Accordingly the embodiment according to FIG. 14B enables substantially the same accuracy in estimation of representative peak amplitude value $A_{PR}$ based on measurement during 50 revolutions as the method according to the FIG. 14A embodiment does based on measurement during 120 revolutions (compare with Table 1 above).

The below Table 2 illustrates a few examples of combinations of parameter settings for R and n, together with resulting duration of measuring session and the corresponding capability of noise rejection.

TABLE 2

| R | n | Duration of measurement session (revolutions) | Parameter q2 | Parameter h = (n*R)/q2 | Number of rejected noise peaks |
|---|---|---|---|---|---|
| 8 | 5 | 40 | 4 | 10 | 9 |
| 9 | 5 | 45 | 4 | 11.25 | 10 |
| 10 | 5 | 50 | 4 | 12.5 | 11 |
| 10 | 6 | 60 | 4 | 15 | 14 |
| 10 | 7 | 70 | 4 | 17.5 | 16 |
| 10 | 8 | 80 | 4 | 20 | 19 |
| 10 | 9 | 90 | 4 | 22.5 | 21 |
| 10 | 10 | 100 | 4 | 25 | 24 |
| 10 | 11 | 110 | 4 | 27.5 | 26 |
| 10 | 12 | 120 | 4 | 30 | 29 |
| 10 | 13 | 130 | 4 | 32.5 | 31 |
| 10 | 14 | 140 | 4 | 35 | 34 |
| 9 | 6 | 54 | 4 | 13.5 | 12 |
| 9 | 7 | 63 | 4 | 15.75 | 14 |
| 9 | 8 | 72 | 4 | 18 | 17 |
| 9 | 9 | 81 | 4 | 20.25 | 19 |
| 9 | 10 | 90 | 4 | 22.5 | 21 |
| 9 | 11 | 99 | 4 | 24.75 | 23 |
| 9 | 12 | 108 | 4 | 27 | 26 |

According to an embodiment of the invention, the estimation may be performed by producing an accumulated histogram table reflecting all amplitudes detected in a measurement session and their frequency of occurrence. FIG. 13C is an illustration of such a cumulative histogram table 530 corresponding to the histogram table of FIG. 13B. The cumulative histogram table of FIG. 13C includes the same number of amplitude range bins as the FIG. 13B table. In the cumulative histogram the occurrence N' is reflected as the number of occurrences of detected peaks having an amplitude higher than the amplitude $A_r'$ of associated amplitude bin r. This advantageously provides for a smoother curve when the cumulative histogram is plotted. Whereas the 'ordinary' histogram reflecting a limited number of observations will reflect a lack of observations N at an amplitude bin as a notch or dent at that bin, the cumulative histogram will provide a smoother curve, which makes is more suitable for use in estimating occurrence at one amplitude level based on the observation of occurrences at other amplitude levels.

According to an embodiment of the invention, the amplitude levels are reflected as logarithmic values, and also the cumulative occurrence is reflected by the logarithmic value of the cumulative occurrence.

Figure 15A:
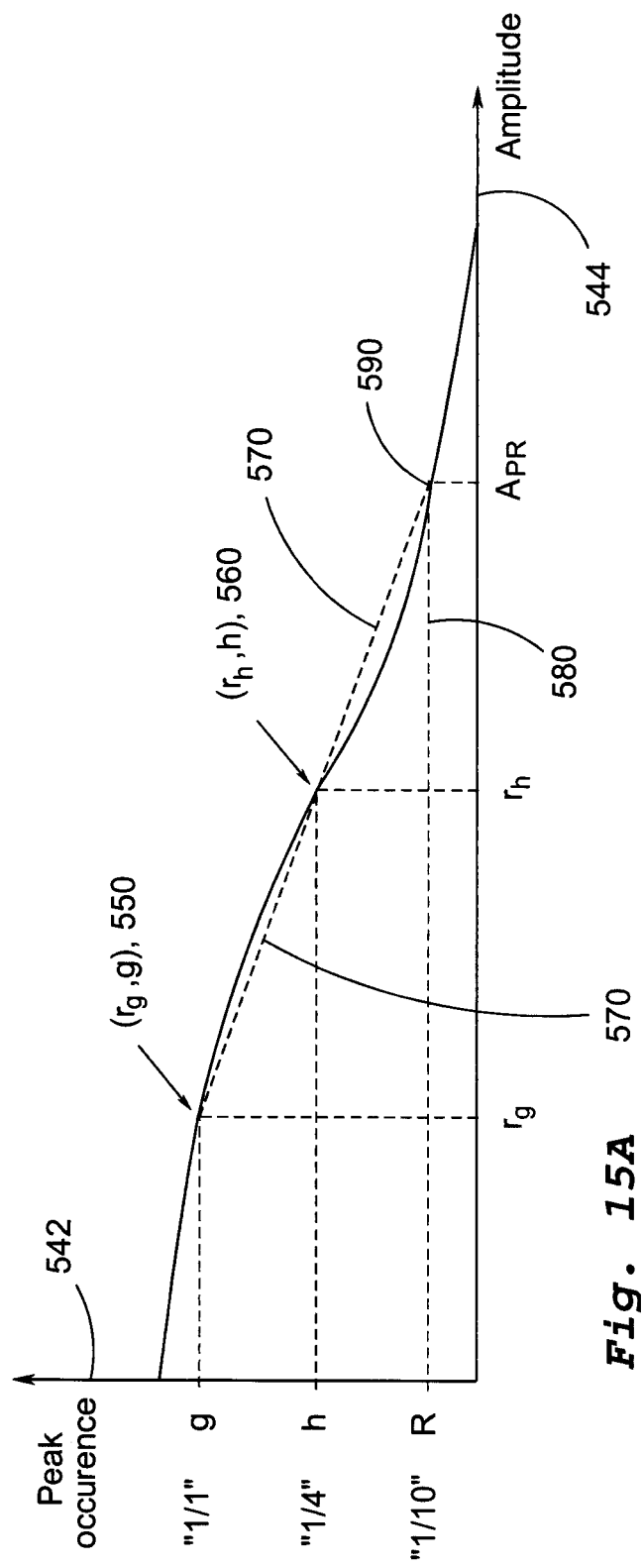
FIG. 15A is an illustration reflecting the principle of a cumulative histogram resulting from a measurement.

FIG. 15A is an illustration reflecting the principle of a cumulative histogram resulting from a measurement, and corresponding to the table of FIG. 13C. Although a cumulative histogram using real detected values may take a different shape from that shown in FIG. 15A, the principle of estimating the representative peak amplitude $A_{PR}$, reflecting the amplitude level which occurs once every R:th revolution, is illustrated in FIG. 15A.

One axis 542 of the cumulative histogram reflects occurrence, and the other axis 544 reflects amplitude. When n=5, R=10, q1=1 then g=50 representing 50 occurences, which also corresponds to one occurrence per revolution. One occurrence per revolution may be written: "1/1". Accordingly, the axis 542 of the cumulative histogram reflecting occurrence may reflect g as "1/1". Similarly h may reflect an occurrence of one in four also expressed as "1/4", and when R=10, then R may reflect an occurrence of one in ten also expressed as "1/10" (See FIG. 15A).

Parameter values rg, g and rh, h, may be determined in the manner described above in connection with FIG. 14B. Parameter values rg, g reflects a point 550 in the cumulative histogram indicating peaks that occur once per revolution. Parameter values rh, h reflects a point 560 in the cumulative histogram indicating peaks that occur once per four revolutions. The inventor realized that in the logarithmic cumulative histogram this part of the normal distribution curve closely resembles a straight line, making it possible to draw a straight line 570 through points 550 and 560. When that line 570 is extended it will cross a line 580 representing the R-occurrence at a point 590. The amplitude value of point 590 represents the amplitude level $A_{PR}$ which occurs once every R:th revolution. Hence, a representative peak amplitude level $A_{PR}$ having an average occurrence of once every R:th revolution can be estimated on the basis of the peak amplitude levels having an average occurrence of once every g:th revolution and the peak amplitude levels having an average occurrence of once every h:th revolution. FIG. 15A illustrates this, with example values g=1, h=4 and R=10.

On the basis of testing, the inventor established that the parameter q1 should advantageously have a value of no less than one (1), since selecting the parameter q1 to less than one may lead to poor results in the estimation process because a cumulative histogram reflecting a bearing assembly having an outer ring damage deviates comparatively more from a straight line, thereby rendering a larger error in the estimation.

Accordingly, an embodiment of the invention includes a method of operating an apparatus for analysing the condition of a machine having a part rotating with a speed of rotation $f_{ROT}$, comprising the steps of:

receiving a first digital signal $S_{MD}$, $S_R$, $S_F$ dependent on mechanical vibrations emanating from rotation of said part;

detecting peak amplitude values Ap occurring in said first digital signal during a finite time period $T_{Pm}$, said finite time period corresponding to a certain amount of revolution of said rotatable part; said certain amount of revolution corresponding to more than one revolution of said monitored rotatable part;

sorting each said detected peak amplitude value Ap into a corresponding amplitude bin 500, $r_1$-$r_{750}$ (See FIGS. 13B and 13C) so as to reflect occurrence N of detected peak amplitude values Ap within a plurality Nri of amplitude ranges;

estimating a representative peak amplitude value $A_{PR}$ in dependence on said sorted peak amplitude values Ap and said certain amount of revolution; wherein said certain amount of revolution includes at least R revolutions, and wherein the estimation step includes estimating an amplitude value $A_{PR}$, which occurs on average substantially once per R revolutions, in dependence of detected amplitude levels $A_P$ which on average occur more frequently than once per R revolutions.

According to an embodiment of the above solution, said certain amount of revolution includes at least n*R revolutions, wherein n is a number having a numerical value of at least 1 and R has a numerical value of at least 8.

According to another embodiment, n is a number having a numerical value of at least 2 and R has a numerical value of at least 8.

According to an embodiment there is provided a method of operating an apparatus for analysing the condition of a machine having a part rotating with a speed of rotation $f_{ROT}$, comprising the steps of:

receiving a first digital signal $S_{MD}$, $S_R$, $S_F$ dependent on mechanical vibrations emanating from rotation of said part;

detecting peak amplitude values Ap occurring in said first digital signal during a finite time period $T_{Pm}$, said finite time period corresponding to a certain amount of revolution of said rotatable part; said certain amount of revolution corresponding to more than one revolution of said monitored rotatable part;

sorting each said detected peak amplitude value Ap into a corresponding amplitude bin 500, $r_1$-$r_{750}$ (See FIGS. 13B and 13C) so as to reflect occurrence N of detected peak amplitude values Ap within a plurality $N_R$ of amplitude ranges;

estimating a representative peak amplitude value $A_{PR}$ in dependence on said sorted peak amplitude values Ap and said certain amount of revolution; wherein said certain amount of revolution includes at least n*R revolutions, wherein n is a number having a numerical value of at least two and R has a numerical value of at least 8, and wherein the estimation step includes estimating an amplitude value $A_{PR}$ which occurs on average substantially once per R revolutions in dependence of detected amplitude levels $A_P$ which occur once every h:th revolution, wherein h has a numerical value of less than n*R. According to an aspect of this solution, the estimation step includes estimating an amplitude value $A_{PR}$ which occurs on average substantially once per R revolutions in dependence of detected amplitude levels $A_P$ which occur once every h:th revolution, wherein h has a numerical value of less than n*R and in dependence of detected amplitude levels $A_P$ which occur once every g:th revolution, wherein g has a numerical value of less than h.

An embodiment of the invention includes a method of operating an apparatus for analysing the condition of a machine having a part rotating with a speed of rotation $f_{ROT}$, comprising the steps of:

receiving a first digital signal $S_{MD}$, $S_R$, $S_F$ dependent on mechanical vibrations emanating from rotation of said part;

detecting peak amplitude values Ap occurring in said first digital signal during a finite time period $T_{Pm}$, said finite time period corresponding to a certain amount of revolution of said rotatable part; said certain amount of revolution corresponding to more than one revolution of said monitored rotatable part;

sorting each said detected peak amplitude value Ap into a corresponding amplitude bin 500, $r_1$-$r_{750}$ (See FIGS. 13B and 13C) so as to reflect occurrence N of detected peak amplitude values Ap within a plurality Nri of amplitude ranges;

estimating a representative peak amplitude value $A_{PR}$ in dependence on said sorted peak amplitude values Ap and said certain amount of revolution; wherein said certain amount of revolution includes at least n*R revolutions, and wherein the estimation step includes estimating an amplitude value $A_{PR}$, which occurs on average substantially once per R revolutions, in dependence of detected amplitude levels $A_P$ which on average occur more frequently than once per R revolutions.

This solution advantageously provides repeatable results since the delivered amplitude level $A_{PR}$ is based on measured values having a high occurrence frequency. Moreover, the delivered amplitude level $A_{PR}$ is substantially the highest measurable amplitude level detectable from a rotating machine part during a finite time period $T_{Pm}$, as discussed above and as shown by tests performed by the inventor.

Noise Echo Suppression

Moreover, the inventor realized that impact noise in industrial environments, which may be caused by an item hitting the body of the machine having a monitored rotating part 8, may cause shock waves which travel back and forth, echoing in the body of the machine. Accordingly, such echoing shock waves may be picked up by the sensor 10

(FIG. 1, 2A, 5) and reflected in the resulting signal $S_R$, $S_{MDP}$ (FIG. 6B, 7) as a burst of amplitude peaks.

Hence, such a burst of amplitude peaks may unfortunately cause corruption of a peak level analysis, unless the impact of such bursts can be reduced or eliminated.

FIG. 12B is a flow chart illustrating an embodiment of a method of performing step S70 (FIG. 11B) so as to perform the peak level measurement session and additionally addressing the impact of bursts of noise amplitude peaks.

Step S300 of the method embodiment illustrated in FIG. 12B may be performed after step S60, as described in connection with FIG. 11B above. In step S300 the peak level analyzer reads the current rotational speed $f_{ROT}$, which may be delivered from the speed detector 450, as described above (See FIG. 5). The reading of a real time value of the rotational speed $f_{ROT}$ advantageously enables this method to be performed also when the rotational part to be analysed rotates with a variable speed of rotation.

In a step S310 an echo suppression period $T_{es}$ is calculated. The echo suppression period $T_{es}$ is set to:

$$T_{es} := 1/(e \cdot f_{ROT})$$

Wherein, according to an embodiment, e is a factor having a value equal to ten or less than ten:

$$e <= 10$$

An effect of the echo suppression method is to reduce the number of peak values per revolution of the monitored part 8 to a maximum of e peaks per revolution. Accordingly, selecting e=10 renders a maximum delivery of 10 peaks per revolution. Differently worded the echo suppression period $T_{es}$ will have a duration corresponding to the duration of one tenth revolution, when e=10. The factor e may be set to another other value, such as e.g 8 or 12.

In a step S320 the measurement signal $S_{MDP}$, $S_R$ to be analyzed is received, and in a step S330 the amplitude of the received signal $S_R$ is analyzed so as to detect any received peak values.

In a step S340 any detected peak values $A_P$ are delivered at a frequency of $f_{es}$ or less, wherein each delivered peak amplitude value reflects the highest detected amplitude during the echo suppression period $T_{es}$. This is done so that there may be longer time than one echo suppression period $T_{es}$ between two consecutively delivered output values from the echo suppresser, but the period between two consecutively delivered output values from the echo suppresser will never be shorter than the echo suppression period $T_{es}$.

In a subsequent step S350, the peak values $A_P$ delivered by the echo suppresser are received by a log generator. The log generator calculates the logarithm of the peak value $A_P$ in real time.

In a step S360 the amplitude bin corresponding to the relevant peak value $A_P$ is identified in a histogram table 470 and/or 530 (See histogram table 470 and cumulative histogram table 530 in FIGS. 13B and 13C, respectively), and in a step S370 the corresponding occurrence counter value $N_{ri}$, $N_{ri}'$ is increased by one unit.

Figure 16:
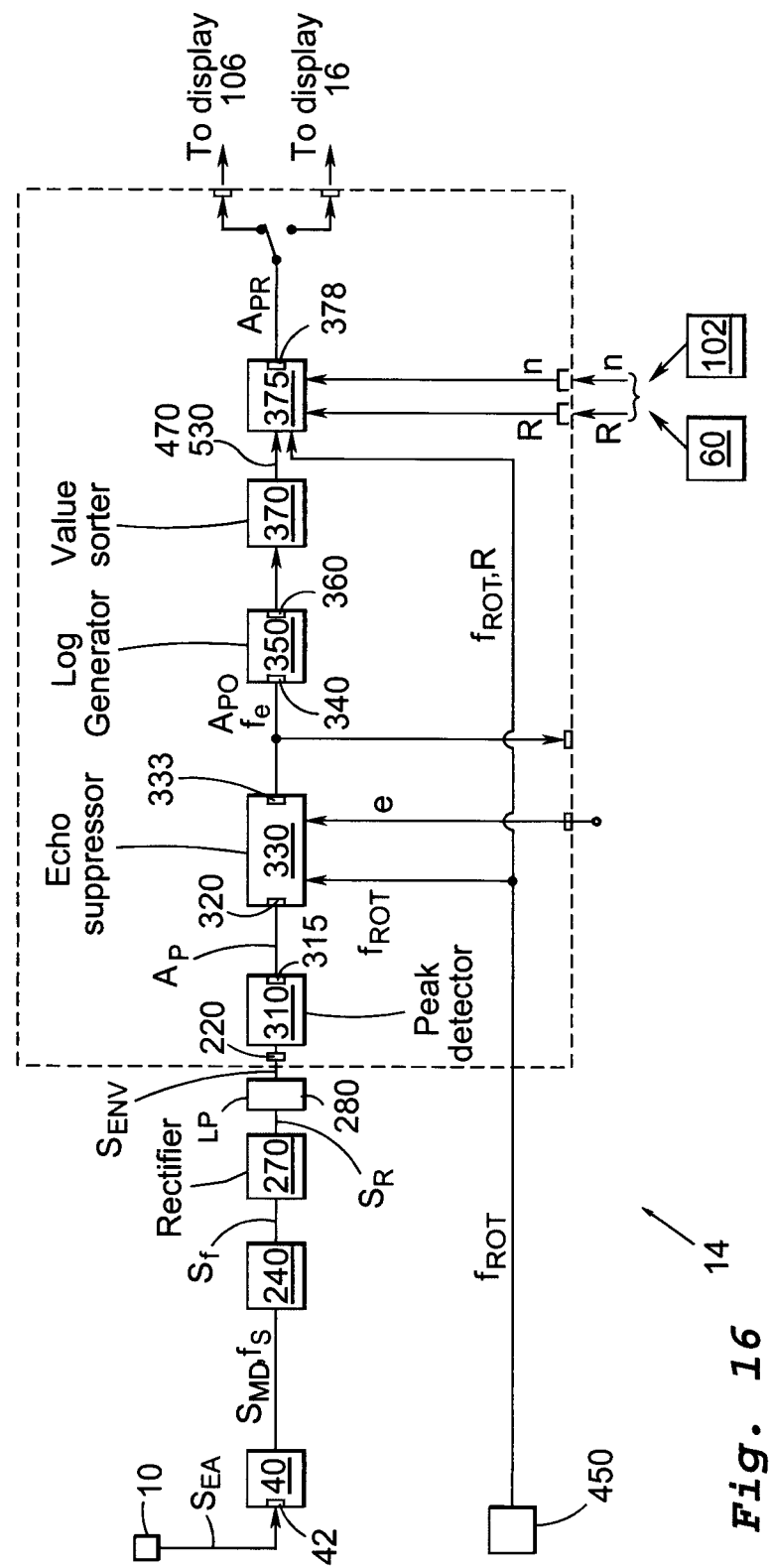
FIG. 16 is a schematic block diagram of an embodiment of the analysis apparatus.

FIG. 16 is a schematic block diagram of an embodiment of the analysis apparatus 14. A sensor unit 10 is adapted to generate an analogue signal $S_{EA}$ in response to vibrations, as described above in this document. The sensor unit 10 may be a vibration sensor as discussed in connection with FIG. 2B above. Alternatively, the sensor unit 10 may be a resonant Shock Pulse Measurement sensor 10 having a mechanical resonance frequency $f_{RM}$, as discussed in connection with FIG. 2B above. This mechanical resonance feature of the Shock Pulse Measurement sensor advantageously renders repeatable measurement results in that the output signal from a Shock Pulse Measurement sensor has a stable resonance frequency substantially independent of the physical path between the shock pulse signal source and the shock pulse sensor.

The analogue signal $S_{EA}$ may be delivered to input 42 of A/D converter 40 which is adapted to generate a digital signal $S_{MD}$ having a sampling frequency $f_S$, as discussed above. The digital signal $S_{MD}$ may be delivered to a band pass filter 240 generating a filtered signal $S_F$ in response thereto. The filtered signal $S_F$ may be delivered to a rectifier 270, as discussed above in connection with FIG. 6B, delivering a rectified signal $S_R$ having sampling frequency $f_S$. The rectified signal $S_R$ may optionally be delivered to a low pass filter 280 so as to produce a digital envelop signal $S_{ENV}$ having sampling frequency $f_S$, as discussed above.

According to an embodiment, the digital envelop signal $S_{ENV}$ may be delivered to an input 220 of evaluator 230, as discussed above in connection with FIG. 6B and FIG. 7 (See also FIG. 16). The digital envelop signal $S_{ENV}$ may be delivered to an input of a peak detector 310. The peak detector 310 may operate to deliver detected signal peaks or detected signal peak values Ap to an output 315 in response to the digital envelop signal $S_{ENV}$. As mentioned above, digital signal processing may advantageously be performed by the data processor 50 running program code for causing the data processor 50 to perform the digital signal processing. According to an embodiment of the invention the processor 50 is embodied by a Digital Signal Processor, DSP 50. The DSP 50 advantageously operates sufficiently fast to enable execution of the described digital signal processing on received signal $S_{ENV}$ having the same or substantially the same sampling frequency $f_S$ as delivered by A/D converter 40. The feature of performing the signal processing on signals at the sampling frequency $f_S$ ensures advantageously accurate peak value detection. It may also be possible to provide a decimator before the peak value detector so as to detect peak values on a decimated signal having a lower sampling frequency. However, tests performed by the inventor indicate that performing peak value detection on a signal at the higher sampling frequency $f_S$ advantageously ensures more accurate peak value detection.

The detected signal peaks or detected signal peak values Ap may be delivered from the peak detector output 315 to an input 320 of an optional echo suppresser 330. Alternatively, the detected signal peaks or detected signal peak values Ap may be delivered from the peak detector output 315 to an input 340 of a log generator 350. The log generator 350 is adapted to generate the logarithmic amplitude values corresponding to the amplitude of the received detected signal peaks or detected signal peak values Ap. Hence, an output 360 of log generator 350 is adapted to deliver logarithmic amplitude values. A value sorter 370 is adapted to receive the logarithmic amplitude values and to sort the received the logarithmic amplitude values into amplitude bins corresponding to the received logarithmic amplitude values. Hence, the value sorter 370 may be adapted to deliver sorted amplitude values $A_P$, e.g in the form of a table 470 or cumulative histogram table 530, as discussed and illustrated in connection with FIGS. 13B and/or 13C above.

A Peak Value Establisher 375 may be adapted to establish a representative peak value $A_{PR}$ in dependence on the sorted peak amplitude values Ap and the certain amount R of revolution of the monitored rotating part. As mentioned above, in connection with FIG. 11B, the detector 450 may generate a signal indicative of the amount of revolution R, and the duration of measurement may be controlled solely in dependence on the amount of revolution of the rotatable part 8, irrespective of time. Alternatively, the duration $T_{Pm}$ of the measurement session may be controlled in dependence of time information provided by the clock 190 (FIG. 5) in conjunction with speed of rotation information $f_{ROT}$ delivered by detector 450 so that the duration $T_{Pm}$ is adapted to ensure that the monitoring is performed for the desired amount of rotation n*R. In this connection it is noted that R is a positive number larger than one, and n is a positive number equal to one (1) or larger than one (1). The parameter R may be an integer, but it may alternatively be a decimal number. As discussed above, the parameter values R and n may be preset by the manufacturer of apparatus 14, and these values may be stored in the non-volatile memory 52 or in the non-volatile memory 60 (See FIG. 2A). Alternatively, the parameter values R and n may be set by the user of the apparatus 14 prior to performing a measurement session, as discussed in connection with FIG. 11A above. The parameter values R and n may be set by the user by means of the user interface 102, 107 described in connection with FIG. 2A.

The Peak Value Establisher 375 may be adapted to deliver the representative peak value $A_{PR}$ on an output 378 (See FIG. 16) allowing the generated representative peak value $A_{PR}$ to be delivered to display 106 or to port 16.

Accordingly, with reference to FIG. 16, an embodiment of the apparatus 14 includes a peak detector 310 co-operating with log generator 350, a value sorter 370 and a Representative Peak Value Establisher 375 so as to perform the method described in connection with FIGS. 11A, 11B and 12A above.

According to a preferred embodiment, the apparatus 14 also includes an echo suppresser 330, as discussed above in connection with FIG. 16. The echo suppresser 330, also referred to as burst rejector 330, may be coupled to receive the detected peak values $A_P$ from peak detector 310. The apparatus 14 including burst rejector 330 may be adapted to perform the method described in connection with FIG. 12B. Hence, burst rejector 330 may be adapted to deliver output peak values $A_{PO}$ on a burst rejector output 333 in response to received detected peak values $A_P$. The burst rejector 330 may be adapted to control the delivery of said output peak values $A_{PO}$ such that said output peak values $A_{PO}$ are delivered at a delivery frequency $f_{es}$, wherein the delivery frequency $f_{es}=e*f_{ROT}$, wherein $f_{ROT}$ is said speed of rotation, and e is a factor having a predetermined value.

Generating a Reference Value

In order to achieve a further improved parameter for indicating which the mechanical state of the monitored part, a standard of comparison may be used. However, since different monitored parts may have somewhat different behaviour, it may be necessary to develop a plurality of reference values, each reference value being adapted for a particular dimension or type of monitored movable part.

As mentioned above, when the monitored rotating part includes a bearing assembly, the representative peak amplitude value $A_{PR}$ is indicative of the mechanical state of the bearing surfaces. In fact, the representative peak amplitude value $A_{PR}$ is indicative of the degree of roughness of the metal surfaces in the rolling interface. Hence, the representative peak amplitude value $A_{PR}$ may provide information about the presence of a damage to a metal surface in the rolling interface of a bearing assembly.

A number of detected signal peaks or detected signal peak values $A_p$ occur during monitoring of every operating bearing due to normal surface roughness which exists even in perfect bearings. As mentioned above, such a detected signal peak or detected signal peak value $A_p$ may reflect a vibration or a shock pulse emanating from the roughness of the metal surfaces in the rolling interface.

Further, as the rotational speed of a bearing increases, the amplitude $A_p$ of the detected signal peak values which occur within the bearing also increase. Accordingly, reference values can be obtained empirically by measuring the amplitude of detected signal peak values in a large number of new, perfect ball and rolling bearings. These new, undamaged bearings constitute control bearings, and signal peak values $A_{PRref}$ detected by measurements on the control bearings can be used as reference values.

In order to achieve reference values $_{APRref}$ applicable at for each separate bearing type when running at all the relevant rotational speeds, signal peak values $A_p$ are recorded for several different rotational speeds, i.e. by running each control bearing at several different rotational speeds. The control bearing, must, of course, be correctly mounted, adequately lubricated, and otherwise properly handled so that all conditions normally responsible for bearing failure, with the exception of material fatigue, are substantially eliminated.

A relative rolling velocity $V_r$ of the rolling elements of the control bearing may be determined in accordance with the formula:

$$V_r = f_{ROT} * D_m \qquad \text{(Eq 2)}$$

wherein:

$f_{ROT}$ is the rotational speed of the rotational shaft or bearing, expressed for example as revolutions per second; and $$D_m = (D_I + D_O)/2 \qquad \text{(Eq 3)}$$

wherein:

$D_m$ represents a bearing mean diameter;

$D_I$ is the inside diameter of the bearing; and $D_O$ is the outside diameter of the bearing.

The values for $D_m$, $D_I$ and $D_O$ may be expressed in millimeters, for example.

Figure 17:
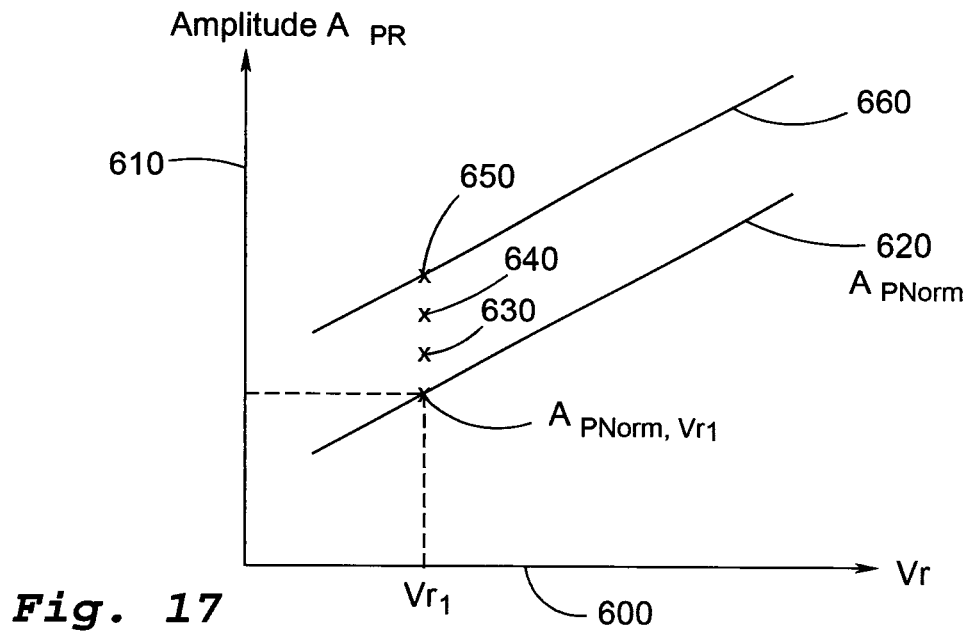
FIG. 17 is an illustration of a typical schedule developed in accordance with an embodiment.

FIG. 17 is an illustration of a typical schedule developed in accordance with an embodiment. In the schedule of FIG. 17, the axis 600 represents relative rolling velocity $V_r$ of the rolling elements the bearing, and the axis 610 represents the amplitude of detected signal peak values $A_p$. According to a preferred embodiment the signal peak values $A_p$ are detected using a resonant Shock Pulse Measurement sensor 10.

A particular reference value $_{APRrefVr1}$ for a particular bearing type may be achieved by recording the detected signal peak value $A_p$ when a control bearing of the particular bearing type runs at the particular relative rolling velocity $V_{r1}$ (See FIG. 17). Reference numeral 620 relates to a curve illustrating that the detected signal peak values for the control bearing, varies in dependence on the relative rolling velocity $V_r$. Accordingly, the curve 620 represents reference signal peak values $_{APRref}$ detected for a control bearing which is correctly mounted, adequately lubricated, and otherwise properly handled so that substantially all conditions normally responsible for bearing failure are eliminated.

The detected signal peak values to be used as reference values $_{APRref}$, may be obtained in accordance with any of the above described manners, e.g. as the R:th largest peak value, or as the n:th largest peak value, or as an estimated representative peak value, wherein the estimation step includes estimating a not-so-frequent highest peak amplitude value $A_{PR}$, 590 (See FIG. 15A) based on the nature of the Gaussian function being such that an occurrence frequency of low amplitude values 550, 560 (See FIG. 15A) is informative about the amplitude of the not-so-frequent highest peak amplitude values $A_{PR}$, 590.

Reference numerals 630, 640 and 650 represent gradually increasing detected values of the representative peak value $A_{PR}$ as an originally undamaged movable part is getting worn. The illustrated gradually increasing detected values 630, 640 and 650 are shown in relation to a particular relative rolling velocity $V_{r1}$, but an actual movable part may, of course, run at a variable speed of rotation $f_{ROT}$. The highest illustrated value 650 may represent an amplitude of the representative peak value $A_{PR}$ which indicates that the condition of the monitored part has deteriorated to such a degree that breakdown may be imminent. Accordingly, the curve 660 represents signal peak values $A_{PRFI}$ detected for a control bearing which has been worn to such a degree that bearing failure is imminent.

When a bearing assembly 7 (See FIG. 1) is monitored, a representative peak value $A_{PR}$ may be generated or estimated, as described above, and the representative peak value $A_{PR}$ is to be compared with the corresponding reference value. Alternatively, a normalized representative peak value $A_{PRNorm}$ can be generated in accordance with the following equation:

$$A_{PRNorm} = A_{PR,Vr} - A_{PRrefVr} \qquad (eq\ 4)$$

Wherein $A_{PR,Vr}$ is the generated or estimated representative peak value $A_{PR}$ obtained when the movable part was rotating at a speed $f_{ROT}$ corresponding to the relative rolling velocity $V_r$; and $A_{PRrefVr}$ is the reference value $A_{PRrefVr}$ for a particular bearing type as obtained by monitoring an undamaged control bearing of the particular bearing type and recording the detected signal peak value occurring with an occurrence frequency of once every R:th revolution when it runs at the particular relative rolling velocity $V_r$.

An embodiment of a procedure for establishing reference values $A_{PRrefVr}$, for a particular type of bearing for all relevant rotational speeds, includes the steps of:

monitoring the control bearing when running at two different speeds of revolution, recording, as a first reference value ($A_{PRV1}$), the highest signal peak value $A_{pR}$ occurring once every R:th revolution when running the control bearing at the first speed, and recording, as a second reference value ($A_{PRV2}$), the highest signal peak value $A_{pR}$ occurring once every R:th revolution when running the control bearing at the second speed, estimating a third reference value ($A_{PRV3}$) for use as a reference when a monitored bearing runs at a third speed, said third reference value ($A_{PRV3}$) being generated in dependence on said first reference value ($A_{PRV1}$) and said second reference value ($A_{PRV2}$).

Lubrication Condition Analysis

Whereas the amplitude of peaks $A_{PR}$ having an occurrence frequency of less than one peak per revolution is indicative of the mechanical state of the bearing surfaces, the inventor found that the amplitude of peaks $A_{PL}$ having an occurrence frequency of more than one peak per revolution is indicative of the lubrication condition of the bearing surfaces.

Figure 18:
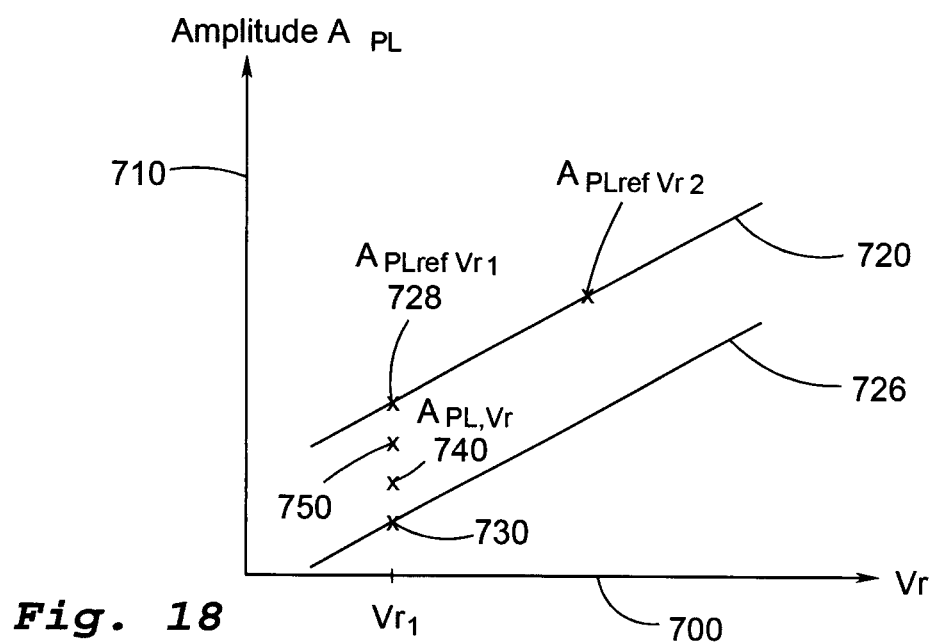
FIG. 18 is an illustration of an embodiment of a schedule for detection of the lubrication condition of the bearing surfaces.

FIG. 18 is an illustration of an embodiment of a schedule for detection of the lubrication condition of the bearing surfaces. In the schedule of FIG. 18, the axis 700 represents relative rolling velocity $V_r$ of the rolling elements the bearing, and the axis 710 represents the amplitude of detected signal peak values $A_{pL}$. According to a preferred embodiment the signal peak values $A_{pL}$ are detected using a resonant Shock Pulse Measurement sensor 10.

A particular lubrication reference value $A_{PLrefVr1}$ for a particular bearing type may be achieved by recording the detected signal peak value $A_{pL}$ when a control bearing of the particular bearing type runs at the particular relative rolling velocity $V_{r1}$ (See FIG. 18). Reference numeral 720 relates to a curve illustrating that the detected signal peak values for a control bearing, varies in dependence on the relative rolling velocity $V_r$. Accordingly, the curve 720 represents reference signal peak values $A_{PLref}$ detected for a control bearing which is correctly mounted, and otherwise properly handled so that substantially all conditions normally responsible for bearing failure are eliminated. However, the curve 720 represents reference signal peak values $A_{PLref}$ detected for the control bearing when it is a run in an unlubricated condition, i.e. without any lubrication. This unlubricated condition will be discussed in further detail later in this document.

The detected signal peak values to be used as reference values $A_{PLref}$, may be obtained in the following manner:

receiving a first digital signal ($S_{MD}$, $S_R$, $S_F$) dependent on mechanical vibrations emanating from rotation of said part;

analysing said first digital signal so as to detect peak amplitude values ($A_{PL}$) during a finite time period ($T_{Pm}$), said finite time period corresponding to a predetermined amount (A) of revolution of said rotatable part; said predetermined amount (A) of revolution corresponding to at least one revolution of said monitored rotatable part;

defining a plurality of amplitude ranges, each amplitude range corresponding to a peak occurrence frequency of more than one peak per revolution;

sorting said detected peak amplitude values (Ap) into corresponding amplitude ranges so as to reflect occurrence of detected peak amplitude values (Ap) within said plurality of amplitude ranges;

establishing a peak amplitude value ($A_{PL}$) for detected peaks having an occurrence frequency of about $N_L$ peaks per revolution, said occurrence frequency value $N_L$ being a number higher than one.

According to an embodiment the amplitude of detected peaks having an occurrence frequency of about $N_L$=40 peaks per revolution may be used for indication the lubrication condition.

An embodiment of a procedure for establishing reference values $A_{PLrefVr}$, for a particular type of bearing for all relevant rotational speeds $V_r$, includes the steps of:

monitoring the unlubricated control bearing when running at two different speeds of revolution, recording, as a first reference value ($A_{PLrefV1}$), the peak amplitude value ($A_{PL}$) for detected peaks having an occurrence frequency of about $N_L$ peaks per revolution, said occurrence frequency value $N_L$ being a number higher than one, when running the bearing at the first speed (V1), and recording, as a second reference value ($A_{PLrefV2}$), the peak amplitude value ($A_{PL}$) for detected peaks having an occurrence frequency of about $N_L$ peaks per revolution, said occurrence frequency value $N_L$ being a number higher than one, when running the bearing at the second speed (V2), estimating a third reference value ($A_{PLrefV3}$) for use as a third reference ($A_{PLrefV3}$) when a monitored bearing runs at a third speed (V3), said third reference value ($A_{PLrefV3}$) being generated in dependence on said first reference value ($A_{PLrefV1}$) and said second reference value ($A_{PLrefV2}$).

In the above described manner, reference values for different relative speeds Vr may be established, and corresponding amplitude values $A_{PL}$ may be plotted. By so doing, a curve 720 representing reference signal peak values $A_{PLref}$ may be achieved (See FIG. 18). Hence, the curve 720 represents reference signal peak values $A_{PLref}$ detected for the control bearing when it is a run in an unlubricated condition, i.e. without any lubrication.

If the control bearing is then properly lubricated, and the above procedure of measurement is repeated, another curve 726 may be achieved, indicating signal peak values $A_{PL}$ detected for the control bearing when it is a run in a properly lubricated condition. With reference to FIG. 18, reference numeral 728 indicates a first reference value $A_{PLV1}$, for detected peaks having an occurrence frequency of about 40 peaks per revolution when running the un-lubricated control bearing at the first speed V1.

As indicated by reference numeral 730, detected peaks having an occurrence frequency of about 40 peaks per revolution have a lower amplitude, when running the same control bearing at the first speed V1 in a properly lubricated state. Hence, the amplitude value $A_{PL}$ of peaks having an occurrence frequency of about 40 peaks per revolution may be used to indicate the lubrication condition of a bearing assembly.

Reference numeral 740 and 750 represent gradually increasing detected values of the peak value $A_{PL}$ as an originally well lubricated movable part has been running for long time so that the lubrication condition deteriorates. The illustrated gradually increasing detected values 740 and 750 are shown in relation to a particular relative rolling velocity $V_{r1}$, but an actual movable part may, of course, run at a variable speed of rotation $f_{ROT}/V_r$. The highest illustrated value 728 represents an amplitude of the peak value $A_{LR}$ which indicates that the lubrication condition of the monitored part has deteriorated to such a degree that substantially no lubrication remains in the rolling interface.

When a bearing assembly 7 (See FIG. 1) is monitored, a peak value $A_{PL}$ may be generated or estimated, as described above, and the lubrication peak value $A_{PL}$ is to be compared with the corresponding reference value. Alternatively, a normalized lubrication peak value $A_{PLNorm}$ can be generated in accordance with the following equation:

$$A_{PLNorm} = A_{PLrefVr} - A_{PL,Vr} \qquad (EQ\ 4)$$

Wherein $A_{PLrefVr}$ is the reference value $A_{PLrefVr}$ for that particular bearing type and for the particular relative rolling velocity $V_r$, as obtained by monitoring an un-lubricated control bearing of the particular bearing type and recording the detected signal peak values occurring with an occurrence frequency of $N_L$ peaks per revolution; and $A_{PR,Vr}$ is the generated or estimated lubrication peak value $A_{PL}$ obtained when the movable part was rotating at a speed $f_{ROT}$ corresponding to the relative rolling velocity $V_r$ (See eq2 and eq3 above)

After a schedule of lubrication reference values $A_{PLrefVr}$ has been developed for a control bearing, as hereinbefore described, an operating bearing, having like physical characteristics, and which may comprise a part of a machine, may be evaluated by measuring the relative velocity of its rolling elements and the peak amplitude values which occur within it. The lubricational condition of the operating bearing may then be evaluated with reference to the established schedule.

In order to compensate for differences in surface roughness encountered in bearing of different types or in bearings of the same type, but made by different manufacturers, a control bearing is employed, which has physical characteristics substantially matching the physical characteristics of the operating bearing to be evaluated. The control bearing is run, first in an unlubricated condition, and then in a lubricated condition, to enable determination of the dampening effect of the elastohydrodynamic lubricant film upon shocks occurring with the control bearing, as discussed above in connection with FIG. 18.

In evaluating the lubricational condition of an operating rolling element bearing in accordance with a method of the present invention, utilizing the shock pulse measuring technique hereinbefore generally described, it is necessary to acquire information relating to a running control bearing having physical characteristics substantially matching the physical characteristics of the operating bearing to the evaluated. The control bearing, must, of course, be correctedly mounted, adequately lubricated, and otherwise properly handled so that all conditions normally responsible for bearing failure, with the exception of material fatigue, are substantially eliminated. The relative rolling velocity $V_r$ of the rolling elements of the control bearing may be determined in accordance with equations (2) and (3), discussed above.

After a schedule has been developed for a control bearing, as hereinbefore described, an operating bearing, having like physical characteristics, and which may comprise a part of a machine, may be evaluated by measuring the relative velocity $V_r$ of its rolling elements and the amplitude of peaks $A_{PL}$ which occur within it. The lubricational condition of the operating bearing may then be evaluated with reference to the established schedule.

Figure 19:
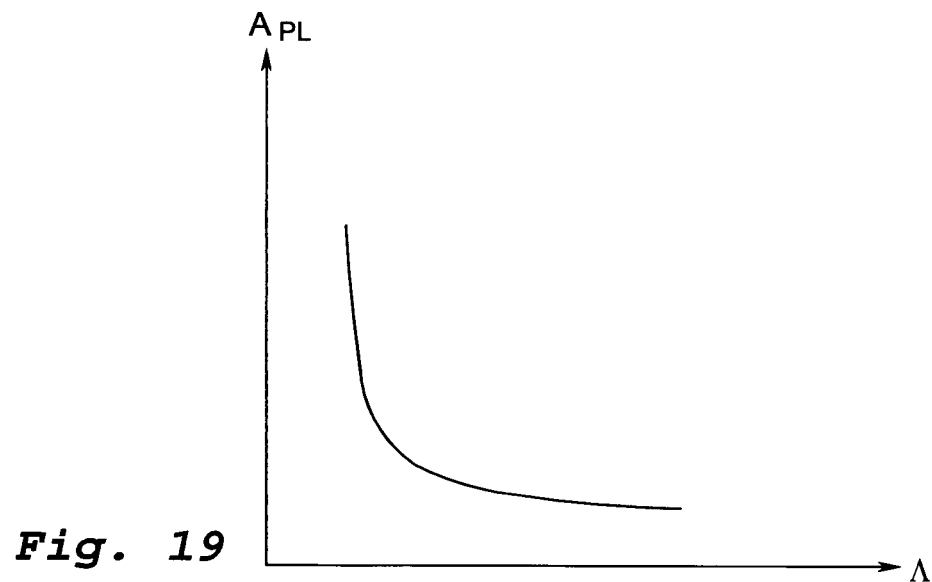
FIG. 19 is an illustration of correlation between the amplitude of peaks $A_{PL}$ having an occurrence frequency of more than one peak per revolution and the elastohydrodynamic lubricant film parameter Λ.

FIG. 19 is an illustration of correlation between the amplitude of peaks $A_{PL}$ having an occurrence frequency of more than one peak per revolution and the elastohydrodynamic lubricant film parameter $\Lambda$.

The elastohydrodynamic film parameter of the running control bearing may be calculated based upon measurements, made under controlled conditions. More specifically, a predetermined load is first applied to the running control bearing. The temperature of the running control bearing is also measured. The characteristics of the lubricant are, of course, known. The elastohydrodynamic oil film parameter is determined in accordance with the formula:

$$\Lambda = H[\mu_0 \alpha N]^{0.73} P_0^{0.09} \qquad (EQ\ 5)$$

wherein:

$\Lambda$ is the elastohydrodynamic lubricant film parameter.

H is a value which pertains to the geometry and dimensions of the test bearing.

$\mu_0$ is the dynamic viscosity of the lubricant measured at bearing operating temperature.

$\alpha$ is pressure coefficient of viscosity measured at operating temperature.

N is speed of rotation, and $P_0$ is the equivalent load calculated in accordance with the formula:

$$P_0 = X_0 F_r + Y_0 F_a \qquad (EQ\ 6)$$

wherein:

$X_0$ is a radial factor;

$F_r$ is the actual constant radial load;

$Y_0$ is a thrust factor and $F_a$ is the actual constant thrust load.

Figure 20:
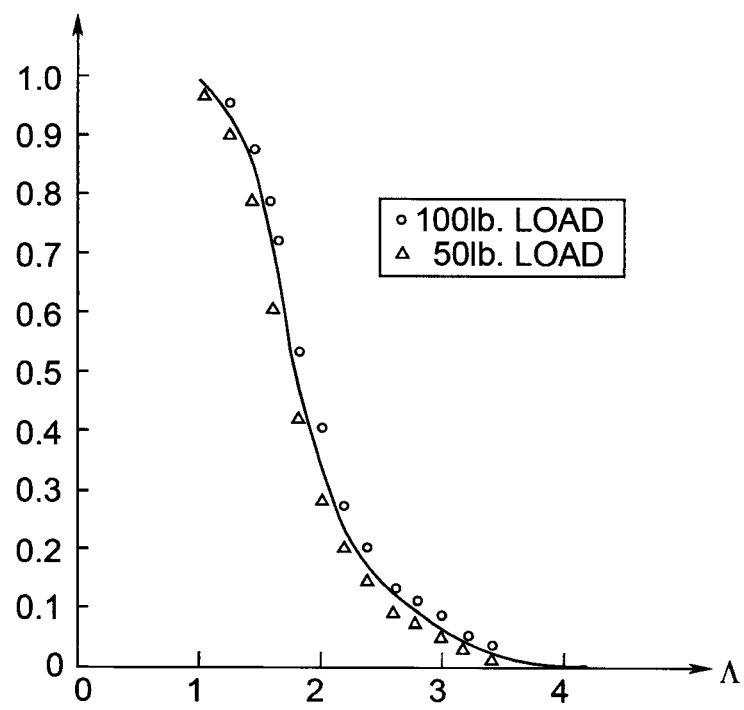
FIG. 20 is an illustration of a curve indicating the relation between the elastohydrodynamic film parameter Λ and the fraction of time there is metal-to-metal contact in a bearing for two different loads on the bearing.

There is a relationship between the time percentage during which metal-to-metal contact is prevented in a running bearing by the presence of a lubricant film and the elastohydrodynamic film parameter Λ of the lubricant. This relationship, established by T E Tallian, is illustrated by the Tallian curve shown in FIG. 20, and it may be utilized to verify the calculated value of Λ, as determined by the aforesaid formula and test measurements. Hence, FIG. 20 is an illustration of a curve indicating the relation between the elastohydrodynamic film parameter Λ (the horizontal axis in FIG. 20) and the fraction of time there is metal-to-metal contact in a bearing (the vertical axis in FIG. 20) for two different loads on the bearing. A measurement of the time percentage during which metal-to-metal contact is prevented in the running control bearing by the presence of the lubricant may be made substantially simultaneously with the other measurements used in calculating the value of Λ. Reference to the aforesaid relationship, as established by Tallian, may be had to provide a rough check of the calculated values for Λ at various running speeds of the control bearing.

In accordance with the invention, an improved measuring instrument is provided for providing a measurement value indicative of a lubricant film parameter of an operating bearing and providing a direct output of the latter parameter. The instrument may further include means for outputting signals indicating other operating conditions of the bearing, such as a value or a signal indicative of a damage to the rolling interface of the monitored bearing.

Figure 21:
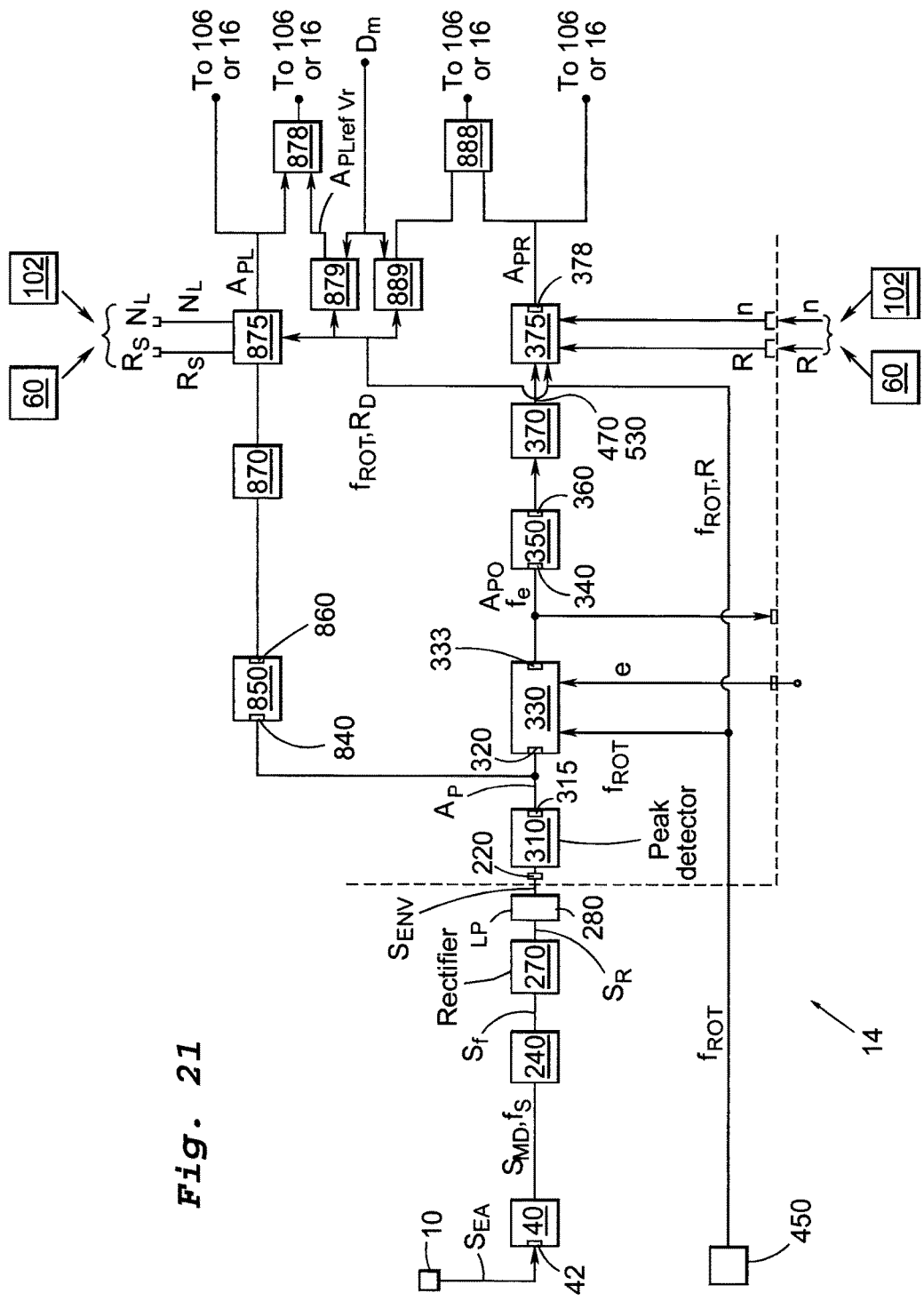
FIG. 21 is a block diagram illustrating an improved apparatus according to an embodiment of the present invention.

Referring now to FIG. 21 there is shown a block diagram illustrating an improved apparatus embodying the present invention, indicated generally by the reference numeral 14, and used in practicing the methods hereinbefore described. The illustrated apparatus 14 includes a transducer 10 for converting mechanical vibrations in a bearing to analogous electrical oscillations $S_{EA}$. The presently preferred transducer comprises a resonant piezoelectric accelerometer, as described above in this document.

According to an embodiment, the apparatus 14 may operate as described above with reference to FIGS. 1-17 for identifying or estimating representative peak amplitude values $A_{PR}$ indicative of a mechanical state of the rolling interface in response to the analogous electrical oscillations $S_{EA}$ generated by the transducer 10. The embodiment according to FIG. 21 is also adapted to identify peaks $A_{PL}$, the amplitude of which are indicative of the lubrication condition of the monitored bearing surfaces.

As shown in FIG. 21, the detected peak values $A_P$ delivered on output 315 of peak detector 310 may be delivered to two legs of further signal analysis. The lower leg, as illustrated in FIG. 21, may deliver the representative peak amplitude values $A_{PR}$ on an output 378, while the upper leg delivers peaks $A_{PL}$, the amplitude of which are indicative of the lubrication condition of the monitored bearing surfaces.

The detected signal peaks or detected signal peak values Ap may be delivered from the peak detector output 315 to an input 840 of a log generator 850. The log generator 850 is adapted to generate the logarithmic amplitude values corresponding to the amplitude of the received detected signal peaks or detected signal peak values Ap. Hence, an output 860 of log generator 850 is adapted to deliver logarithmic amplitude values. A value sorter 870 is adapted to receive the logarithmic amplitude values and to sort the received logarithmic amplitude values into amplitude bins corresponding to the received logarithmic amplitude values. Hence, the value sorter 870 may be adapted to deliver sorted amplitude values $A_P$, e.g in the form of a table, like the table histogram 470 and/or cumulative histogram table 530, as discussed and illustrated in connection with FIGS. 13B and/or 13C above.

At the end of a measuring session, a Lubrication Peak Value Establisher 875 may be adapted to identify an amplitude bin 500 (See FIG. 13B) containing an peak amplitude value $A_{PL}$ having an occurrence frequency of $N_L$ peaks per revolution, said occurrence frequency value $N_L$ being a number higher than one.

The breadths of the amplitude ranges of table 470 when used for lubrication condition peak values $A_{PL}$ may be settable in order to tune the detection ability. According to an embodiment, the histogram setting may be as described in connection with FIGS. 13A, 13B, and 13C above.

Whereas the lower leg of the signal analysis, as illustrated in FIG. 21 includes an echo suppressor for delivering the representative peak amplitude values $A_{PR}$ on output 378, the upper leg does not include any such echo suppressor for delivering the peaks $A_{PL}$. Hence, when the representative peak amplitude value $A_{PR}$ is generated with an embodiment including the optional echo suppressor 330, a separate histogram table 470 must be generated for the identification of peaks $A_{PL}$. However, when the optional echo suppressor 330 is not included, the Lubrication Peak Value Establisher 875 may operate to use the same histogram values as those used for identifying the representative peak amplitude value $A_{PR}$.

As mentioned above, the inventor realized that the amplitude of peak values having an occurrence frequency of more than once per revolution of the rotationally movable part is indicative of a lubricant film parameter of an operating bearing. Hence, the occurrence frequency of the relevant amplitude must be interpreted in view of the amount of revolution R performed by the rotational part while the amplitude values were collected.

Accordingly, parameters $R_S$ and $N_L$ may be settable, for setting the finite measuring period in terms of an amount of revolution, and for setting the occurrence frequency value $N_L$. The parameter $R_S$, which may be settable via user interface 102 or preset in memory 60 (See FIG. 21 in conjunction with FIG. 2A), can thus define the finite measuring period used for establishing a value $A_{PL}$. Since the occurrence frequency of the peaks indicative of lubrication condition is much higher than the occurrence frequency of the peaks indicative of bearing damage, the finite measuring period for establishing a value $A_{PL}$ may be shorter than the finite measuring period for establishing a value $A_{PR}$.

When a measuring period starts, the Lubrication Peak Value Establisher 875 may be adapted to clear the memory of the 870, and thereafter allow 870 to count occurrence of amplitude values within the set ranges. When the signal $R_D$ received from the sensor 450 indicates that the set amount of revolution $R_S$ has been achieved, the Lubrication Peak Value Establisher 875 may be adapted to identify an amplitude bin having X amplitude values, wherein $$X = R_D * N_L \qquad (EQ\ 7)$$

The amplitude value Ar of the identified bin may be used as a value $A_{PL}$ (see FIG. 13B).

According to another embodiment the Lubrication Peak Value Establisher 875 may be adapted to identify the bin 500 in the accumulated histogram table (see FIG. 13C) containing Z amplitude values, wherein $$Z = R_D * N_L \qquad (EQ\ 8)$$

If no bin includes exactly Z values, then the Lubrication Peak Value Establisher 875 may be adapted to identify the bin 500 a bin containing the closest number of values, i.e. the number N' being closest to $N_L$. Whereas a histogram table according to FIG. 13B may include more than one amplitude bin containing X amplitude values, the accumulated histogram table, as illustrated by FIG. 13C, can only have a single bin having N'=$N_L$ values, due to the nature of an accumulated histogram table. This is evident from looking at the shape of the curve in FIG. 15A, which represents a plot that may be achieved on the basis of data in table 530 representing an accumulated histogram.

According to yet another embodiment the Lubrication Peak Value Establisher 875 may be adapted to identify the Y:th highest amplitude peak. When measuring and collecting peak amplitude values $A_P$ during a time period $T_{PML}$ corresponding to e.g. R=8 full revolutions of the monitored part, and thereafter organising the peak amplitude values $A_P$ in a histogram table, as illustrated in FIG. 13B, the peak amplitude value $A_r$ having an occurrence frequency of more than one peak per revolution is very stable, in the sense that immediately successive repeated measurements on the same bearing will advantageously provide the same or substantially the same value $A_{PL}$. Accordingly, a stable measurement value, i.e. repeatedly providing substantially the same peak amplitude when performing plural measurements on the same rotating part, may be achieved by focusing on the Y:th highest amplitude peak value, wherein Y is $$Y=R_S*N_L \quad (EQ\ 9)$$

Wherein $R_S$ a number indicative of the number of revolutions performed by the monitored part during the peak level monitoring time $T_{PML}$; and $N_L$ is an integer having a value higher than one (1) and lower than about 200.

An embodiment of the invention therefore includes a method of operating an apparatus for analysing the lubrication condition of a machine part rotating with a speed of rotation $f_{ROT}$, comprising the steps of:

receiving a first digital signal $S_{MD}$, $S_R$, $S_F$ dependent on mechanical vibrations emanating from rotation of said part;

analysing said first digital signal so as to detect peak amplitude values Ap during a finite time period $T_{PmL}$, said finite time period corresponding to a certain amount $R_D$ of revolution of said rotatable part; said certain amount $R_D$ of revolution corresponding to more than one revolution of said monitored rotatable part;

sorting said detected peak amplitude values Ap into corresponding amplitude ranges (r) so as to reflect occurrence N of detected peak amplitude values Ap within a plurality $N_R$ of amplitude ranges;

identifying an amplitude range (r) containing sorted peak amplitude values $A_{PL}$ which, during the finite time period $T_{PmL}$, had a mean occurrence frequency of more than once per revolution.

According to an advantageous embodiment the estimation includes selecting the Y:th highest amplitude peak value to be said representative peak amplitude value $A_{PL}$, wherein Y is $$Y=R_S*N_L$$

and wherein $R_S$ a number indicative of the number of revolutions performed by the monitored part during the peak level monitoring time $T_{PML}$; and $N_L$ is an integer having a value higher than one (1) and lower than about 200.

According to preferred embodiments, the occurrence frequency value $N_L$ may be settable. According to an embodiment the Lubrication Peak Value Establisher 875 is adapted to select the amplitude value having an occurrence frequency of $N_L$=40 peaks per revolution.

As mentioned above, in connection with FIG. 11B, the detector 450 may generate a signal $R_D$ (See FIG. 21) indicative of the amount of revolution R, and the duration of measurement may be controlled solely in dependence on the amount of revolution of the rotatable part 8, irrespective of time. Alternatively, the duration $T_{Pm}$ of the measurement session may be controlled in dependence of time information provided by the clock 190 (FIG. 5) in conjunction with speed of rotation information $f_{ROT}$ delivered by detector 450 so that the duration $T_{Pm}$ is adapted to ensure that the monitoring is performed for the desired amount of rotation $R_S$. According to an embodiment, when the apparatus 14 is to generate both of values $A_{PR}$ and $A_{PL}$ simultaneously, the parameter $R_S$ fed into Lubrication Peak Value Establisher 875 may be set to be equal to the product of parameters R and n being fed into Peak Value Establisher 375. In this connection it is noted that R is a positive number larger than one, and n is a positive number equal to one (1) or larger than one (1). The parameter R may be an integer, but it may alternatively be a decimal number.

As discussed above, the parameter values $R_S$ and $N_L$ may be preset by the manufacturer of apparatus 14, and these values may be stored in the non-volatile memory 52 or in the non-volatile memory 60 (See FIG. 2A). Alternatively, the parameter values $R_S$ and $N_L$ may be set by the user of the apparatus 14 prior to performing a measurement session. The parameter values $R_S$ and $N_L$ may be set by the user by means of the user interface 102, 107 described in connection with FIG. 2A.

The Peak Value Establisher 875 may be adapted to deliver the peak value $A_{PL}$ on an output 878 (See FIG. 21) allowing the generated peak value $A_{PL}$ to be delivered to display 106 or to port 16 (see FIG. 2A).

Accordingly, with reference to FIG. 21, an embodiment of the apparatus 14 includes a peak detector 310 co-operating with log generator 350 and/or 850, a value sorter 370 and/or 870 and a Lubrication Peak Value Establisher 875 and/or a Representative Peak Value Establisher 375 so as to perform the method(s) described above.

The Peak Value Establisher 875 may be adapted to deliver the peak value $A_{PL}$ from the output 878 (See FIG. 21) to a first input of a comparator 878, the comparator 878 having another input for receiving a relevant reference value from a reference value provider 879. The reference value provider 879 may provide the reference values $A_{PLrefVr}$, 720, as discussed in connection with FIG. 18.

Similarly, the Representative Peak Value Establisher 375 may be adapted to deliver the peak value $A_{PR}$ from the output 378 (See FIG. 21) to a first input of a comparator 888, the comparator 888 having another input for receiving a relevant reference value APRef,Vr from a reference value provider 889. The reference value provider 889 may provide the reference values $A_{PLrefVr}$, 720, as discussed in connection with FIG. 17, dependent on parameter $D_m$ and actual speed of rotation $f_{ROT}$.

The dampening effect of an elastohydrodynamic lubricational film in a rolling element bearing is directly proportional to lubricational film thickness. As previously noted, the elastohydrodynamic lubricant film parameter comprises a function of lubricant film thickness and the roughness of the lubricated surfaces. This relationship is expressed in the following formula:

$$\Lambda = h_o/R_a \quad (EQ\ 11)$$

wherein:
Λ is the elastohydrodynamic lubricant film parameter.
$h_o$ is the central film thickness and
$R_a$ is the average surface roughness of the lubricated surfaces.

Further, the relationship expressed in the foregoing formula is utilized in conjunction with a pulse peak value measurement technique to provide a practical method for attaining a useful determination of absolute lubricant film thickness in a bearing operating under normal field conditions.

The average surface roughness of a bearing ($R_a$) will, of course, be determined by the manufacturing techniques used in finishing surfaces of the bearing elements. Such manufacturing techniques include microfinishing, grinding, machining and hot rolling and produce varying degrees of surface roughness. Ball bearings, and particularly those in precision applications, such as in aircraft, are usually microfinished. However, the benefits derived from microfinishing other types of bearings, such as industrial roller bearings, for example, are usually not considered great enough to justify the additional cost.

In order to compensate for differences in average surface roughness encountered in bearing of different types or in bearings of the same type, but made by different manufacturers, a control bearing is employed, which has physical characteristics substantially matching the physical characteristics of the operating bearing to be evaluated. The control bearing is run, first in an unlubricated condition, and then in a lubricated condition, to enable determination of the dampening effect of the elastohydrodynamic lubricant film upon shocks occurring with the control bearing.

The term "unlubricated", used in this specification and in the claims which follow, refers to a bearing which is run in a substantially dry condition or at least in the absence of effective lubrication. To reduce the risk of bearing seizure, it may be desirable to "lubricate" the control bearing with an ineffective lubricant, that is a lubricant which has an elastohydrodynamic lubricant film parameter (Λ) not greater than 0.6, such as kerosene, for example, which will function primarily as a coolant rather than as a lubricant.

Preferably, the control bearing is cleaned with a suitable solvent, before it is run, to substantially remove all traces of factory applied lubrication. If a low viscosity lubricant, such as kerosene, is used to prevent bearing seizure at higher operating speeds, a sufficient load may be applied to the control bearing to assure substantially constant metal-to-metal contact within the running bearing. A suitable arrangement for electrical contact measurement may be provided to monitor the control bearing to assure that such metal-to-metal contact is maintained at substantially all times while the control bearing is being run in its unlubricated state.

The relative rolling velocity of the rolling elements of the unlubricated running control bearing is determined. The unlubricated running control bearing is also monitored with a shock pulse measuring instrument, as hereinbefore described, to determine the magnitude of occurring shock pulses occurring at various operational speeds.

The control bearing is then lubricated and the magnitude of occurring shock pulses within the lubricated control bearing is determined at various operating speeds, preferably corresponding to operating speeds at which shock pulse measurements were made in the unlubricated control bearing.

Referring to FIG. 18, curve 720 represents reference signal peak values $A_{PLref}$ detected for the control bearing when it is a run in an unlubricated condition, and curve 726 represents signal peak values $A_{PL}$ detected for the control bearing when it is a run in a lubricated condition.

The difference between the peak values $A_{PLref}$ obtained for the unlubricated control bearing and the signal peak values $A_{PL}$ detected for the lubricated control bearing at any given operating speed $V_r$ enables determination of the dampening effect upon shocks occurring within the bearing at that operating speed attributable to the addition of a sufficient elastohydrodynamic lubricant film. The elastohydrodynamic lubricant film parameter Λ for the lubricated control bearing may be readily determined by one of the methods hereinbefore described.

When sufficient test data has been obtained by operating the control bearing under substantially unlubricated and lubricated conditions, the control bearing is disassembled and the average roughness of the race and bearing element contact surfaces ($R_a$) is determined by physical measurement, utilizing measuring techniques well known in the art. The absolute value of the lubrication film thickness ($h_0$) in the central region of contact may now be calculated using the formula:

$$h_0 = \Lambda R_a \quad (EQ\ 12)$$

With reference to FIG. 18 and equation 4 above, a lubrication peak value $A_{PL}$ may be generated, as described above, and compared with the corresponding reference value in order to gain information indicative of the remaining lubrication film thickness $h_0$ in a monitored bearing assembly 7 (See FIG. 1 in conjunction with FIG. 21 and FIG. 18).

Alternatively, a normalized lubrication peak value $A_{PLNorm}$ can be generated in accordance with equation eq4 above:

$$A_{PLNorm} = A_{PLrefVr} - A_{PL,Vr} \quad (eq\ 4)$$

Wherein
$A_{PLrefVr}$ is the reference value $A_{PLrefVr}$, for that particular bearing type and for the particular relative rolling velocity $V_r$, as obtained by monitoring an un-lubricated control bearing of the particular bearing type and recording the detected signal peak values occurring with an occurrence frequency of $N_L$ peaks per revolution; and $A_{PR,Vr}$ is the generated or estimated lubrication peak value $A_{PL}$ obtained when the movable part was rotating at a speed $f_{ROT}$ corresponding to the relative rolling velocity $V_r$.

Accordingly, the value of the normalized lubrication peak value $A_{PLNorm}$ may indicate the absolute thickness $h_0$ of the lubrication film in the monitored bearing. This information may then be utilized to evaluate the condition of the operating bearing by determining the relative rolling velocity Vr of the rolling elements in the operating bearing and the relevant amplitude values $A_{PL,Vr}$, in the manner described above.

It will now be apparent that a schedule of reference values $A_{PLrefVr}$ obtained by the foregoing method may be utilized in the measuring apparatus 14 herein described. The required information may be stored within the memory 60 of the instrument (See e.g. FIG. 2A), preferably in the form of formulae or linear equations which relate to various bearing types and lubricants used therewith. The instrument is, of course, arranged to receive the required input data, as, for example, the specific identity of the bearing to be monitored and the type of lubricant used in the operating bearing and may be programmed to provide a directed readout of absolute lubricant film thickness $h_0$.

Experimental work performed by others has conclusively established that lubricant film thickness in a rolling element bearing is primarily developed in the inlet region just in advance of the flattened or Hertzian region of the rolling element. An article entitled, Optical analysis of Ball Bearing Starvation, by L. D. Wedeven, D. Evans and A. Cameron, Journal of Lubrication Technology, American Society of Mechanical Engineers, July, 1971, which is hereby adopted by reference as part of the present disclosure, contains an in-depth discussion of ball bearing lubricant starvation and experiments conducted to determine elastohydrodynamic oil film measurements for rolling point contact under starvation conditions utilizing optical interferometry. This experimental work resulted in the development of a semi-empirical formula for determining lubricant thickness in a rolling element bearing and which includes consideration of the effects of lubricant starvation. This formula is used in conjunction with the shock pulse measuring techniques and methods hereinbefore described to provide a practical means for determining occurrence of a lubricant starvation condition in a bearing operating under normal field conditions.

Moreover, a method of discriminating between different types of deteriorated conditions is presented. The method advantageously makes it possible to
  indicate whether or not there is a deteriorated condition in a monitored bearing 7 associated with rotating shaft 8; and
  if there is a deteriorated condition in a monitored bearing 7, then this method provides an indication of the cause of the deteriorated condition.

The analysis method according to an embodiment can
  indicate when the cause for a deteriorated condition is related to a lubrication condition in a rolling interface of bearing surfaces; and an embodiment of this method can also
  indicate when the cause for a deteriorated condition is related to a degree of roughness of the metal surfaces in a rolling interface of said bearing surfaces.

The analysis enables
  Detection of amplitude values ($A_{PL}$, $A_{PR}$) which may be used for indicating whether or not there is a deteriorated condition in a monitored bearing 7 associated with rotating shaft 8; and
  if there is a deteriorated condition in a monitored bearing 7, then the analysis enables discrimination between
    first detected amplitude values ($A_{PL}$) which may be used for indicating a lubrication condition of bearing surfaces on the one hand; and
    second detected amplitude values ($A_{PR}$) which may be used for indicating a mechanical state of bearing surfaces.

According to embodiments of the discrimination between the first detected amplitude values ($A_{PL}$) and the second detected amplitude values ($A_{PR}$) is based on the number ($N_L$) of occurrences per revolution of said peak values ($A_{PL}$, $A_{PR}$); wherein said number occurrences per revolution may relate to the revolution of the rotating shaft 8 associated with a monitored bearing 7.

Figure 22:
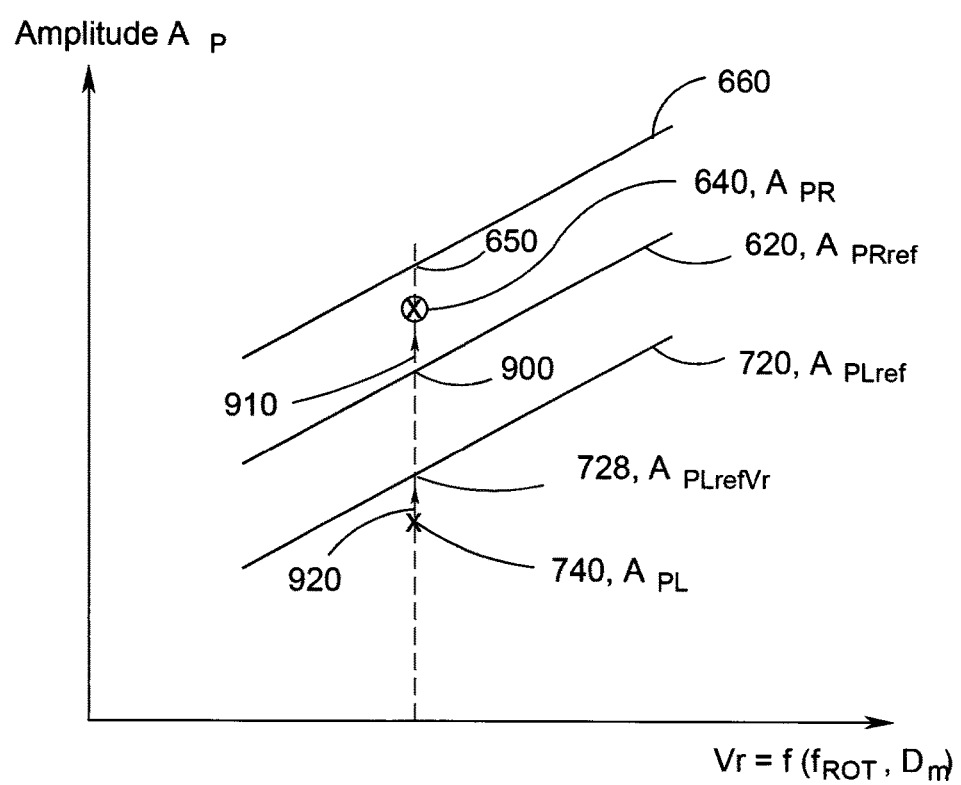
FIG. 22 is an illustration of an embodiment of a schedule for enabling discrimination between a first parameter indicating the lubrication condition of monitored bearing surfaces and a second parameter indicating a mechanical state of bearing surfaces.

FIG. 22 is an illustration of an embodiment of a schedule for enabling discrimination between
  a first parameter $A_{PL}$, 740 indicating the lubrication condition of monitored bearing surfaces (See FIG. 22 and FIG. 18); and
  a second parameter $A_{PR}$, 640 indicating a mechanical state of bearing surfaces (See FIG. 22 and FIG. 17).

The reference numeral 900 indicates a typical lowest amplitude value for the second parameter $A_{PR}$, 640. The amplitude value indicated by numeral 900 corresponds to the typical value of $A_{PR}$ for a perfectly new and well functioning bearing.

As the bearing is getting worn, the value detected for the second parameter $A_{PR}$, 640 will increase in accordance with the degree of wear, when run at the same rotational speed $f_{ROT}$. The arrow 910 indicates how that increased value will reflect in the schedule. The value $A_{PR}$, 640 detected for the second parameter $A_{PR}$, 640 may be compared to the value indicated by 900, for reference to a undamaged control bearing, and/or it may be compared to a the value 650, as discussed in connection with FIG. 17.

The amplitude value of the first parameter $A_{PL}$, 740 may be compared to a first reference value 728, $A_{PLrefVr}$ associated with the monitored bearing type and an actual relative speed $V_{r1}$. The actual relative speed $V_{r1}$ may be calculated in response to a signal $f_{ROT}$ which may be delivered by a speed of rotation detector 450 (See FIG. 1 and FIG. 21). According to an embodiment, the result of such a comparison or the relation between the first parameter $A_{PL}$, 740 and the first reference value 728, $A_{PLrefVr}$ is a measure of the thickness $h_0$ of the lubrication film in the rolling interface. As the thickness $h_0$ of the lubrication film in the rolling interface decreases, e.g. due to long time of operation, the detected amplitude value of the first parameter $A_{PL}$, 740 is going to increase as indicated by arrow 920 so as to approach the relevant lubrication reference value indicated at 728.

An embodiment relates to a method of operating an apparatus for analysing the condition of a machine part rotating with a speed of rotation ($f_{ROT}$, $V_r$), comprising the steps of:
  receiving a first digital signal ($S_{MD}$, $S_R$, $S_F$) dependent on mechanical vibrations emanating from rotation of said part;
  analysing said first digital signal so as to detect peak amplitude values ($A_{PL}$) during a finite time period ($T_{Pm}$), said finite time period corresponding to a predetermined amount (A) of revolution of said rotatable part; said predetermined amount (A) of revolution corresponding to at least one revolution of said monitored rotatable part;
  sorting said detected peak amplitude values (Ap) into corresponding amplitude ranges so as to reflect occurrence of detected peak amplitude values (Ap) within said plurality of amplitude ranges;
  using the amplitude value ($A_{PL}$, $A_{PR}$) associated with at least one amplitude range among said amplitude ranges as a value indicative of a type of condition of said rotating part;
  discriminating between
    amplitude values ($A_{PL}$, $A_{PR}$) used for indicating a lubrication condition of bearing surfaces and
    amplitude values ($A_{PL}$, $A_{PR}$) used for indicating a mechanical state of bearing surfaces
  based on the number of occurrences per revolution of said peak values.

According to an embodiment
the amplitude values ($A_{PL}$) used for indicating a lubrication condition of bearing surfaces have a first occurrence frequency value ($N_L$) in number of peak values per revolution;
said first occurrence frequency value ($N_L$) being a number higher than one peak value per revolution.

According to an embodiment
the amplitude values ($A_{PR}$) used for indicating a mechanical state of bearing surfaces of bearing surfaces have a second occurrence frequency value in number of peak values per revolution;
said second occurrence frequency value being a number lower than one peak value per revolution.

According to an embodiment
said occurrence frequency value $N_L$ is a number higher than ten.

According to an embodiment
said occurrence frequency value $N_L$ is a number in the range from 15 to 150.

According to an embodiment
said occurrence frequency value $N_L$ is a number in the range from 20 to 90.

According to an embodiment
said occurrence frequency value $N_L$ is a number in the range from 25 to 70.

According to an embodiment
said occurrence frequency value $N_L$ reflects a number of peak values per revolution of a monitored part.

According to an embodiment a procedure for establishing reference values ($A_{PRrefVr}$) for a bearing associated with a rotatable part, includes the steps of:
  receiving a first digital signal ($S_{MD}$, $S_R$, $S_F$) dependent on mechanical vibrations emanating from rotation of said rotatable part;
  analysing said first digital signal so as to detect peak amplitude values (Ap) during a finite time period ($T_{Pm}$), said finite time period corresponding to a certain amount (R) of revolution of said bearing; said certain amount (R) of revolution corresponding to more than one revolution of said monitored rotatable part;
  monitoring a control bearing when running at two different speeds of revolution,
  recording, as a first reference value ($A_{PRV1}$), the highest signal peak value ($A_{pR}$) occurring once every R:th revolution when running the control bearing at the first speed, and
  recording, as a second reference value ($A_{PRV2}$), the highest signal peak value ($A_{PR}$) occurring once every R:th revolution when running the control bearing at the second speed,
  estimating a third reference value ($A_{PRV3}$) for use as a reference when a monitored bearing runs at a third speed, said third reference value ($A_{PRV3}$) being generated in dependence on said first reference value ($A_{PRV1}$) and said second reference value ($A_{PRV2}$).

According to an embodiment there is provided:
a system for indicating the lubricational condition of an operating bearing comprising:
  an input for receiving a first digital signal ($S_{MD}$, $S_R$, $S_F$) dependent on mechanical vibrations emanating from rotation of said part;
  means (40, 240, 270, 280, 310) for analysing said first digital signal so as to detect peak amplitude values ($A_{PL}$) during a finite time period ($T_{Pm}$), said finite time period corresponding to a predetermined amount ($R_S$, $R_D$) of revolution of said rotatable part; said predetermined amount ($R_S$, $R_D$) of revolution corresponding to at least one revolution of said monitored rotatable part;
  means (850, 870, 875; 350, 370, 875) for sorting said detected peak amplitude values (Ap) into amplitude bins so as to
    reflect (470) occurrence (N) of detected peak amplitude values (Ap) within a plurality of amplitude range bins, or so as to
    reflect (530) occurrence (N') of detected peaks having an amplitude higher than the amplitude ($A_r'$) of associated amplitude bin (r);
  means (875) for establishing a peak amplitude value ($A_{PL}$) for detected peaks having an occurrence (N') frequency of about $N_L$ peaks per revolution, said occurrence frequency value $N_L$ being a number higher than one;
  means for relating said established peak amplitude value ($A_{PL}$) with reference information contained within a memory (879, 60, 52), and
  means (878) for providing an output ($A_{PLNorm}$) indicative of a lubricant film thickness of the lubricant in said operating bearing in dependence on said relation.

According to an embodiment said means for relating is adapted to create a visual output indicative of said established a peak amplitude value ($A_{PL}$) and indicative of said reference information contained within a memory (879, 60, 52).

According to an embodiment said means for relating is adapted to calculate a value ($A_{PLNorm}$) in dependence on said established peak amplitude value ($A_{PL}$) and said reference information.

The procedures, described in this document, for establishing a value $A_{PL}$ indicative of a lubricational condition may advantageously be used for condition monitoring of rotational parts having a low rotational speed $f_{ROT}$. The present procedures include the feature of:
  analysing the digital signal so as to detect peak amplitude values $A_P$ during a finite time period ($T_{Pm}$), said finite time period corresponding to a predetermined amount ($R_S$, $R_D$) of revolution of said rotatable part; said predetermined amount ($R_S$, $R_D$) of revolution corresponding to at least one revolution of said monitored rotatable part.

This feature advantageously provides measurement results, such as $A_{PL}$ and/or $A_{PR}$, which can be compararable even when the rotational speed $f_{ROT}$ varies. Hence a value $A_{PL1}$ obtained by performing a method as herein described at a first speed of rotation $f_{ROT1}$ can be compared with another value $A_{PL2}$ obtained by performing the same method as herein described at a second speed of rotation $f_{ROT1}$.

The present procedures include the feature of:
  analysing the digital signal so as to detect peak amplitude values $A_P$ during a finite time period ($T_{Pm}$), said finite time period corresponding to a predetermined amount ($R_S$, $R_D$) of revolution of said rotatable part; said predetermined amount ($R_S$, $R_D$) of revolution corresponding to at least one revolution of said monitored rotatable part.

The inventor concluded that the frequency of mechanical vibration pulses and/or shock pulses, due to lubrication condition and mechanical condition of the monitored rotational part, depends on the rotational speed of the monitored rotational part; and hence, it is advantageous to define the finite time period $T_{Pm}$ in terms of amount $R_S$, $R_D$ of revolution of said rotatable part. For these reasons, the present invention is particularly suitable for analysis of low speed rotational parts. Examples of such low speeds are provided below:

In a wind turbine application the shaft whose bearing is analyzed may rotate at a speed of less than 120 revolutions per minute, i.e. the shaft rotational frequency fROT is less than 2 revolutions per second (rps). Sometimes such a shaft to be analyzed rotates at a speed of less than 50 revolutions per minute (rpm), i.e. a shaft rotational frequency fROT of less than 0.83 rps. In fact the speed of rotation may typically be less than 15 rpm. Whereas a shaft having a rotational speed of 1715 rpm, as discussed in the above mentioned book, produces 500 revolutions in just 17.5 seconds; a shaft rotating at 50 revolutions per minute takes ten minutes to produce 500 revolutions. Certain large wind power stations have shafts that may typically rotate at 12 RPM=0.2 rps. At 12 rpm it takes more than four minutes to complete fifty revolutions, and accordingly the risk for impact noise occurring during the measurement is a lot higher when the peak level analysis is to be performed on a rotating part having such a low rotational speed. Similarly certain machine parts in paper mills also rotate at a speed of less than 50 rpm.

As mentioned above, the inventor concluded that it is desirable to monitor a rotating part during a finite time period $T_{PM}$ corresponding to a certain amount R of revolution of said rotatable part; said certain amount R of revolution corresponding to plural revolutions of said monitored rotatable part in order to establish a peak amplitude value $A_P$ which is indicative of the lubricational condition of the monitored part. However, the inventor concluded that it is preferable to monitor a rotating part during a finite time period $T_{PM}$ corresponding to a certain amount R of revolution of said rotatable part; said certain amount R of revolution corresponding to at least two (R=2) revolutions.

When simultaneous analysis is done for establishing a true peak amplitude value $A_{PR}$ which is indicative of the mechanical state of the monitored part; and at the same time establishing a peak amplitude value $A_P$ which is indicative of the lubricational condition of the monitored part, it is advantageous to monitor the rotating part during a finite time period $T_{PM}$ corresponding to a certain amount R of revolution of said rotatable part; said certain amount R of revolution corresponding to at least eight (R=8) revolutions, as mentioned above in this document.

The invention claimed is:

1. A method, carried out by a computer device equipped at least with a memory, of operating an apparatus for detecting a condition of bearing surfaces associated with a rotating machine part of a machine, where the machine part operationally rotates at a rotational speed of less than 120 revolutions per minute, the method comprising:
   employing a vibration sensor, in operable connection with the machine, that generates an analogue vibration signal indicative of mechanical vibrations emanating from said bearing surfaces when said machine part rotates during operation of said machine;
   employing a rotation sensor, in operable connection with the machine, that generates a rotation sensor signal indicative of said rotation of said machine part;
   generating, using an analogue-to-digital converter, a digital vibration signal based on said analogue vibration signal, said digital vibration signal having a sampling frequency associated therewith;
   detecting, by use of said computer device, peak amplitude values in said digital vibration signal;
   sorting, by use of said computer device, said detected peak amplitude values into corresponding amplitude ranges in said memory in a manner of one of
      i) reflecting an occurrence of detected peak amplitude values within a plurality of amplitude ranges, or
      ii) reflecting an occurrence of detected peak amplitude values having an amplitude higher than an amplitude of an associated amplitude range,
   determining, by use of said computer device, based on said rotation sensor signal, when the rotating machine part has revolved a predetermined amount of revolutions, said detecting of peak amplitude values being performed during said predetermined amount of revolutions of the rotating machine part, the predetermined amount of revolutions being more than one revolution of the rotating machine part;
   establishing, by use of said computer device, based on said reflected occurrence, a first peak amplitude value said first peak amplitude value being a value that, during said predetermined amount of revolutions, had a mean occurrence frequency of more than once per revolution;
   generating at least one of a visual output and a numerical value, indicative of a lubrication condition of said bearing surfaces based on the established first peak amplitude value; and
   establishing, by use of said computer device, based on said reflected occurrence, a second peak amplitude value that, during said predetermined amount of revolutions, had a mean occurrence frequency of once per revolution or less than once per revolution, the established second peak amplitude value being indicative of a mechanical condition of said bearing surfaces.

2. The method according to claim 1, wherein said establishing the first peak amplitude value includes:
   identifying, when said predetermined amount of revolutions has been achieved, an amplitude range within which X amplitude values were counted, where $X=R_D*N_L$, where $R_D$ is a number corresponding to said predetermined amount of revolutions, and
   where $N_L$ is said mean occurrence frequency of more than once per revolution; and
   using an amplitude value of said identified amplitude range as said established first peak amplitude value.

3. The method according to claim 2, wherein the amplitude range is a range in a histogram of detected peak amplitude values.

4. The method according to claim 1, wherein said establishing the first peak amplitude value includes:
   identifying, when said predetermined amount of revolutions has been achieved, an amplitude range within which Z amplitude values were counted, wherein Z reflects the occurrence of detected peaks having an amplitude higher than the amplitude of the associated amplitude range, where $Z=R_D*N_L$, where $R_D$ is a number corresponding to said predetermined amount of revolutions, and
   where $N_L$ is said mean occurrence frequency of more than once per revolution; and
   using an amplitude value of said identified amplitude range as said established first peak amplitude value.

5. The method according to claim 1,
wherein said predetermined amount of revolutions is determined based on a preset amount of revolution value and said rotation sensor signal, and
wherein:
said predetermined amount of revolutions corresponds to at least one revolution of said rotating machine part, or
said predetermined amount of revolutions corresponds to at least two revolutions of said rotating machine part, or
said predetermined amount of revolutions corresponds to at least three revolutions of said rotating machine part, or
said predetermined amount of revolutions corresponds to at least four revolutions of said rotating machine part, or
said predetermined amount of revolutions corresponds to at least eight revolutions of said rotating machine part, or
said predetermined amount of revolutions corresponds to at least ten revolutions of said rotating machine part.

6. The method according to claim 1, wherein said predetermined amount of revolutions is at least eight revolutions.

7. The method according to claim 1,
wherein the at least one of a visual output and a numerical value, indicative of the lubrication condition of said bearing surfaces, is generated based on said established first peak amplitude value and a reference lubrication condition peak amplitude value.

8. The method according to claim 7, wherein said reference lubrication condition peak amplitude value is a first peak amplitude value that has been established for said bearing surfaces at an earlier time.

9. The method according to claim 7, wherein said reference lubrication condition peak amplitude value is a first peak amplitude value that has been established in an unlubricated bearing surfaces condition.

10. The method according to claim 1, wherein the visual output, indicative of the lubrication condition of said bearing surfaces, is generated based on said established first peak amplitude value and a number of first peak amplitude values that have been established for said bearing surfaces at earlier times, stored in said memory at said earlier times, and retrieved from said memory for generating said visual output.

11. An apparatus for detecting a condition of bearing surfaces associated with a rotating machine part of a machine, the rotating machine part having a rotational speed less than 120 revolutions per minute, the apparatus comprising:
a vibration sensor which, in operation, is attached to the machine and generates an analogue vibration signal indicative of mechanical vibrations emanating from surfaces of bearings of the rotating machine part during rotation of said rotating machine part;
a rotation sensor which, in operation, is attached to the machine and generates a rotation sensor signal indicative of said rotation of said machine part;
an analogue-to-digital converter that, in operation, generates a digital vibration signal based on said analogue vibration signal, said digital vibration signal having a sampling frequency;
a data processor, in communication with said analogue-to-digital converter and a memory and configured, in accordance with programming code recorded in said memory, to function as:
a peak detector that analyzes said digital vibration signal to detect peak amplitude values of said digital vibration signal;
a value sorter that sorts the detected peak amplitude values and records the detected peak amplitude values into corresponding amplitude ranges in a manner of one of:
i) reflecting an occurrence of detected peak amplitude values within a plurality of amplitude ranges, or
ii) reflecting an occurrence of detected peak amplitude values having an amplitude higher than an amplitude of an associated amplitude range;
a Lubrication Peak Value Establisher; and
a Mechanical Condition Peak Value Establisher,
wherein the data processor is configured to determine, based on said rotation sensor signal, when the rotating machine part has revolved a predetermined amount of revolutions,
wherein the data processor is configured to detect said peak amplitude values on a finite duration of said digital vibration signal, the finite duration corresponding to said predetermined amount of revolutions of the rotating machine part, said predetermined amount of revolutions being at least eight revolutions,
wherein the Lubrication Peak Value Establisher establishes a first peak amplitude value based on said reflected occurrence which, during the finite duration of said digital vibration signal, had a first predetermined mean occurrence frequency of more than once per revolution,
wherein the data processor is configured to generate at least one of a visual output and a numerical value indicative of a lubrication condition of said bearing surfaces based on the established first peak amplitude value, and
wherein the Mechanical Condition Peak Value Establisher establishes a second peak amplitude value which, during said finite duration of said digital vibration signal, had a second predetermined mean occurrence frequency of once per revolution or less than once per revolution, the established second peak amplitude value being indicative of a mechanical condition of said bearing surfaces.

12. The apparatus according to claim 11, wherein said visual output, and/or said numerical value, is indicative of a lubricant film thickness of said bearing surfaces.

13. The apparatus according to claim 11, wherein said predetermined amount of revolutions is at least ten revolutions.

14. A method for detecting a condition of bearing surfaces of a rotating machine part having a speed of rotation, the method comprising the steps of:
providing the apparatus of claim 11;
applying the vibration sensor to a measuring point on the machine; and
generating said at least one of a visual output and a numerical value, indicative of said lubrication condition of said bearing surfaces from the data processor.

15. The apparatus according to claim 11,
wherein the data processor is configured to generate said at least one of a visual output and a numerical value, indicative of the lubrication condition of said bearing surfaces, based on said established first peak amplitude value and a reference lubrication condition peak amplitude value.

16. The apparatus according to claim 15, wherein said reference lubrication condition peak amplitude value is a first peak amplitude value that has been established for said bearing surfaces at an earlier time.

17. The apparatus according to claim 15, wherein said reference lubrication condition peak amplitude value is a first peak amplitude value that has been established in an unlubricated bearing surfaces condition.

18. The apparatus according to claim 11,
wherein the data processor is configured to generate said visual output based on
said established first peak amplitude value, and
a number of first peak amplitude values that have been established for said bearing surfaces at earlier times, stored in said memory at said earlier times, and retrieved from said memory for generating said visual output.

\* \* \* \* \*